US012773525B2

(12) United States Patent
Ott et al.

(10) Patent No.: US 12,773,525 B2
(45) Date of Patent: Oct. 27, 2026

(54) SYSTEMS AND METHODS FOR DELIVERING PRESSURIZED FLUID TO A TARGET SITE ALONE OR IN CONJUNCTION WITH THERAPEUTIC AGENTS

(71) Applicant: Cook Medical Technologies LLC, Bloomington, IN (US)

(72) Inventors: Andreas Ott, Limerick (IE); Inga Rosca, Limerick (IE); Niall Benn, County Limerick (IE); David Slattery, Limerick (IE); Fionan Keady, County Galway (IE); Criostoir O Bhealtun, County Clare (IE); Jack Collins, County Clare (IE); Diarmuid McGee, Galway (IE); Ihsan Kamil, County Limerick (IE)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 994 days.

(21) Appl. No.: 17/968,197

(22) Filed: Oct. 18, 2022

(65) Prior Publication Data

US 2023/0131194 A1 Apr. 27, 2023

Related U.S. Application Data

(60) Provisional application No. 63/271,556, filed on Oct. 25, 2021.

(51) Int. Cl.
*A61M 25/00* (2006.01)
*A61M 37/00* (2006.01)
*A61M 39/22* (2006.01)

(52) U.S. Cl.
CPC ........ *A61M 25/0067* (2013.01); *A61M 37/00* (2013.01); *A61M 39/22* (2013.01)

(58) Field of Classification Search
CPC .................. A61M 11/02; A61M 37/00; A61M 2202/064; A61M 39/22; A61M 2039/224;
(Continued)

(56) References Cited

U.S. PATENT DOCUMENTS

| | | |
|---|---|---|
| 39,678 A | 8/1863 | Russell |
| 170,182 A | 11/1875 | Molesworth |

(Continued)

FOREIGN PATENT DOCUMENTS

| | | |
|---|---|---|
| AU | 9382598 | 3/1999 |
| AU | 2009244462 | 11/2009 |

(Continued)

OTHER PUBLICATIONS

International Preliminary Report on Patentability and Written Opinion regarding PCT/US2022/036498 dated Jan. 25, 2024, 9 pages.

(Continued)

*Primary Examiner* — Nilay J Shah
(74) *Attorney, Agent, or Firm* — Vivacqua Crane, PLLC

(57) ABSTRACT

A system suitable for delivering a therapeutic agent to a target site may include a container for holding a therapeutic agent; a pressure source having pressurized fluid, the pressure source in selective fluid communication with at least a portion of the container; a catheter in selective fluid communication with the container and configured for delivery of the therapeutic agent or the pressurized fluid to a target site; and a housing configured to securely retain the container and movably support a switch, where the switch is movable between a first position and a second position, where when the switch is in the first position, delivery of the therapeutic agent is prevented while delivery of the pressurized fluid is permitted, and where when the switch is in the second position, delivery of the therapeutic agent is permitted.

20 Claims, 34 Drawing Sheets

(58) Field of Classification Search
CPC .......... A61M 39/225; A61M 2039/226; A61M 13/00; A61M 13/003; A61M 2205/8225; F16K 11/0716; A61B 1/015; A61B 1/00068
See application file for complete search history.

(56) References Cited

U.S. PATENT DOCUMENTS 280,202 A 6/1883 Mattson
442,785 A 12/1890 Schoettl
460,458 A 9/1891 Bates
471,865 A 3/1892 Howard
533,489 A 2/1895 Ogram
566,411 A 8/1896 Schoene
576,437 A 2/1897 Elliot
693,587 A 2/1902 Campbell
775,985 A 11/1904 McKain
881,238 A 3/1908 Hasbrouck
904,149 A 11/1908 Rachmann
938,648 A 11/1909 DeVilbiss
1,022,601 A 4/1912 Rumberg et al.
1,114,114 A 10/1914 Cochenour
1,145,520 A 7/1915 Smith
1,261,503 A 4/1918 Figgis
1,357,452 A 11/1920 Hall
1,466,119 A 8/1923 Claflin
1,521,396 A 12/1924 Scott
1,685,280 A 9/1928 Findley
1,934,793 A 11/1933 Crain et al.
2,004,402 A 6/1935 Conklin
2,151,418 A 3/1939 Bolte
2,223,611 A 12/1940 Gross
2,307,986 A 1/1943 Bolte et al.
2,390,313 A 12/1945 Macgill
2,507,702 A 5/1950 Fields
2,519,555 A 8/1950 Fields
2,609,155 A 9/1952 Fosnaugh
2,632,444 A 3/1953 Kas
2,805,013 A 9/1957 Cordis
2,934,314 A 4/1960 Chambers et al.
2,956,579 A 10/1960 Moore et al.
3,016,895 A 1/1962 Sein et al.
3,050,261 A 8/1962 Littlefield
3,207,618 A 9/1965 Hart
3,506,008 A 4/1970 Huck
3,540,444 A 11/1970 Moreland
3,572,335 A 3/1971 Robinson
3,589,363 A 6/1971 Banko et al.
3,599,866 A 8/1971 Bolton
3,632,046 A 1/1972 Hengesbach
3,647,143 A 3/1972 Gauthier et al.
3,649,299 A 3/1972 Sholl
3,667,465 A 6/1972 Voss
3,710,400 A 1/1973 Sparks
3,742,955 A 7/1973 Battista et al.
3,744,493 A 7/1973 Booher et al.
3,762,410 A 10/1973 Bindel
3,788,315 A 1/1974 Laurens
3,815,595 A 6/1974 Bar
3,900,022 A 8/1975 Widran
3,916,896 A 11/1975 Ballard
4,009,637 A 3/1977 Bittner
4,017,007 A 4/1977 Riccio
4,040,420 A 8/1977 Speer
4,174,811 A 11/1979 Binder et al.
4,184,258 A 1/1980 Barrington et al.
4,204,539 A 5/1980 Van Brugge
4,204,645 A 5/1980 Hopp
4,210,140 A 7/1980 James et al.
4,359,049 A 11/1982 Redl et al.
4,391,276 A 7/1983 Lazarus et al.
4,423,727 A 1/1984 Widran et al.
4,427,450 A 1/1984 Kostansek
4,427,650 A 1/1984 Stroetmann
4,516,442 A 5/1985 Davis
4,534,345 A 8/1985 Wetterlin
4,539,716 A 9/1985 Bell
4,552,556 A 11/1985 Urquhart et al.
4,578,067 A 3/1986 Cruz, Jr.
4,606,501 A 8/1986 Bate et al.
4,620,847 A 11/1986 Shishov et al.
4,631,055 A 12/1986 Redl et al.
4,637,816 A 1/1987 Mann
H257 H 4/1987 Barditch et al.
4,655,211 A 4/1987 Sakamoto et al.
4,657,536 A 4/1987 Dorman
4,735,616 A 4/1988 Eibl et al.
4,738,658 A 4/1988 Magro et al.
4,738,740 A 4/1988 Pinchuk
4,752,466 A 6/1988 Saferstein et al.
4,790,819 A 12/1988 Li et al.
4,798,606 A 1/1989 Pinchuk
4,803,977 A 2/1989 Kremer, Jr.
4,846,405 A 7/1989 Zimmermann
4,850,355 A 7/1989 Brooks et al.
D303,139 S 8/1989 Morgan
4,872,450 A 10/1989 Austad
4,874,368 A 10/1989 Miller et al.
4,890,612 A 1/1990 Kensey
4,900,303 A 2/1990 Lemelson
4,902,278 A 2/1990 Maget et al.
4,902,281 A 2/1990 Avoy
4,927,410 A 5/1990 Kovacs
4,929,246 A 5/1990 Sinofsky
4,941,874 A 7/1990 Sandow et al.
4,941,880 A 7/1990 Burns
4,945,050 A 7/1990 Sanford et al.
4,946,870 A 8/1990 Partain, III et al.
4,950,234 A 8/1990 Fujioka et al.
4,969,874 A 11/1990 Michel et al.
4,978,336 A 12/1990 Capozzi et al.
4,994,028 A 2/1991 Leonard et al.
5,009,637 A 4/1991 Newman et al.
5,015,580 A 5/1991 Christou et al.
5,021,059 A 6/1991 Kensey et al.
5,053,000 A 10/1991 Booth et al.
5,059,187 A 10/1991 Sperry et al.
5,061,180 A 10/1991 Wiele
5,063,025 A 11/1991 Ito
5,064,413 A 11/1991 McKinnon et al.
5,106,370 A 4/1992 Stewart
5,116,315 A 5/1992 Capozzi et al.
5,120,657 A 6/1992 McCabe et al.
5,129,825 A 7/1992 Discko, Jr.
5,129,882 A 7/1992 Weldon et al.
5,133,701 A 7/1992 Han
5,135,484 A 8/1992 Wright
5,141,515 A 8/1992 Eberbach
5,147,292 A 9/1992 Kullas et al.
5,149,655 A 9/1992 McCabe et al.
5,165,604 A 11/1992 Copp, Jr.
5,176,642 A 1/1993 Clement
5,179,022 A 1/1993 Sanford et al.
D333,000 S 2/1993 Good et al.
5,204,253 A 4/1993 Sanford et al.
5,207,641 A 5/1993 Allton
5,219,328 A 6/1993 Morse et al.
5,226,567 A 7/1993 Sansalone
5,226,877 A 7/1993 Epstein
RE34,365 E 8/1993 Theeuwes
5,273,531 A 12/1993 Knoepfler
5,292,309 A 3/1994 Van Tassel et al.
5,310,407 A 5/1994 Casale
5,312,331 A 5/1994 Knoepfler
5,312,333 A 5/1994 Churinetz et al.
5,328,459 A 7/1994 Laghi
5,330,426 A 7/1994 Kriesel et al.
5,337,740 A 8/1994 Armstrong et al.
5,391,183 A 2/1995 Janzen et al.
5,392,992 A 2/1995 Farnsteiner et al.
5,395,326 A 3/1995 Haber et al.
5,405,607 A 4/1995 Epstein
5,415,631 A 5/1995 Churinetz et al.
5,429,278 A 7/1995 Sansalore

(56) References Cited

U.S. PATENT DOCUMENTS

| | | | |
|---|---|---|---|
| 5,445,612 | A | 8/1995 | Terakura et al. |
| 5,447,499 | A | 9/1995 | Allaire et al. |
| 5,469,994 | A | 11/1995 | Reh et al. |
| 5,470,311 | A | 11/1995 | Setterstrom et al. |
| 5,484,403 | A | 1/1996 | Yaokum et al. |
| 5,497,232 | A | 3/1996 | Watano et al. |
| 5,503,623 | A | 4/1996 | Tilton, Jr. |
| 5,513,630 | A | 5/1996 | Century |
| 5,518,546 | A | 5/1996 | Williams et al. |
| 5,520,658 | A | 5/1996 | Holm |
| 5,520,667 | A | 5/1996 | Roche |
| 5,538,162 | A | 7/1996 | Reh et al. |
| 5,546,932 | A | 8/1996 | Galli |
| 5,553,741 | A | 9/1996 | Sancoff et al. |
| 5,558,646 | A | 9/1996 | Roche |
| 5,582,596 | A | 12/1996 | Fukunaga et al. |
| 5,584,807 | A | 12/1996 | McCabe |
| 5,584,815 | A | 12/1996 | Pawelka et al. |
| 5,594,987 | A | 1/1997 | Century |
| 5,601,603 | A | 2/1997 | Illi |
| 5,605,541 | A | 2/1997 | Holm |
| 5,612,050 | A | 3/1997 | Rowe et al. |
| 5,665,067 | A | 9/1997 | Linder et al. |
| 5,697,947 | A | 12/1997 | Wolf et al. |
| 5,707,402 | A | 1/1998 | Heim |
| 5,749,968 | A | 5/1998 | Melanson et al. |
| 5,759,171 | A | 6/1998 | Coelho |
| 5,788,625 | A | 8/1998 | Plouhar et al. |
| 5,865,796 | A | 2/1999 | McCabe |
| 5,873,530 | A | 2/1999 | Chizinsky |
| 5,882,332 | A | 3/1999 | Wijay |
| 5,895,400 | A | 4/1999 | Abela |
| 5,902,228 | A | 5/1999 | Schulsinger et al. |
| 5,919,184 | A | 7/1999 | Tilton, Jr. |
| 5,951,531 | A | 9/1999 | Ferdman et al. |
| 6,007,515 | A | 12/1999 | Epstein et al. |
| 6,013,050 | A | 1/2000 | Bellhouse et al. |
| 6,021,776 | A | 2/2000 | Allred et al. |
| 6,027,471 | A | 2/2000 | Fallon et al. |
| 6,059,749 | A | 5/2000 | Marx |
| 6,077,217 | A | 6/2000 | Love et al. |
| 6,117,150 | A | 9/2000 | Pingleton et al. |
| 6,123,070 | A | 9/2000 | Bruna |
| 6,158,624 | A | 12/2000 | Grigg et al. |
| 6,165,201 | A | 12/2000 | Sawhney et al. |
| 6,368,300 | B1 | 4/2002 | Fallon et al. |
| 6,394,975 | B1 | 5/2002 | Epstein |
| 6,428,505 | B1 | 8/2002 | Taylor |
| 6,454,786 | B1 | 9/2002 | Holm et al. |
| 6,461,325 | B1 | 10/2002 | Delmotte et al. |
| 6,461,361 | B1 | 10/2002 | Epstein |
| 6,478,754 | B1 | 11/2002 | Babeav |
| 6,537,246 | B1 | 3/2003 | Unger et al. |
| 6,554,792 | B2 | 4/2003 | Hughes et al. |
| 6,610,026 | B2 | 8/2003 | Cragg et al. |
| 6,616,652 | B1 | 9/2003 | Harper |
| 6,641,800 | B1 | 11/2003 | Mistry et al. |
| 6,689,108 | B2 | 2/2004 | Lavi et al. |
| 6,716,190 | B1 | 4/2004 | Glines et al. |
| 6,723,067 | B2 | 4/2004 | Nielson |
| 6,811,550 | B2 | 11/2004 | Holland et al. |
| 6,843,388 | B1 | 1/2005 | Hollars |
| 6,863,660 | B2 | 3/2005 | Marx |
| 6,905,475 | B2 | 6/2005 | Hauschild et al. |
| 6,913,596 | B2 | 7/2005 | Davey |
| 6,939,324 | B2 | 9/2005 | Gonnelli et al. |
| 7,101,862 | B2 | 9/2006 | Chochrum et al. |
| 7,156,880 | B2 | 1/2007 | Evans et al. |
| 7,178,744 | B2 | 2/2007 | Tapphorn et al. |
| 7,182,748 | B1 | 2/2007 | Potter et al. |
| 7,291,133 | B1 | 11/2007 | Kindler et al. |
| 7,334,598 | B1 | 2/2008 | Hollars |
| 7,455,248 | B2 | 11/2008 | Kablik et al. |
| 7,534,449 | B2 | 5/2009 | Saltzman et al. |
| 7,544,177 | B2 | 6/2009 | Gertner |
| 7,547,292 | B2 | 6/2009 | Sheldrake |
| 7,588,171 | B2 | 9/2009 | Reedy et al. |
| 7,632,245 | B1 | 12/2009 | Cowan et al. |
| 7,648,083 | B2 | 1/2010 | Hornsby et al. |
| 7,673,783 | B2 | 3/2010 | Morgan et al. |
| 7,691,244 | B2 | 4/2010 | Levitan et al. |
| 7,744,526 | B2 | 6/2010 | McAlister et al. |
| 7,776,822 | B2 | 8/2010 | Terman |
| 7,824,373 | B2 | 11/2010 | Kim |
| 7,857,167 | B1 | 12/2010 | Hollars |
| 7,914,517 | B2 | 3/2011 | Baran et al. |
| 8,083,721 | B2 | 12/2011 | Miller |
| 8,109,872 | B2 | 2/2012 | Kennedy, II et al. |
| 8,118,772 | B2 | 2/2012 | Ducharme |
| 8,118,777 | B2 | 2/2012 | Ducharme et al. |
| 8,210,449 | B2 | 7/2012 | Peterson et al. |
| 8,235,937 | B2 | 8/2012 | Palasis et al. |
| 8,292,197 | B2 | 10/2012 | Ballu et al. |
| 8,298,175 | B2 | 10/2012 | Hirschel et al. |
| RE43,824 | E | 11/2012 | Sheldrake et al. |
| 8,361,054 | B2 | 1/2013 | Ducharme et al. |
| 8,372,092 | B2 | 2/2013 | Gabel et al. |
| 8,418,775 | B2 | 4/2013 | Blomet et al. |
| 8,523,821 | B2 | 9/2013 | Miller |
| 8,721,582 | B2 | 5/2014 | Ji |
| 8,728,032 | B2 | 5/2014 | Ducharme et al. |
| 8,827,980 | B2 | 9/2014 | Ji |
| 8,944,296 | B2 | 2/2015 | Vogt et al. |
| 8,950,396 | B2 | 2/2015 | Wachtel et al. |
| 9,101,744 | B2 | 8/2015 | Ducharme |
| 9,205,207 | B2 | 12/2015 | Ji |
| 9,205,240 | B2 | 12/2015 | Greenhalgh et al. |
| 9,375,533 | B2 | 6/2016 | Ducharme et al. |
| 9,393,583 | B2 | 7/2016 | Tu |
| 9,474,915 | B2 | 10/2016 | Gonzales et al. |
| 9,486,609 | B2 | 11/2016 | Ross |
| 9,555,185 | B2 | 1/2017 | Foster et al. |
| 9,629,966 | B2 | 4/2017 | Ji |
| 9,837,931 | B2 | 12/2017 | Luo et al. |
| 9,839,772 | B2 | 12/2017 | Ducharme |
| 9,867,931 | B2 | 1/2018 | Gittard |
| 9,895,527 | B2 | 2/2018 | Spohn et al. |
| 9,907,456 | B2 | 3/2018 | Miyoshi |
| 10,463,811 | B2 | 11/2019 | Lee et al. |
| 10,542,868 | B2 | 1/2020 | Gordon et al. |
| 10,610,665 | B2 | 4/2020 | Krueger et al. |
| 10,806,853 | B2 | 10/2020 | Gittard |
| 10,842,368 | B2 | 11/2020 | Nave |
| 10,994,110 | B2 | 5/2021 | Ducharme |
| 11,344,314 | B2 | 5/2022 | Tal et al. |
| 11,766,546 | B2 | 9/2023 | Pic et al. |
| 2001/0056256 | A1 | 12/2001 | Hughes et al. |
| 2002/0165483 | A1 | 11/2002 | Miller |
| 2002/0169416 | A1 | 11/2002 | Gonnelli |
| 2003/0023202 | A1 | 1/2003 | Nielson et al. |
| 2003/0032862 | A1 | 2/2003 | Ota et al. |
| 2003/0069549 | A1 | 4/2003 | Macmahon |
| 2003/0108511 | A1 | 6/2003 | Sawhney |
| 2003/0170250 | A1 | 9/2003 | Ezrin et al. |
| 2003/0181917 | A1 | 9/2003 | Gertner |
| 2003/0216695 | A1 | 11/2003 | Yang |
| 2004/0059283 | A1 | 3/2004 | Kirwan et al. |
| 2004/0073863 | A1 | 4/2004 | Mousley |
| 2004/0215135 | A1 | 10/2004 | Sheldrake et al. |
| 2004/0262340 | A1 | 12/2004 | Kress |
| 2005/0070848 | A1 | 3/2005 | Kim et al. |
| 2005/0125002 | A1 | 6/2005 | Baran et al. |
| 2005/0205087 | A1 | 9/2005 | Kablik et al. |
| 2006/0002852 | A1 | 1/2006 | Saltzman et al. |
| 2006/0052295 | A1 | 3/2006 | Terman |
| 2006/0100572 | A1 | 5/2006 | DiMatteo et al. |
| 2006/0252993 | A1 | 11/2006 | Freed |
| 2006/0286640 | A1 | 12/2006 | Ono |
| 2007/0005002 | A1 | 1/2007 | Millman |
| 2007/0088317 | A1 | 4/2007 | Hyde |
| 2007/0199824 | A1 | 8/2007 | Hoerr et al. |
| 2007/0240989 | A1 | 10/2007 | Levitan et al. |
| 2007/0241119 | A1 | 10/2007 | Durkin et al. |
| 2008/0021374 | A1 | 1/2008 | Kawata |

(56) References Cited

U.S. PATENT DOCUMENTS

| | | | |
|---|---|---|---|
| 2008/0027272 | A1 | 1/2008 | Kadykowski |
| 2008/0120992 | A1 | 5/2008 | Levy et al. |
| 2008/0132891 | A1 | 6/2008 | Nobis et al. |
| 2008/0287911 | A1 | 11/2008 | El-Nounou et al. |
| 2009/0000615 | A1 | 1/2009 | Pohlmann |
| 2009/0007904 | A1 | 1/2009 | Schuster et al. |
| 2009/0030274 | A1 | 1/2009 | Goldfarb et al. |
| 2009/0071470 | A1 | 3/2009 | Abrams |
| 2009/0145982 | A1 | 6/2009 | Blomet et al. |
| 2009/0155342 | A1 | 6/2009 | Diegelmann et al. |
| 2009/0234227 | A1 | 9/2009 | Punga |
| 2009/0234374 | A1 | 9/2009 | Gabel et al. |
| 2009/0234380 | A1 | 9/2009 | Gabel et al. |
| 2009/0240197 | A1 | 9/2009 | Cowan et al. |
| 2009/0248056 | A1 | 10/2009 | Gabel et al. |
| 2009/0281486 | A1 | 11/2009 | Ducharme |
| 2009/0326453 | A1 | 12/2009 | Adams et al. |
| 2010/0101579 | A1 | 4/2010 | Levy et al. |
| 2010/0121261 | A1 | 5/2010 | Kablik et al. |
| 2010/0137796 | A1 | 6/2010 | Perry et al. |
| 2010/0160897 | A1 | 6/2010 | Ducharme et al. |
| 2010/0191185 | A1 | 7/2010 | Miller |
| 2010/0305505 | A1 | 12/2010 | Ducharme et al. |
| 2011/0178495 | A1 | 7/2011 | Ji |
| 2011/0272438 | A1 | 11/2011 | Vogt et al. |
| 2012/0116296 | A1 | 5/2012 | Ducharme et al. |
| 2012/0136301 | A1 | 5/2012 | Miller |
| 2012/0238965 | A1 | 9/2012 | Chang |
| 2013/0046278 | A1 | 2/2013 | Ji |
| 2013/0059113 | A1 | 3/2013 | Hatton et al. |
| 2013/0100801 | A1 | 4/2013 | Allan et al. |
| 2013/0104884 | A1 | 5/2013 | Vazales et al. |
| 2013/0110080 | A1 | 5/2013 | Ducharme |
| 2014/0200402 | A1 | 7/2014 | Snoke et al. |
| 2014/0207097 | A1 | 7/2014 | Ji |
| 2014/0248437 | A1 | 9/2014 | Schroeder et al. |
| 2014/0271491 | A1 | 9/2014 | Gittard et al. |
| 2014/0296806 | A1 | 10/2014 | Williams et al. |
| 2014/0346257 | A1 | 11/2014 | Reetz, III et al. |
| 2015/0216516 | A1 | 8/2015 | Steffen |
| 2015/0265784 | A1 * | 9/2015 | Lampert ............ A61B 1/00006 604/26 |
| 2015/0306317 | A1 | 10/2015 | Ducharme et al. |
| 2017/0224762 | A1 | 8/2017 | McIntosh et al. |
| 2017/0232141 | A1 | 8/2017 | Surti et al. |
| 2017/0265879 | A1 | 9/2017 | Washburn, II et al. |
| 2017/0296221 | A1 | 10/2017 | DiCaprio et al. |
| 2018/0001067 | A1 | 1/2018 | Christakis et al. |
| 2018/0056052 | A1 | 3/2018 | Swanson et al. |
| 2018/0099088 | A1 | 4/2018 | Gittard |
| 2018/0161526 | A1 | 6/2018 | Canner et al. |
| 2018/0193011 | A1 | 7/2018 | Keene et al. |
| 2018/0193574 | A1 | 7/2018 | Smith et al. |
| 2018/0221296 | A1 | 8/2018 | Holekamp et al. |
| 2018/0344659 | A1 | 12/2018 | Holekamp et al. |
| 2019/0008601 | A1 | 1/2019 | Pereira et al. |
| 2019/0232030 | A1 | 8/2019 | Pic et al. |
| 2019/0308213 | A1 | 10/2019 | Mispel-Beyer |
| 2019/0322442 | A1 | 10/2019 | Thomsen |
| 2019/0343980 | A1 | 11/2019 | Gittard et al. |
| 2019/0351207 | A1 | 11/2019 | Quan et al. |
| 2019/0388665 | A1 | 12/2019 | Christakis et al. |
| 2020/0046213 | A1 | 2/2020 | Bendory et al. |
| 2020/0060536 | A1 | 2/2020 | Rylander et al. |
| 2020/0061310 | A1 | 2/2020 | Goodman et al. |
| 2020/0100986 | A1 * | 4/2020 | Pic ........................ B05B 7/1413 |
| 2020/0101476 | A1 | 4/2020 | Pic et al. |
| 2020/0222218 | A1 | 7/2020 | Poulsen et al. |
| 2020/0397983 | A1 | 12/2020 | Gittard |
| 2021/0022761 | A1 | 1/2021 | Looper et al. |
| 2021/0106717 | A1 | 4/2021 | Gittard et al. |
| 2021/0161515 | A1 | 6/2021 | Pic et al. |
| 2021/0162122 | A1 | 6/2021 | Pic et al. |
| 2021/0187190 | A1 | 6/2021 | Congdon et al. |
| 2021/0228852 | A1 | 7/2021 | Ducharme |
| 2021/0275760 | A1 | 9/2021 | Hunter et al. |
| 2021/0299400 | A1 | 9/2021 | Cauche et al. |
| 2021/0346568 | A1 | 11/2021 | Gittard et al. |
| 2021/0379302 | A1 | 12/2021 | Sigmon et al. |
| 2022/0040006 | A1 | 2/2022 | Surti et al. |
| 2023/0016512 | A1 | 1/2023 | Slattery et al. |
| 2023/0390540 | A1 | 12/2023 | Pic et al. |

FOREIGN PATENT DOCUMENTS

| | | | |
|---|---|---|---|
| AU | 2009330505 | | 6/2011 |
| AU | 2011202035 | | 11/2011 |
| AU | 2010253997 | | 12/2011 |
| AU | 2014237970 | | 9/2015 |
| AU | 2014329827 | | 4/2016 |
| BR | 112022023464.3 | | 12/2022 |
| CA | 2194096 | | 8/2005 |
| CA | 2723183 | | 11/2009 |
| CA | 2747390 | | 7/2010 |
| CA | 2751538 | | 8/2010 |
| CA | 2763135 | | 12/2010 |
| CA | 2585845 | | 12/2012 |
| CA | 2925900 | | 4/2015 |
| CA | 2737832 | | 2/2016 |
| CN | 101820935 | A | 9/2010 |
| CN | 105050630 | A | 11/2015 |
| CN | 105792869 | A | 7/2016 |
| CN | 206482553 | U | 9/2017 |
| CN | 209137722 | U | 7/2019 |
| CN | 110691615 | A | 1/2020 |
| CN | 112546336 | A | 3/2021 |
| CN | 113080819 | A | 7/2021 |
| CN | 114514017 | A | 5/2022 |
| CN | 115697176 | A | 2/2023 |
| DE | 3024749 | A1 | 2/1982 |
| DE | 3108918 | A1 | 9/1982 |
| DE | 3613762 | A1 | 11/1987 |
| DE | 69529495 | | 3/2003 |
| DE | 69530843 | | 6/2003 |
| DE | 10 2004 011 444 | A1 | 9/2005 |
| DE | 60210063 | | 5/2006 |
| DE | 602005005081 | | 4/2008 |
| DE | 102010019222 | | 11/2013 |
| EP | 308269 | A1 | 3/1989 |
| EP | 0692273 | A1 | 1/1996 |
| EP | 0738498 | A1 | 10/1996 |
| EP | 0690732 | | 1/2003 |
| EP | 0767624 | | 5/2003 |
| EP | 1293559 | | 7/2005 |
| EP | 1550713 | | 7/2005 |
| EP | 1365824 | B1 | 3/2006 |
| EP | 1804926 | | 2/2008 |
| EP | 2277577 | A1 | 1/2011 |
| EP | 2384871 | | 11/2011 |
| EP | 2391411 | | 12/2011 |
| EP | 2435114 | | 4/2012 |
| EP | 2680912 | | 8/2015 |
| EP | 2934629 | | 10/2015 |
| EP | 2968651 | | 1/2016 |
| EP | 3052168 | | 5/2017 |
| EP | 3150240 | | 5/2017 |
| EP | 3190981 | A1 | 7/2017 |
| EP | 3190981 | B1 | 7/2017 |
| EP | 2375960 | | 10/2018 |
| EP | 3615094 | A1 | 3/2020 |
| EP | 4041196 | | 8/2022 |
| EP | 4161346 | | 4/2023 |
| FR | 2863503 | A1 | 6/2005 |
| FR | 2877240 | | 1/2007 |
| GB | 189610563 | A | 12/1896 |
| GB | 1254534 | A | 11/1971 |
| GB | 2300371 | A | 11/1996 |
| GB | 0100756 | | 3/2001 |
| JP | S5667464 | A | 6/1981 |
| JP | 4022109 | B | 4/1992 |
| JP | H05192404 | A | 8/1993 |
| JP | H08206229 | A | 8/1996 |
| JP | 1997-253032 | | 9/1997 |
| JP | 10505253 | | 5/1998 |

(56) References Cited

FOREIGN PATENT DOCUMENTS

| | | | |
|---|---|---|---|
| JP | H10508790 | A | 9/1998 |
| JP | 2002028224 | A | 1/2002 |
| JP | 2003/024833 | A | 1/2003 |
| JP | 2003-126026 | | 5/2003 |
| JP | 2004/521677 | | 7/2004 |
| JP | 2004-535246 | | 11/2004 |
| JP | 2005270372 | A | 10/2005 |
| JP | 3719608 | | 11/2005 |
| JP | 2007529280 | A | 10/2007 |
| JP | 2009-530051 | | 8/2009 |
| JP | 2011/508588 | | 3/2011 |
| JP | 2011519679 | A | 7/2011 |
| JP | 2011/235962 | | 11/2011 |
| JP | 2012/513284 | | 6/2012 |
| JP | 5502801 | | 5/2014 |
| JP | 5631332 | | 11/2014 |
| JP | 5670439 | | 12/2014 |
| JP | 2016/512069 | A | 4/2016 |
| JP | 6047546 | | 11/2016 |
| JP | 6552115 | | 7/2019 |
| JP | 2020/517399 | | 6/2020 |
| JP | 6715274 | B2 | 7/2020 |
| JP | 6807742 | | 12/2020 |
| JP | 2020 023110 | | 2/2022 |
| JP | 2022/521497 | A | 4/2022 |
| JP | 2022-551509 | | 9/2022 |
| KR | 20170055300 | A | 5/2017 |
| KR | 102387327 | | 4/2022 |
| KR | 10-2023-0002873 | | 5/2023 |
| SU | 978999 | A2 | 12/1982 |
| TW | 1719844 | B | 2/2021 |
| WO | 1982003545 | A1 | 10/1982 |
| WO | 1985002346 | A1 | 6/1985 |
| WO | 1992020312 | A1 | 11/1992 |
| WO | 1994028798 | A1 | 12/1994 |
| WO | WO 1995/19799 | | 7/1995 |
| WO | 1996009085 | A1 | 3/1996 |
| WO | 1996025190 | A1 | 8/1996 |
| WO | 1996037245 | A1 | 11/1996 |
| WO | WO 1996/00524 | | 11/1996 |
| WO | 1996040327 | A1 | 12/1996 |
| WO | 1997020585 | A1 | 6/1997 |
| WO | WO 1999/12595 | | 3/1999 |
| WO | 1999021599 | A1 | 5/1999 |
| WO | WO 02/055139 | | 7/2002 |
| WO | WO2002/053014 | | 7/2002 |
| WO | WO 2003/007797 | A1 | 1/2003 |
| WO | 2004002551 | A2 | 1/2004 |
| WO | WO2004/073863 | | 9/2004 |
| WO | 2005089472 | | 9/2005 |
| WO | 2005100980 | A2 | 10/2005 |
| WO | WO 2006/048536 | | 5/2006 |
| WO | 2006090149 | A2 | 8/2006 |
| WO | WO 2007/112185 | A1 | 10/2007 |
| WO | 2008008845 | A2 | 1/2008 |
| WO | 2008023545 | A1 | 2/2008 |
| WO | WO 2009/088576 | | 7/2009 |
| WO | WO2009/091549 | | 7/2009 |
| WO | WO 2009/137438 | | 11/2009 |
| WO | WO2009/137438 | A2 | 11/2009 |
| WO | WO 2010//074949 | | 7/2010 |
| WO | WO 2010/088146 | | 8/2010 |
| WO | WO 2010/138703 | | 12/2010 |
| WO | WO 2012/118466 | | 9/2012 |
| WO | 2013093798 | A1 | 6/2013 |
| WO | WO 2014/099662 | | 6/2014 |
| WO | WO 2014/149617 | | 9/2014 |
| WO | WO 2015/050814 | | 4/2015 |
| WO | WO2016/038593 | A1 | 3/2016 |
| WO | WO 2016/111373 | | 7/2016 |
| WO | WO 2017/006684 | | 1/2017 |
| WO | WO 2017/028701 | A1 | 2/2017 |
| WO | WO 2018/200695 | | 1/2018 |
| WO | WO2018/200695 | A1 | 11/2018 |
| WO | WO 2020/254447 | | 12/2020 |
| WO | WO 2021/071751 | | 4/2021 |
| WO | WO2021/071751 | A1 | 4/2021 |
| WO | WO 2021/141791 | A1 | 7/2021 |
| WO | WO 2021/247850 | | 12/2021 |
| WO | WO2023/287654 | A1 | 1/2023 |
| WO | WO 2023/076076 | A1 | 5/2023 |

OTHER PUBLICATIONS

Office Action in Japanese Patent Application No. 2022-570158, dated Nov. 17, 2023 (9 pages).

Machine Translation of JP 1997-253032 (21 pages).

Partial European Search Report in EP Application No. 23204400.8, dated Mar. 18, 2024 (17 pages).

PCT International Search Report in related Application No. PCT/US2022/036498 dated Oct. 27, 2022 (15 pages).

Hemospray® Endoscopic Hemostat: https://www.cookmedical.com/products/35a4a7f2-867b-4c81-a983-44ea06277852/; 5 pages, date downloaded Sep. 30, 2020.

Cardinal IP Services, “Prevention of Spray Activation During System Closure” (DN-9175) Patentability Search of Disclosure, 13 pages, dated Sep. 30, 2020.

Cardinal IP Services, “Water Ingress Prevention Via Positive (Active/Passive) Air Flow” (DN-9171 and DN-9184) Patentability Search of Disclosure, 15 pages, dated Jan. 13, 2021.

Cardinal IP Services, “Preventing Accidental Powder Deployment” (DN-9387) Patentability Search of Disclosure, 9 pages, dated Nov. 9, 2021.

Cardinal IP Services, “Positive Pressure Delivery Mechanism for a Therapeutic Agent Delivery Device” (DN-9347) Patentability Search of Disclosure, 13 pages, dated Oct. 12, 2021.

Cardinal IP Services, “Catheter Distal End Features to Prevent Lens Irrigation Fluid Ingress” (DN-9378) Patentability Search of Disclosure, 16 pages, dated Nov. 5, 2021.

Cardinal IP Services, “Device That Allows For Cleaning of Catheter and Camera Lens on Endoscope Distal Tip” (DN-9495) Patentability Search of Disclosure, 11 pages, dated Jan. 3, 2022.

Partial European Search Report in EP Application No. 23214435.2, dated Apr. 23, 2024 (14 pages).

Medgadget, *Convesaid, A Hemostat Powder Spray That Can’t Cause Embolisms*, (Team Consulting) Mar. 16, 2018 (4 pages).

International Preliminary Report on Patentability in PCT Application No. PCT/US2022/047013, dated Apr. 30, 2024 (12 pages).

Australian Patent Office. Examination Report No. 1 for AU Application No. 2022379451, mailed Dec. 5, 2024, pp. 1-3.

Japanese Patent Office. Notice of Reasons for Refusal for JP Application No. 2021-568931 and English translation, mailed Mar. 11, 2025, pp. 1-12.

Alto Shooter Catalog, Kaigen, English and Japanese, Jun. 1994, 8 pgs.

Decker, “An Efficient Method For The Application Of Avitene Hemostatic Agent”, Surgery, Gynecology & Obstetrics, 1991, vol. 172, No. 6, 2 pgs.

Endo-Avitene™ Brochure “Microfibrillar Collagen Hemostat in an Endoscopic Delivery System”, from MedChem Products, 4 pgs, 1992.

Fagelman, et al. “A Simple Method For Application Of Microfibrillar Collagen”, Surgery, Gynecology & Obstetrics, Jun. 1980, vol. 150, No. 6, 3 pgs.

Fritscher-Ravens et al., “Beyond Notes: randomized controlled study of different methods of flexible endoscopic hemostasis of artificially induced hemorrhage, via Notes access to the peritoneal cavity”, Endoscopy 2009, vol. 41, pp. 29-35.

Hoshino, “Transendoscopic Projectile Drug Delivery”, The Japanese Society of Gastroenterology, vol. 25, No. 5, 1990, 1 page.

Hoshino, et al. “Trans-endoscopic Drug Propulsion Therapy”, Digestive Endoscopy, 1993, vol. 5, 6 pgs.

J. Chadwick, Particle Size Control in Aerosol Packages, Spray Technology & Marketing, Dec. 2004, Aerosol Technical Solutions, p. 1-3.

Park et al., “A randomized comparison of a new flexible bipolar hemostasis forceps designed principally for Notes versus a conventional surgical laparoscopic bipolar forceps for intra-abdominal

(56) References Cited

OTHER PUBLICATIONS vessel sealing in a porcine model", Gastrointestinal Endoscopy 2010, vol. 71, No. 4, pp. 835-841.
Surgical Armamentarium, Copyright 1973 V. Mueller, 3 pgs.
Wong Kee Song, L.-M. et al., "Emerging technologies for endoscopic hemostasis", Gastrointest. Endosc., vol. 75, No. 5, May 2012: pp. 933-937.
Korean Intellectual Property Office. Notice of Preliminary Rejection for KR Application No. 10-2024-7013863 and English translation, mailed Feb. 20, 2026, pp. 1-18.

* cited by examiner

SYSTEMS AND METHODS FOR DELIVERING PRESSURIZED FLUID TO A TARGET SITE ALONE OR IN CONJUNCTION WITH THERAPEUTIC AGENTS

CROSS-REFERENCE TO RELATED APPLICATIONS

This application claims priority from U.S. Provisional Application No. 63/271,556, filed Oct. 25, 2021, the entirety of which is hereby fully incorporated by reference herein.

BACKGROUND

The present embodiments relate generally to medical devices, and more particularly, to medical devices for delivering therapeutic agents to a target site.

There are several instances in which it may become desirable to introduce therapeutic agents into the human or animal body. For example, therapeutic drugs or bioactive materials may be introduced to achieve a biological effect. The biological effect may include an array of targeted results, such as inducing hemostasis, sealing perforations, reducing restenosis likelihood, or treating cancerous tumors or other diseases.

Many of such therapeutic agents are injected using an intravenous (IV) technique and via oral medicine. While such techniques permit the general introduction of medicine, in many instances it may be desirable to provide localized or targeted delivery of therapeutic agents, which may allow for the guided and precise delivery of agents to selected target sites. For example, localized delivery of therapeutic agents to a tumor may reduce the exposure of the therapeutic agents to normal, healthy tissues, which may reduce potentially harmful side effects.

Localized delivery of therapeutic agents has been performed using catheters and similar introducer devices. By way of example, a catheter may be advanced towards a target site within the patient, then the therapeutic agent may be injected through a lumen of the catheter to the target site. Typically, a syringe or similar device may be used to inject the therapeutic agent into the lumen of the catheter. However, such a delivery technique may result in a relatively weak stream of the injected therapeutic agent.

Moreover, it may be difficult or impossible to deliver therapeutic agents in a targeted manner in certain forms, such as a powder form, to a desired site. For example, if a therapeutic powder is held within a syringe or other container, it may not be easily delivered through a catheter to a target site in a localized manner that may also reduce potentially harmful side effects.

SUMMARY

One general aspect of the present disclosure includes a system suitable for delivering a therapeutic agent to a target site, the system including: a container for holding a therapeutic agent; a pressure source having pressurized fluid, the pressure source in selective fluid communication with at least a portion of the container; a catheter in selective fluid communication with the container and configured for delivery of the therapeutic agent or the pressurized fluid to a target site; and a housing configured to securely retain the container and movably support a switch, where the switch is movable between a first position and a second position, where when the switch is in the first position, delivery of the therapeutic agent is prevented while delivery of the pressurized fluid is permitted, and where when the switch is in the second position, delivery of the therapeutic agent is permitted.

Another general aspect of the present disclosure includes a method suitable for delivering a therapeutic agent to a target site, the method including: actuating a pressure source having pressurized fluid, the pressure source in selective fluid communication with at least a portion of a container that holds a therapeutic agent; depressing a button to actuate a first valve such that the pressurized fluid flows through the first valve and into a catheter absent delivery of the therapeutic agent, the first valve being connected between the pressure source and the container, and the catheter in selective fluid communication with the container and configured for delivery of the pressurized fluid or the therapeutic agent to a target site; and moving a switch from a first position to a second position such that the button can be further depressed to actuate the first valve to allow the pressurized fluid to flow through the first valve and into the container, the switch being movably supported by a housing that securely retains the container.

Another general aspect of the present disclosure includes a system suitable for delivering a therapeutic agent to a target site, the system including: a container for holding a therapeutic agent; a pressure source having pressurized fluid, the pressure source in selective fluid communication with at least a portion of the container; a catheter in selective fluid communication with the container and configured for delivery of the therapeutic agent or the pressurized fluid to a target site; and a housing configured to securely retain the container and movably support a switch, where the switch includes a snappable portion and is movable between a first position and a second position after the snappable portion is snapped off, where when the switch is in the first position, delivery of the therapeutic agent is prevented while delivery of the pressurized fluid is permitted, and where when the switch is moved to the second position, the snappable portion is snapped off such that when the switch is in the second position, delivery of the therapeutic agent is permitted.

Another general aspect of the present disclosure includes a valve, the valve including: a main body including a proximal end, a distal end, and an inner lumen extending between the proximal end and the distal end, where the main body includes an inlet port, a first outlet port, and a second outlet port; and a piston slidably movable along a length of the inner lumen of the main body, where the piston includes spaced apart first and second openings disposed on an outer surface of the piston, and where the first and second openings are connected by a bridge extending through the piston at an angle with respect to a length of the piston.

Another general aspect of the present disclosure includes a valve, the valve including: a main body including a proximal end, a distal end, and an inner lumen extending between the proximal end and the distal end, where the main body includes an inlet port, a first outlet port, and a second outlet port; and a piston slidably movable along a length of the inner lumen of the main body, where the piston includes spaced apart first and second grooves connected by a bridge extending along a length of the piston, where the first groove extends through the piston radially along a diameter of a first cross section of the piston, and where the second groove extends through the piston radially along a diameter of a second cross section of the piston.

Another general aspect of the present disclosure includes a method of operating a valve, where the valve includes a main body including a proximal end, a distal end, and an inner lumen extending between the proximal end and the distal end, where the main body includes an inlet port, a first outlet port, and a second outlet port; and a piston slidably movable along a length of the inner lumen of the main body, where the piston includes a bridge extending through at least a portion of the piston, the method including: moving the piston such that a first fluid communication is established between the inlet port and the first outlet port via the bridge; and moving the piston such that a second fluid communication is established between the inlet port and the second outlet port via the bridge.

A system suitable for delivering a therapeutic agent to a target site or a valve according to the present disclosure may include any combination of the features described above and/or the original as-filed claims.

Other systems, methods, features and advantages of the invention will be, or will become, apparent to one with skill in the art upon examination of the following figures and detailed description. It is intended that all such additional systems, methods, features and advantages be within the scope of the invention.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENT

Figure 1:
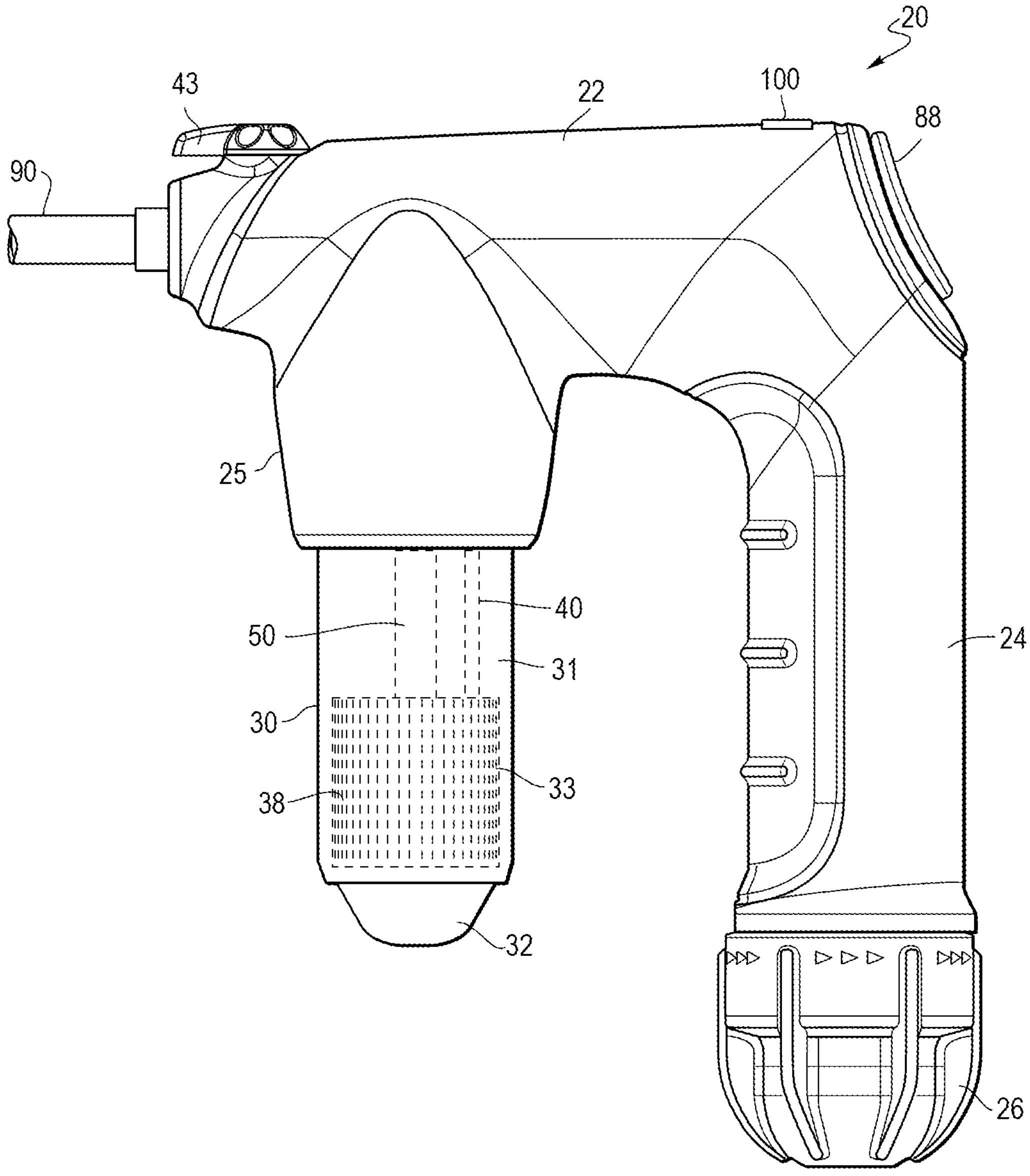
FIG. 1 is a perspective view of a system for delivering therapeutic agents in accordance with an embodiment, showing a housing, a front valve (second valve), a switch, and a button.

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale (although certain drawings may be drawn to scale and relied upon as such), and in certain instances details may have been omitted that are not necessary for an understanding of aspects disclosed herein, such as conventional material, construction, and assembly.

For purposes of promoting an understanding of the presently disclosed embodiments, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the present application, the term “proximal” refers to a direction that is generally towards a physician during a medical procedure, while the term “distal” refers to a direction that is generally towards a target site within a patient’s anatomy during a medical procedure. The term “configured to” is used to describe structural limitations in a particular manner that requires specific construction to accomplish a stated function and/or to interface or interact with another component(s), and is not used to describe mere intended or theoretical uses. Relative terminology and broader terms such as “generally,” “about,” “substantially,” and the like will be understood by those of skill in the art as providing clear and definite scope of disclosure and/or claiming. For example, the term “about 4-6 N” will be understood as not requiring exactly 4-6 N, but rather including that and functional equivalents.

Referring now to FIGS. 1-18, an embodiment of a system 20 suitable for delivering one or more therapeutic agents to a target site is shown. In this embodiment, the system 20 comprises a container 30 that is configured to hold a therapeutic agent 38, at least one pressure source 68 having pressurized fluid, which is configured to be placed in selective fluid communication with at least a portion of the container 30, and a catheter 90 that is configured to be placed in selective fluid communication with the container 30 and to deliver the therapeutic agent 38 or the pressurized fluid through the catheter 90 to a target site within the patient, as explained more fully below.

Figure 2A:
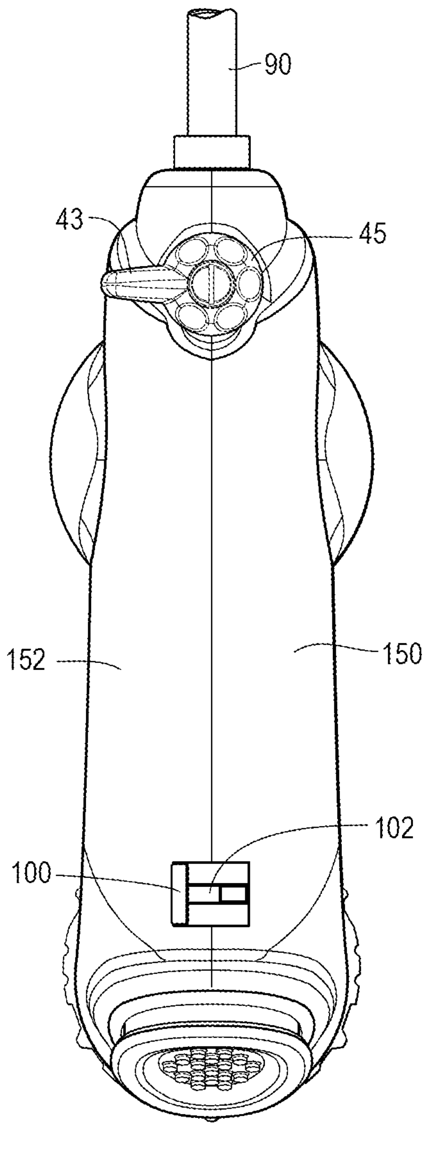
FIG. 2A is another perspective view of the system of FIG. 1, showing the front valve in a first state, the switch in a first position, and the button in a default state.
Figure 2B:
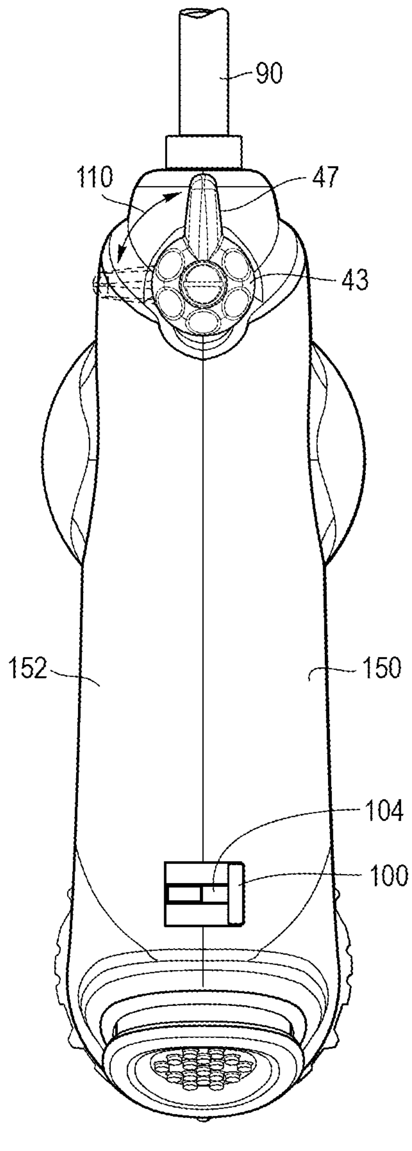
FIG. 2B is another perspective view of the system of FIG. 1, showing the front valve in a second state, the switch in a second position, and the button in the default state.

The system 20 further comprises a housing 22, which is suitable for securely retaining, holding, engaging and/or covering the container 30, pressure source 68, catheter 90, and other components described below. Preferably, the housing 22 comprises an upright section 24 that may be grasped by a user and a section 25 that acts as a housing for the container 30. The housing 22 is also configured to movably support a switch 100, where the switch 100 is movable between a first position 102 (e.g., as shown in FIG. 2A) and a second position 104 (e.g., as shown in FIG. 2B). The system 20 is configured such that when the switch 100 is in the first position 102, delivery of the therapeutic agent 38 is prevented while delivery of the pressurized fluid is permitted, and when the switch 100 is in the second position 104, delivery of the therapeutic agent 38 is permitted, as described in greater detail below. An actuator 26 may be engaged by a user prior to delivering the pressurized fluid without the therapeutic agent or delivering the therapeutic agent.

Figure 4:
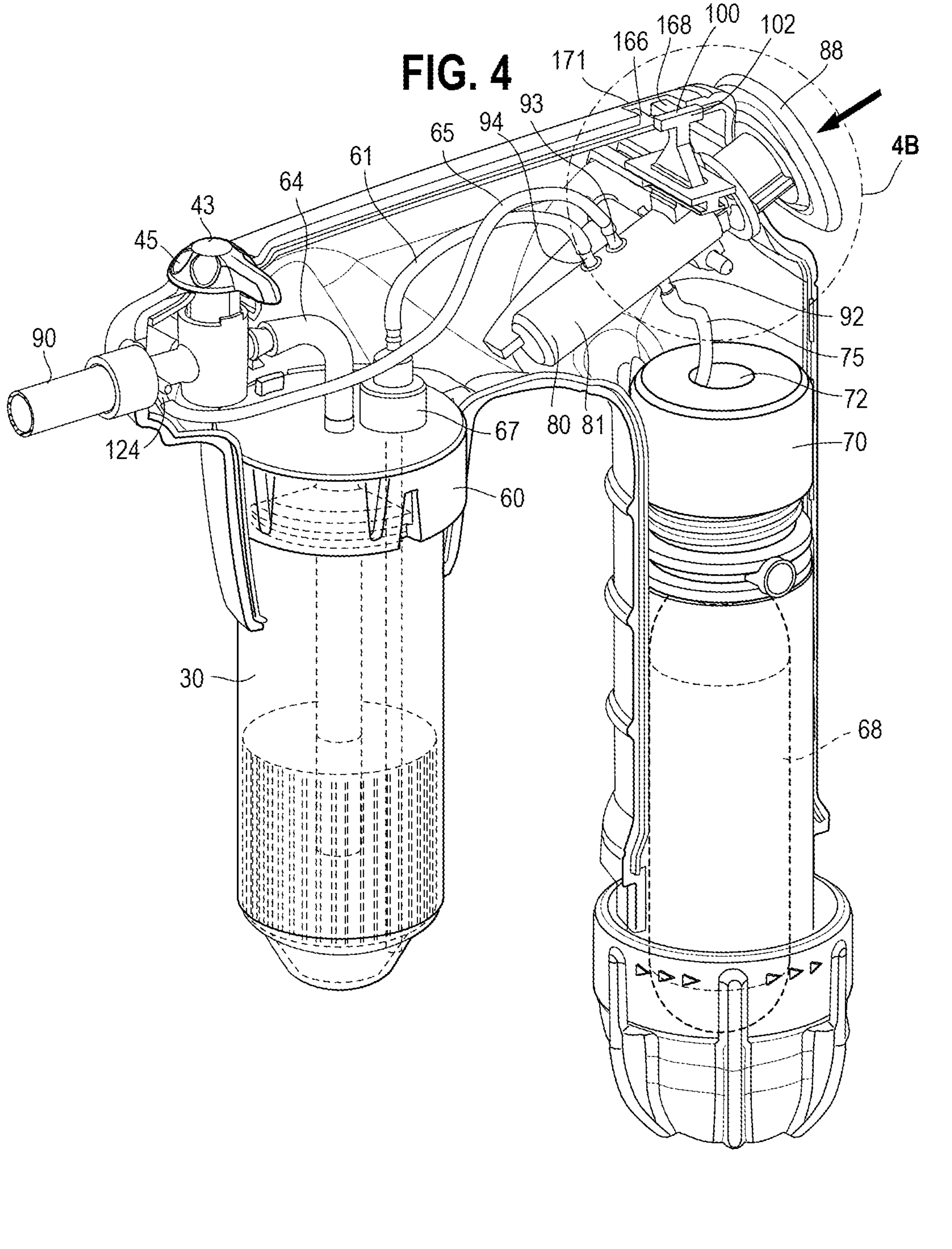
FIG. 4 is another perspective view of the system of FIG. 1 with a portion of the housing removed, showing the front valve in the first state, the switch in the first position, and the button depressed.
Figure 5:
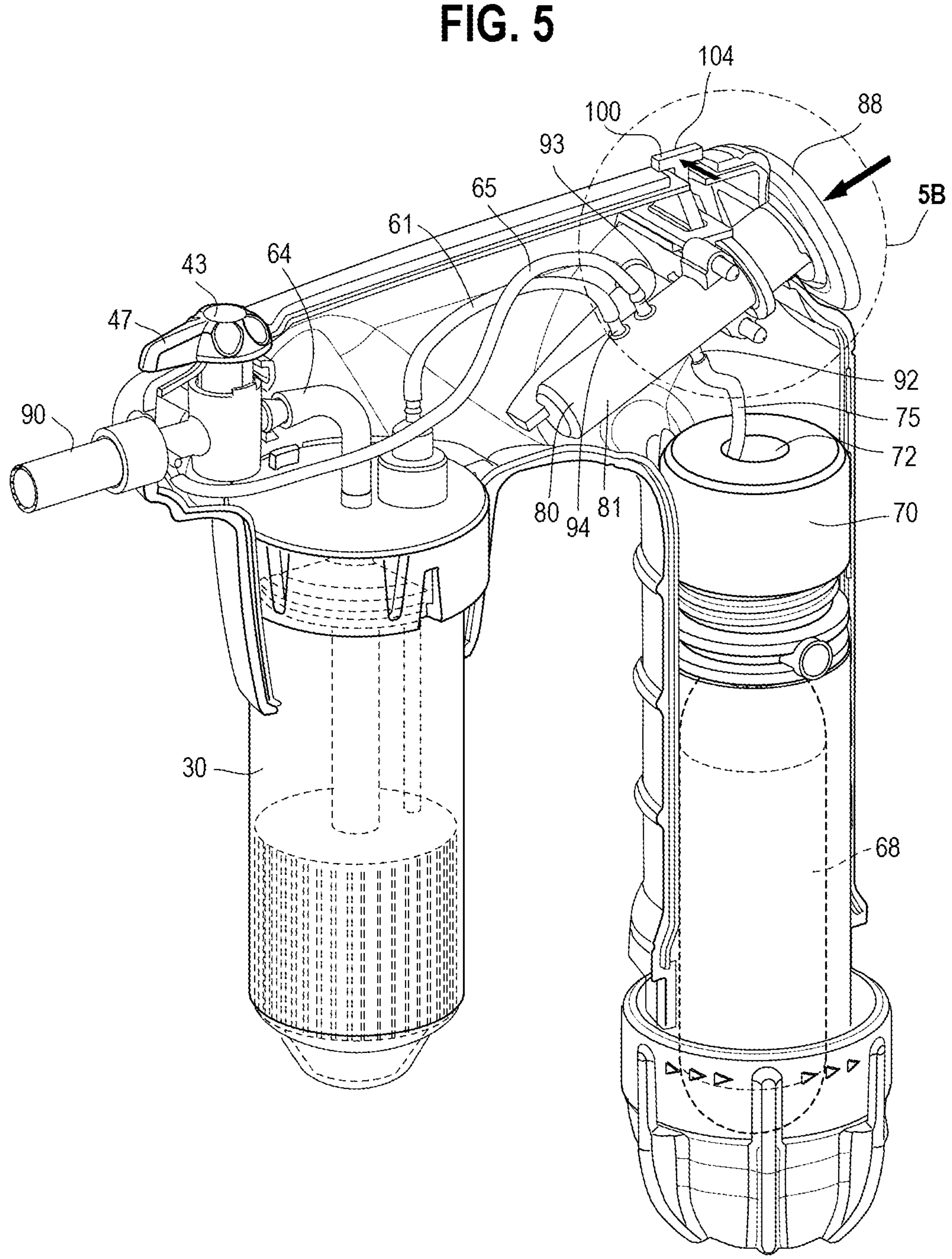
FIG. 5 is another perspective view of the system of FIG. 4, showing the front valve in a second state, the switch in a second position, and the button depressed.

The system 20 further comprises a first valve 80 (e.g., as shown in FIGS. 4 and 5) configured to be connected between the pressure source 68 and the container 30, a second valve 43 configured to be connected between the container 30 and the catheter 90, and a button 88 configured to selectively actuate the first valve 80 to deliver the pressurized fluid without the therapeutic agent 38 or to deliver the therapeutic agent 38, as described in greater detail below.

Figure 3:
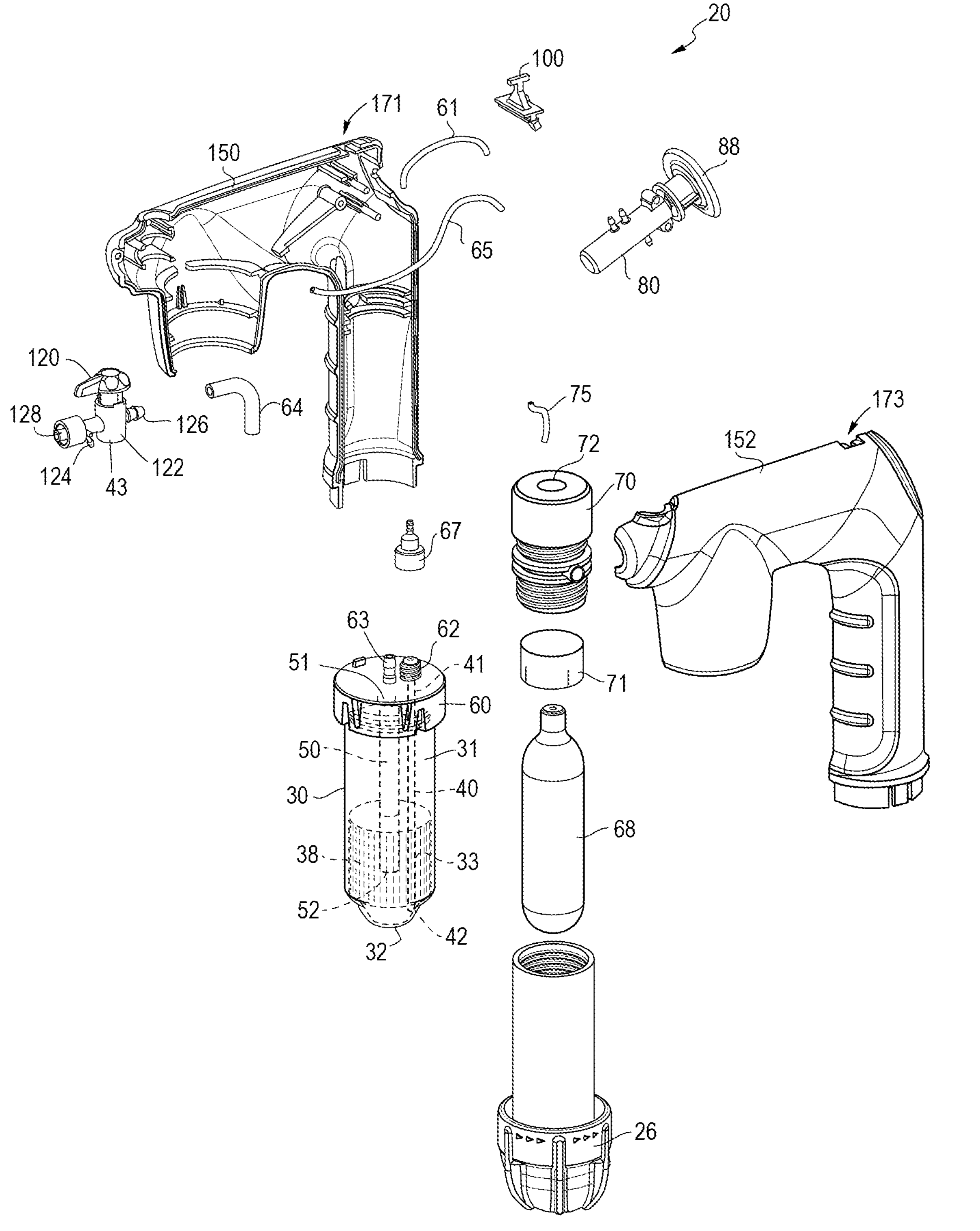
FIG. 3 is an exploded view of the system of FIG. 1, showing a back valve (first valve).

The container 30 may comprise any suitable size and shape for holding the therapeutic agent 38. As shown in FIGS. 1 and 3, the container 30 comprises a generally tube-shaped configuration having a first region 31, a second region 32, and a reservoir 33 defined by an interior of the container 30.

Referring to FIG. 3, the container 30 may further comprise an inlet tube 40, an outlet tube 50, and a cap 60, where the cap 60 is configured to be secured to the first region 31 of the container 30. The inlet tube 40 has first and second ends 41 and 42 with a lumen extending therebetween, while the outlet tube 50 has first and second ends 51 and 52 with a lumen extending therebetween. The first end 41 of the inlet tube 40 is placed in fluid communication with an inlet port 62 formed in the cap 60, while the first end 51 of the outlet tube 50 is placed in fluid communication with an outlet port 63 formed in the cap 60. A cap 67 may be secured on the inlet port 62, which will allow the connection between the inlet port 62 and the tubing 61 (see FIGS. 3 and 4). In some embodiments, an O-RING may be placed around the inlet port 62 or around the first end 41 of the inlet tube 40 (e.g., when the first end 41 extends out from the inlet port 62), which ensures that the cap 67 is well sealed when the cap 67 is secured on the inlet port 62, such that no fluid escapes but goes right into the container 30 during operation.

Figure 15:
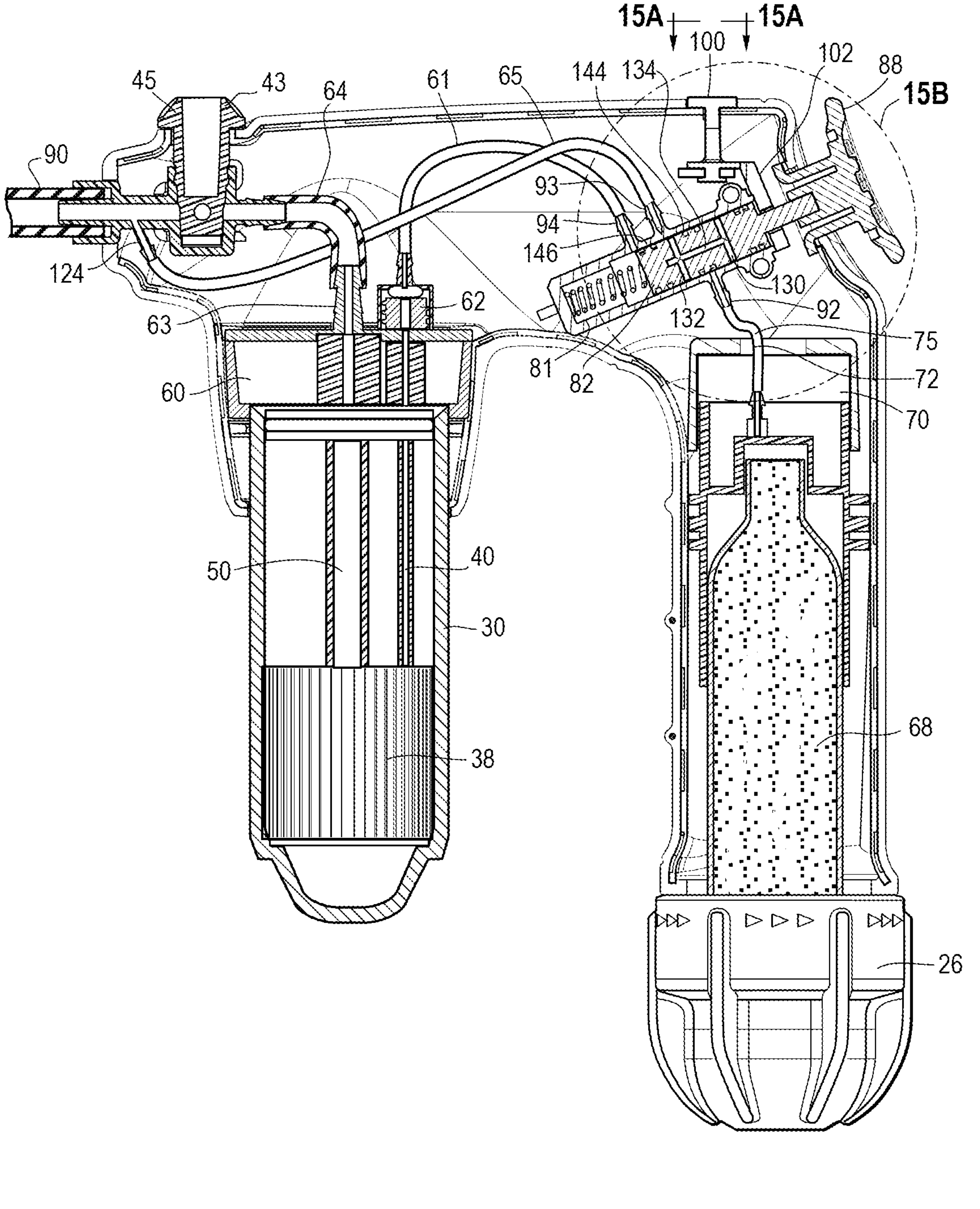
FIG. 15 is a cross-sectional view of the system of FIG. 1, showing the front valve in the first state, the switch in the first position, and the button in the default state.
Figure 15A:
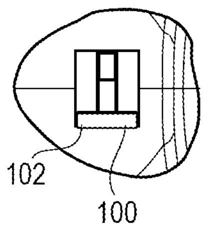
FIG. 15A is a detailed view of the switch of FIG. 15.
Figure 16:
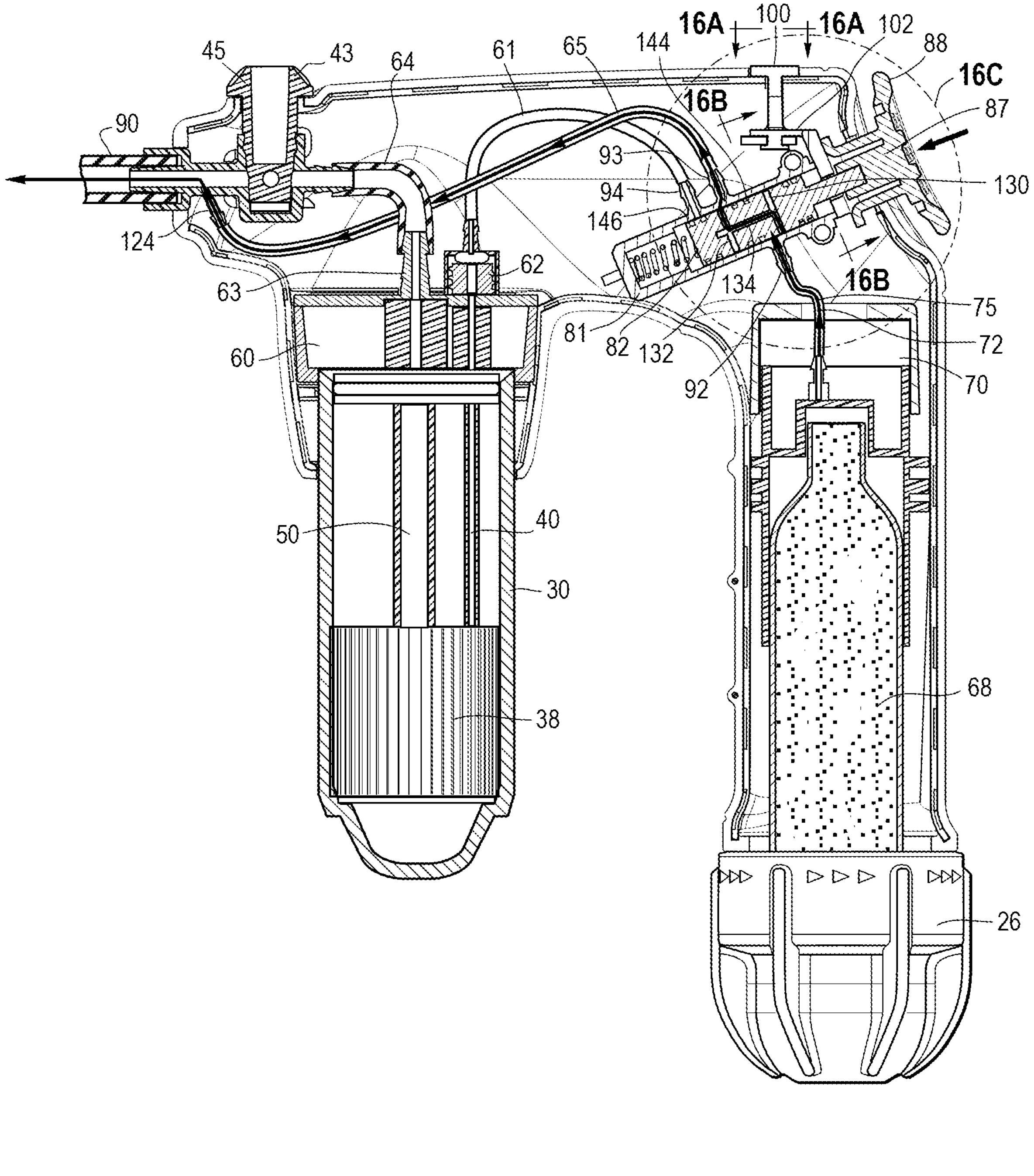
FIG. 16 is another cross-sectional view of the system of FIG. 1, showing the front valve in the first state, the switch in the first position, and the button depressed.
Figure 16A:
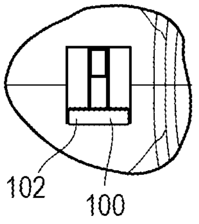
FIG. 16A is a detailed view of the switch of FIG. 16.
Figure 16B:
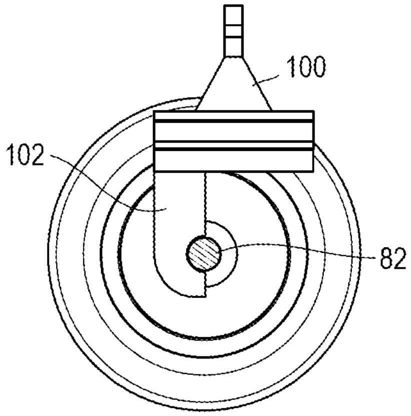
FIG. 16B is a cross-sectional view of a portion of the system of FIG. 16, showing the switch in the first position.
Figure 17:
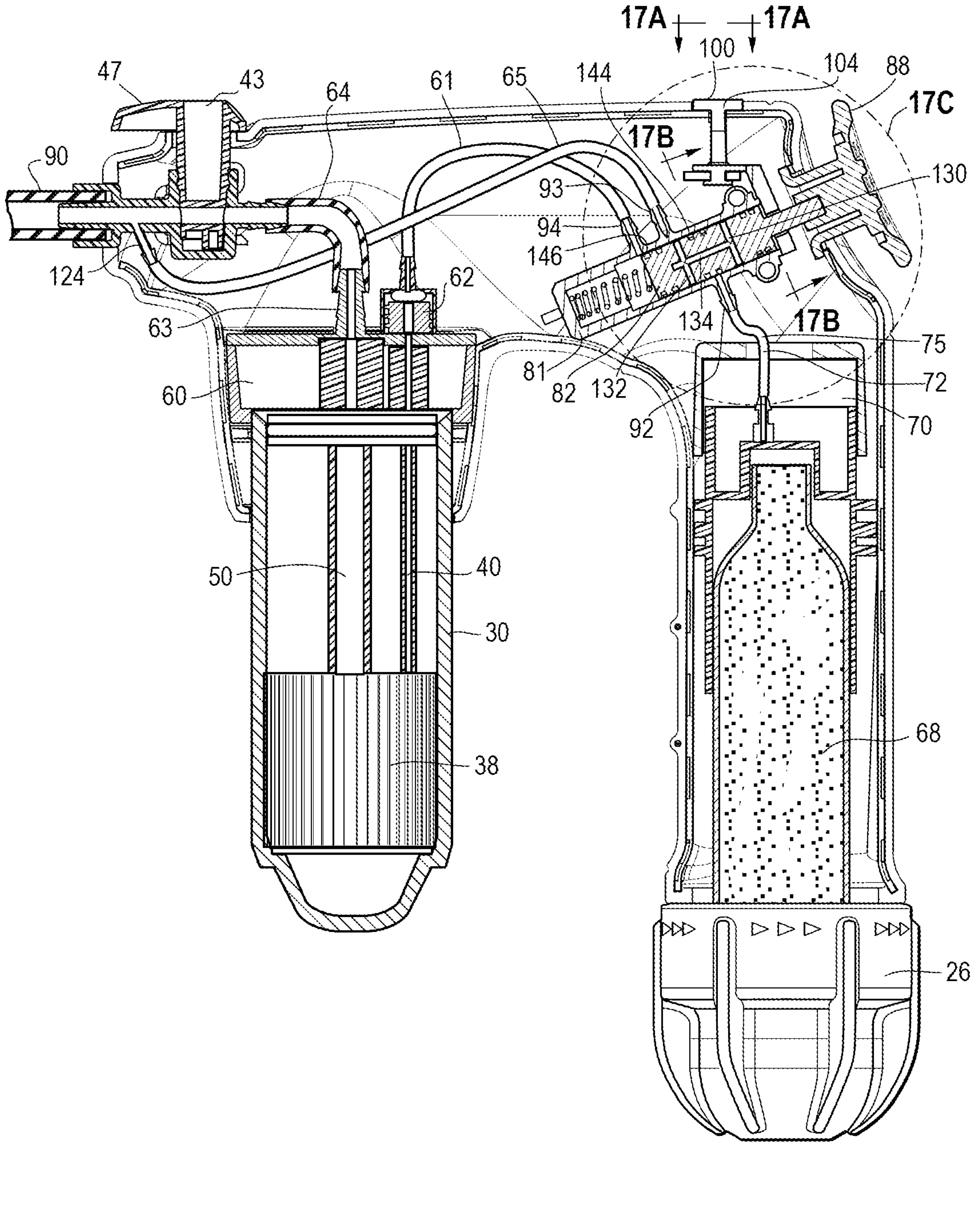
FIG. 17 is another cross-sectional view of the system of FIG. 1, showing the front valve in the second state, the switch in the second position, and the button in the default state.
Figure 17A:
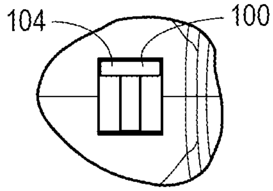
FIG. 17A is a detailed view of the switch of FIG. 17.
Figure 18:
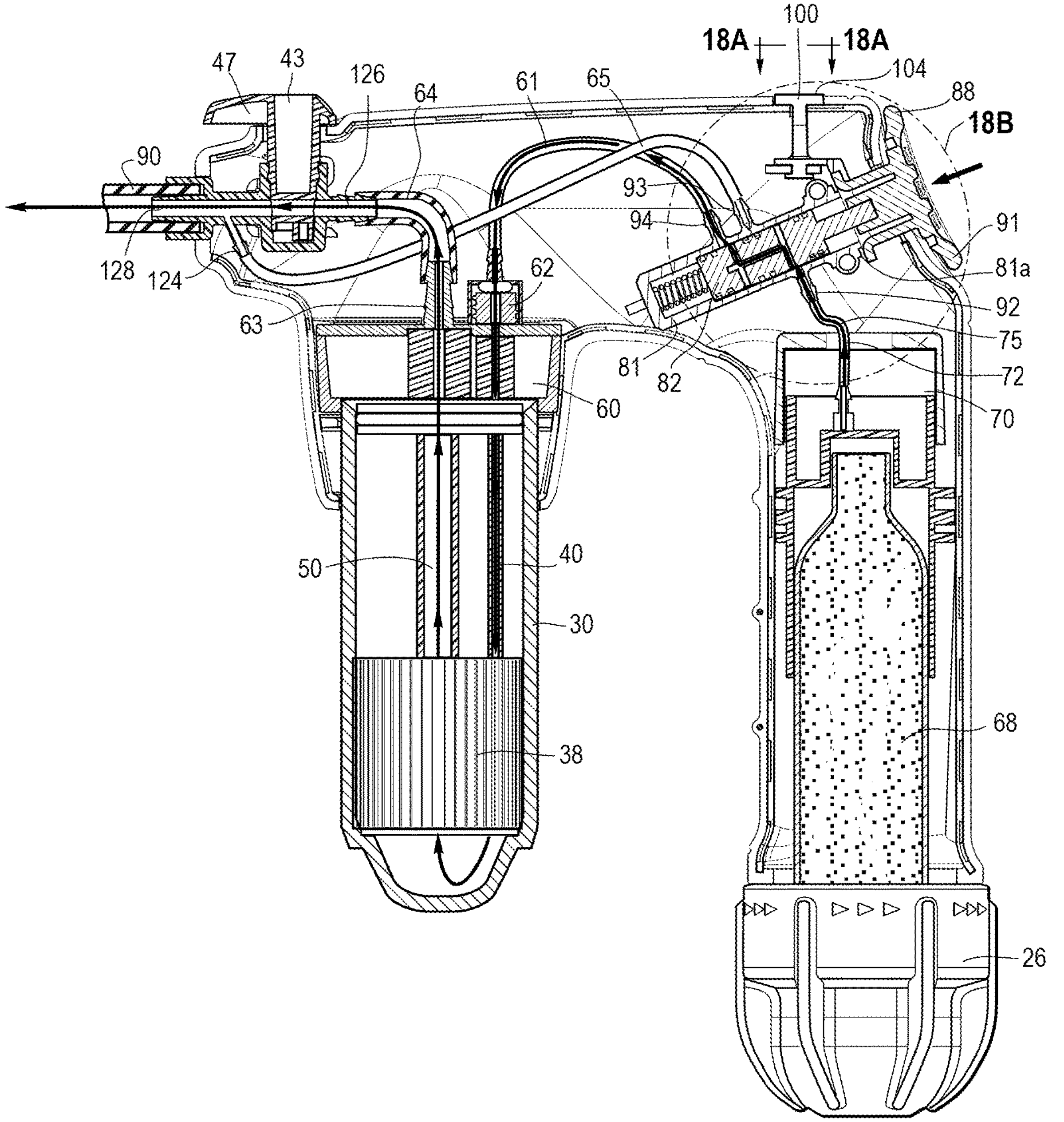
FIG. 18 is another cross-sectional view of the system of FIG. 1, showing the front valve in the second state, the switch in the second position, and the button depressed.
Figure 18A:
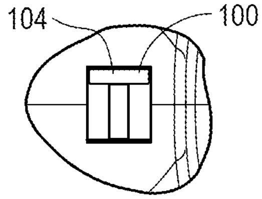
FIG. 18A is a detailed view of the switch of FIG. 18.

The outlet port 63 in the cap 60 may be placed in fluid communication with tubing 64, which extends in a distal direction and connects to the catheter 90 with the second valve 43 disposed therebetween. By manipulating the second valve 43, a user has the option to selectively deliver the therapeutic agent 38 flowing from the tubing 64 via the catheter 90. For example, the second valve 43 may be configured to have a first state 45 (e.g., a closed state, as shown in FIG. 2A) and a second state 47 (e.g., an open state, as shown in FIG. 2B). When the second valve 43 is in the first state 45 (e.g., as shown in FIGS. 4, 15, and 16), the catheter 90 is not in fluid communication with the tubing 64 and the container 30. When the second valve 43 is in the second state 47 (e.g., as shown in FIGS. 5, 17, and 18), the catheter 90 is in fluid communication with the tubing 64 and the container 30.

During operation, fluid passed through the inlet port 62 of the cap 60 is directed through the inlet tube 40 and into the reservoir 33. Notably, the u-shaped curvature near the second region 32 of the container 30 effectively changes the direction of the fluid flow by approximately 180 degrees, such that the fluid originally flows in a direction from the first region 31 of the container 30 towards the second region 32, and then from the second region 32 back towards the first region 31. As shown in FIGS. 1 and 3, the first region 31 of the container 30 is disposed vertically above the second region 32 of the container 30 during use, however, it is possible to have different placements of the first and second regions 31 and 32 relative to one another, such that they are disposed at least partially horizontally adjacent to one another.

The second end 52 of the outlet tube 50 may terminate a predetermined distance above the second region 32 of the container 30, as shown in FIG. 3. Accordingly, when fluid from the pressure source 68 is redirected from the second region 32 towards the first region 31, the fluid and the therapeutic agent 38 within the reservoir 33 may be directed through the outlet tube 50, through the outlet port 63, and towards a target site. Alternatively, the outlet tube 50 may be omitted and the therapeutic agent 38 may flow directly from the reservoir 33 into the outlet port 63. Other variations on the container 30 and the outlet port 63 may be found in U.S. Pat. No. 8,118,777, which is hereby incorporated by reference in its entirety.

The cap 60 may comprise any suitable configuration for sealingly engaging the first region 31 of the container 30. In one example, an O-ring is held in place around a circumference of the cap 60 to hold the therapeutic agent 38 within the reservoir 33. The inlet and outlet tubes 40 and 50 may be held in place within the container 30 by one or more support members, such as those explained further in U.S. Pat. No. 8,118,777.

Further, the cap 60 may comprise one or more flanges that permit a secure, removable engagement with a complementary internal region of the section 25 of the housing 22. For example, by rotating the container 30, the flange of the cap 60 may lock in place within the section 25.

Advantageously, in this manner, a first container holding a first therapeutic agent may be coupled to the housing 22 for use with the system 20, and subsequently a second container holding a second composition or agent may be coupled to the housing 22 for use with the system 20. By way of example, and without limitation, in one embodiment the system 20 may be "preloaded" with a first container 30 holding a therapeutic agent in the form of a hemostatic power. At a later time, it may be deemed beneficial to deliver a mucoadhesive composition, in which case the first container 30 may be rotated to disengage its flange from the section 25 of the housing 22, and then insert a second container 30 into the section of the housing 22 for delivery of the mucoadhesive composition. For the sake of brevity, the formulation in the container 30 will be referred to as a "therapeutic agent 38," although as explained herein certain formulations in a container 30 coupled to the housing 22 may be interchanged or varied and may or may not achieve a therapeutic effect per se.

The pressure source 68 may comprise one or more components capable of producing or furnishing a fluid having a desired pressure. In one embodiment, the pressure source 68 may comprise a pressurized fluid, such as a liquid or gas. For example, as shown in FIG. 3, the pressure source 68 may comprise a pressurized fluid cartridge of a selected gas or liquid, such as carbon dioxide, nitrogen, or any other suitable gas or liquid that may be compatible with the human body. The pressurized fluid cartridge may contain the gas or liquid at a relatively high, first predetermined pressure, for example, around 1,800 psi inside of the cartridge. The pressure source 68 optionally may comprise one or more commercially available components.

The fluid may flow from the pressure source 68 through a pressure regulator, such as a regulator valve 70 having a pressure outlet 72, which may reduce the pressure to a lower, second predetermined pressure. In some embodiments, as shown in FIG. 3, a spacer 71 may be disposed between the regulator valve 70 and the pressure source 68, which facilitates securing the pressure source 68 in place during transportation.

The actuator 26 may be actuated to release the fluid from the pressure source 68. For example, a user may rotate the actuator 26, which translates into linear motion via a threaded engagement between the actuator 26 and the housing 22. When the linear advancement is imparted to the pressure source 68, the regulator valve 70 may pierce through a seal of the pressure cartridge (and the spacer 71) to release the high pressure fluid. After the regulator valve 70 reduces the pressure, the fluid may flow from the pressure outlet 72 towards the first valve 80 via tubing 75.

Referring to FIGS. 3 and 13A-14B, the second valve 43 may be a stopcock including an upper portion 120 and a lower portion 122. The lower portion 122 includes a first inlet port 124, a second inlet port 126, an outlet port 128, and a middle section 125, where the first inlet port 124 and the outlet port 128 are disposed distal to the middle section 125, and the second inlet port 126 is disposed proximal to the middle section 125. A lower section 123 of the upper portion 120 includes a through hole 121 and is configured to be received in the middle section 125. The second inlet port 126 is configured to be connected to the tubing 64 and the outlet port 128 is configured to be connected to the catheter 90.

The second valve 43 can be transitioned between the first state 45 (e.g., a closed state, as shown in FIG. 2A) and the second state 47 (e.g., an open state, as shown in FIG. 2B) via rotation of the upper portion 120 of the second valve 43. For example, as shown in FIGS. 2A and 2B, rotating the upper portion 120 of the second valve 43 in a first direction 110 (e.g., clockwise) may transition the second valve 43 from the first state 45 (e.g., the closed state) to the second state 47 (e.g., the open state), and rotating the second valve 43 in an opposite second direction (e.g., counterclockwise; not shown) may transition the second valve 43 from the second state 47 (e.g., the open state) back to the first state 45 (e.g., the closed state). When the second valve 43 is in the first state 45, a passageway between the second inlet port 126 and the outlet port 128 is blocked by the lower section 123 of the upper portion 120, such that the catheter 90 is not in fluid communication with the container 30. When the second valve 43 is in the second state 47, a passageway is established between the second inlet port 126 and the outlet port 128 via the through hole 121, such that the catheter 90 is in fluid communication with the container 30.

Figure 9:
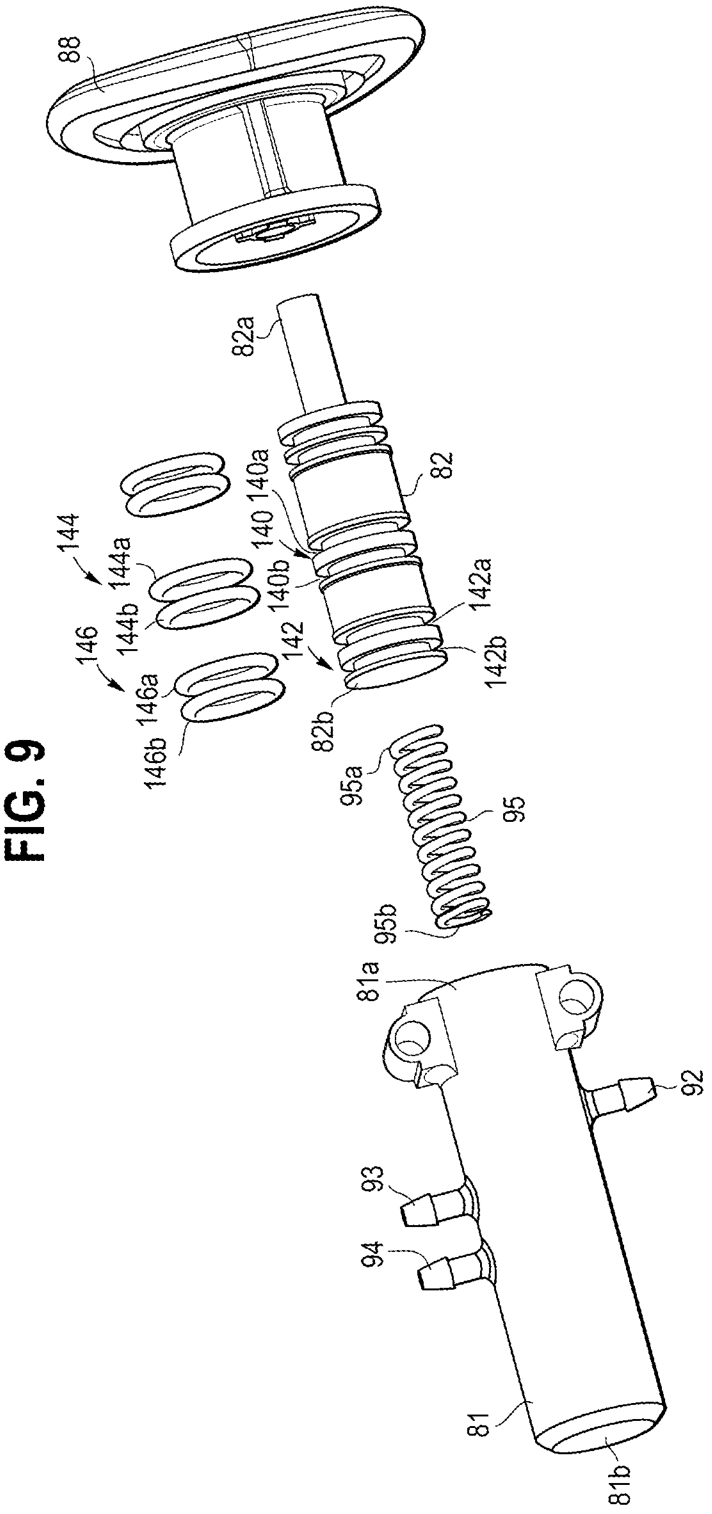
FIG. 9 is an enlarged exploded view of a portion of the system of FIG. 1, showing the back valve and the button, where the back valve includes a main body and a piston.
Figure 10:
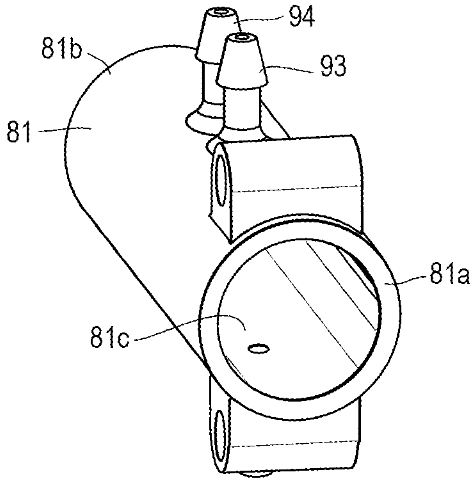
FIG. 10 is a perspective view of the main body of the back valve of FIG. 9.
Figure 11:
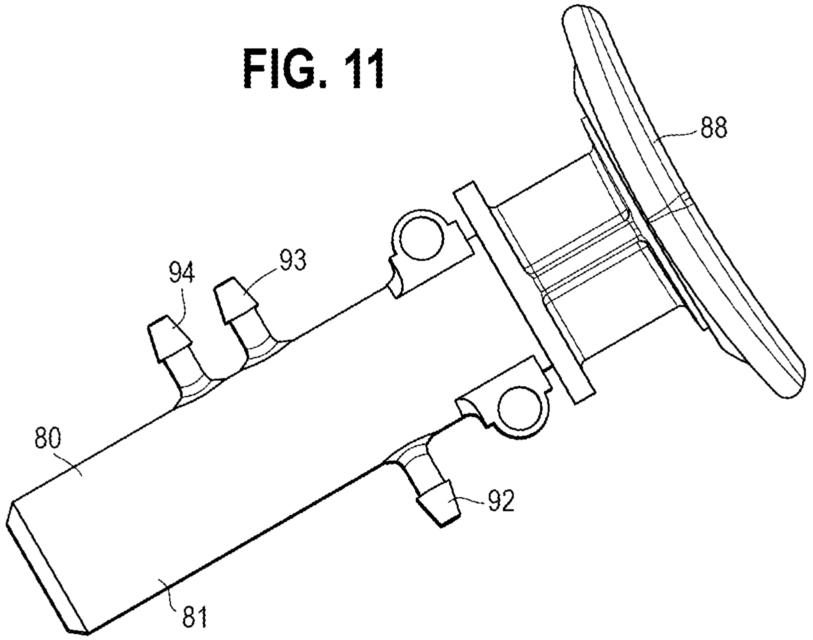
FIG. 11 is a perspective assembled view of the system of FIG. 9, showing the back valve and the button coupled together.
Figure 15B:
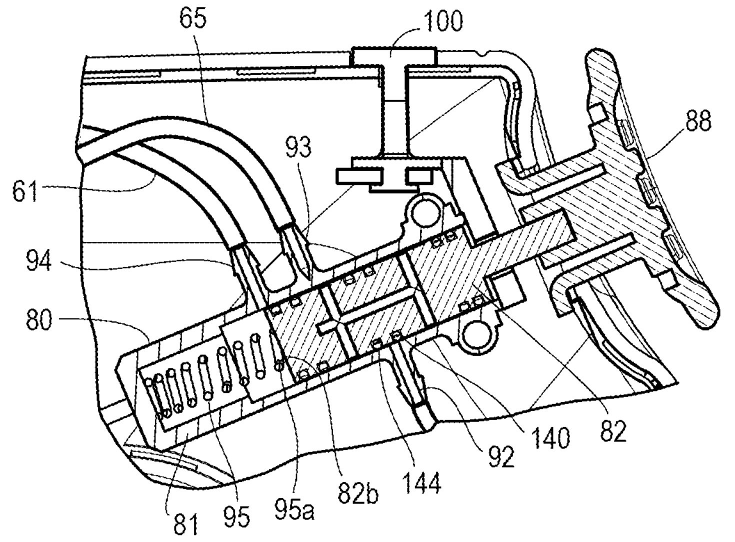
FIG. 15B is an enlarged detailed view of a portion of the system of FIG. 15.

Referring to FIGS. 3 and 9-12, the first valve 80 comprises a main body 81 having a proximal end 81*a*, a distal end 81*b*, and an inner lumen 81*c* extending between the proximal end 81*a* and the distal end 81*b*. A piston 82, which has proximal and distal end portions 82*a* and 82*b*, is disposed at least partially within the main body 81 and is slidably movable along a length of the inner lumen 81*c* of the main body 81. A button 88 is configured to be connected to the proximal end portion 82*a* of the piston 82 such that depression of the button 88 causes the piston 82 to move distally along a length of the inner lumen 81*c* of the main body 81. This proximal end portion 82*a* of the piston 82 may extend a distance outside of the main body 81 (e.g., as shown in FIG. 15), to facilitate coupling to the button 88. The distal end portion 82*b* of the piston 82 may be positioned adjacent to a proximal end 95*a* of a compression spring 95 (e.g., as shown in FIGS. 9 and 15B). In this manner, the piston 82 can be provided with a default state (e.g., when no force is applied to the button 88) in which the piston 82 is inclined to be disposed further proximally, but if the user applies a sufficient force to the button 88 then the piston 82 can be moved distally against the force of the compression spring 95, for purposes described below. Once the button 88 is released (e.g., not depressed), the piston 82 returns to the default state.

Various inlet and outlet ports may be associated with the first valve 80. In the embodiment shown in FIGS. 1-18, the main body 81 includes an inlet port 92, a first outlet port 93, and a second outlet port 94. The inlet port 92 of the first valve 80 may be coupled to the tubing 75 extending from the pressure outlet 72 of the regulator valve 70 (e.g., as shown in FIG. 4), thus providing pressurized fluid at a predetermined pressure into the first valve 80. The first outlet port 93 may be coupled to the tubing 65 extending from the first inlet port 124 of the second valve 43 (e.g., as shown in FIG. 4). The second outlet port 94 may be coupled to the tubing 61 extending from the inlet port 62 of the cap 60.

Figure 12:
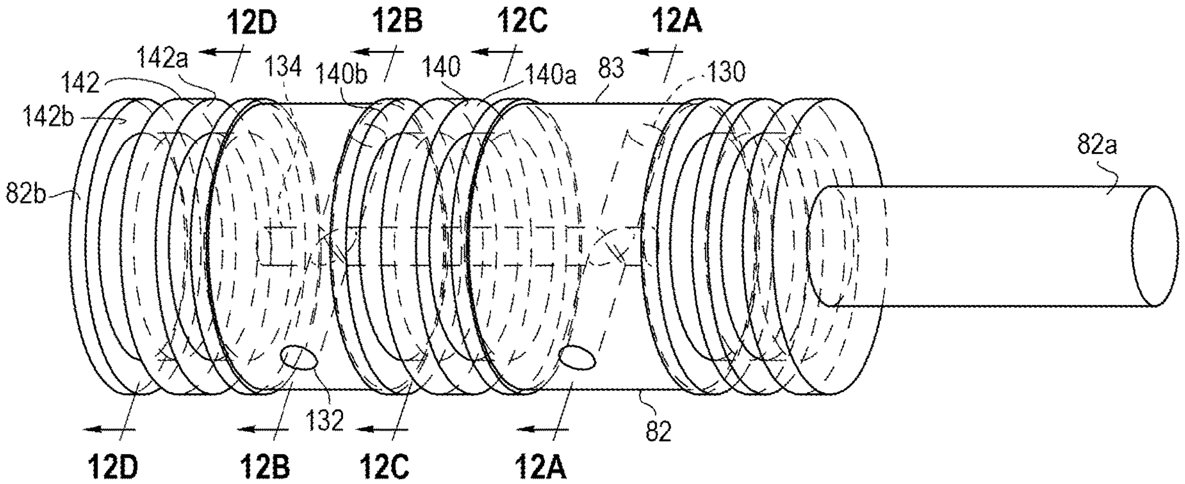
FIG. 12 is a perspective view of the piston of the back valve of FIG. 9.
Figure 12A:
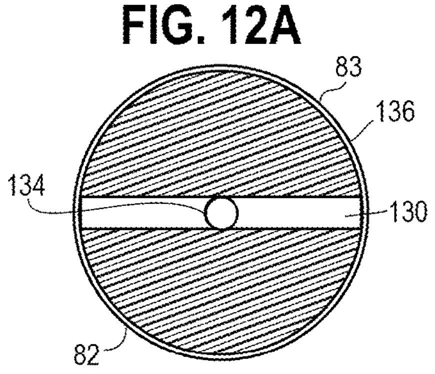
FIGS. 12A-12D are cross-sectional views of the piston of FIG. 12.
Figure 12B:
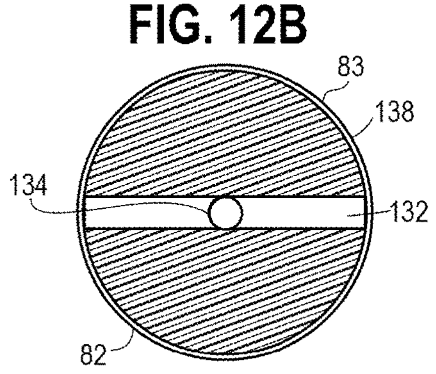
Figure 12C:
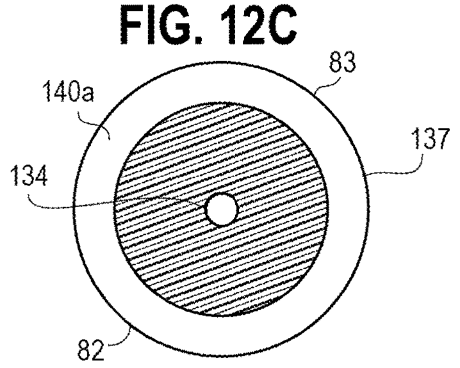
Figure 27:
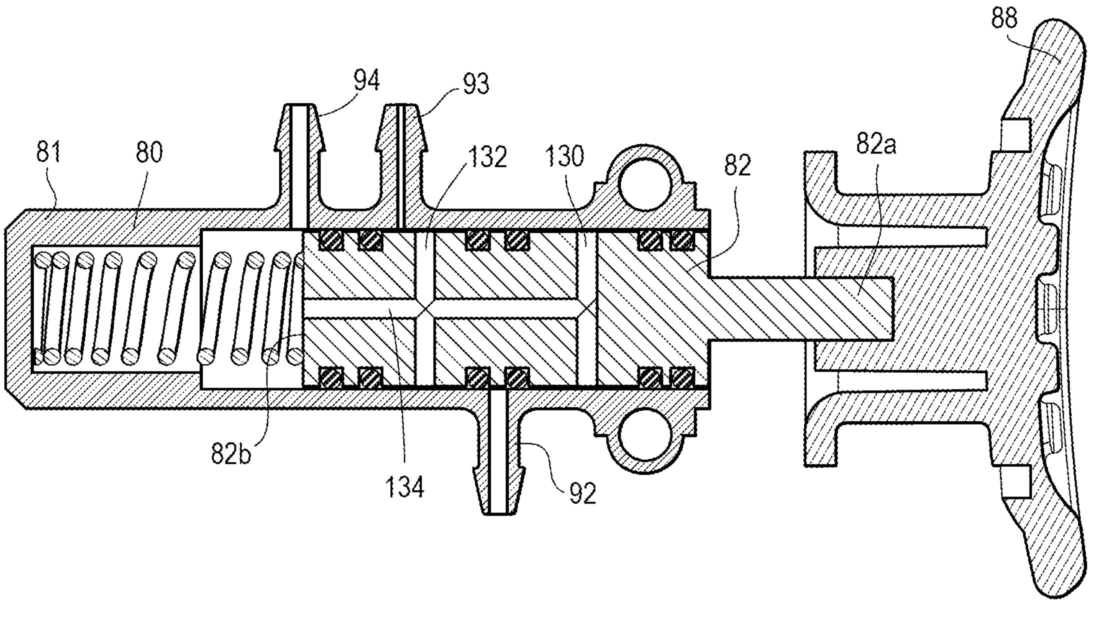
FIG. 27 is a schematic cross-sectional view of another embodiment of the back valve.
Figure 28:
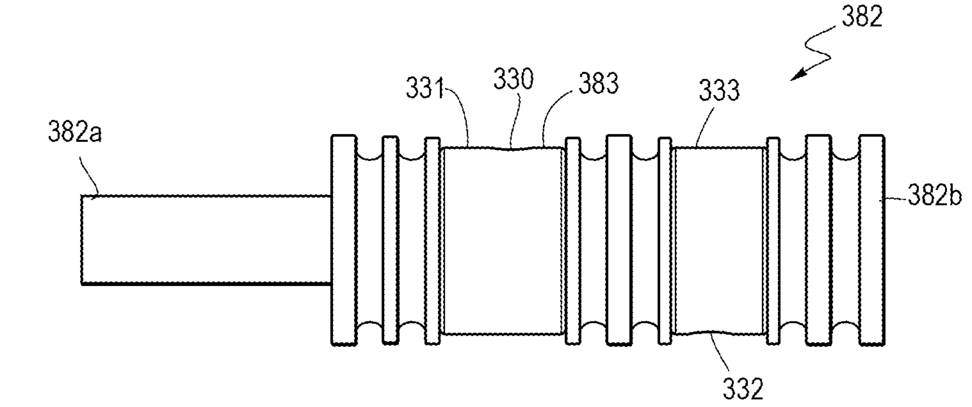
FIG. 28 is a perspective view of another embodiment of the piston of the back valve of FIG. 9.
Figure 29:
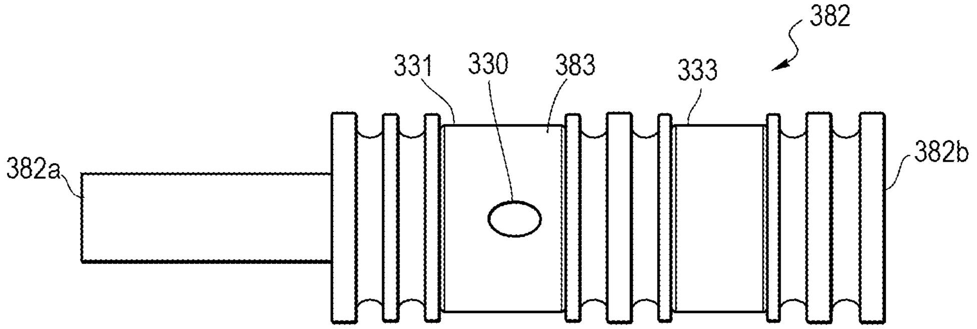
FIG. 29 is another perspective view of the piston of FIG. 28.
Figure 30:
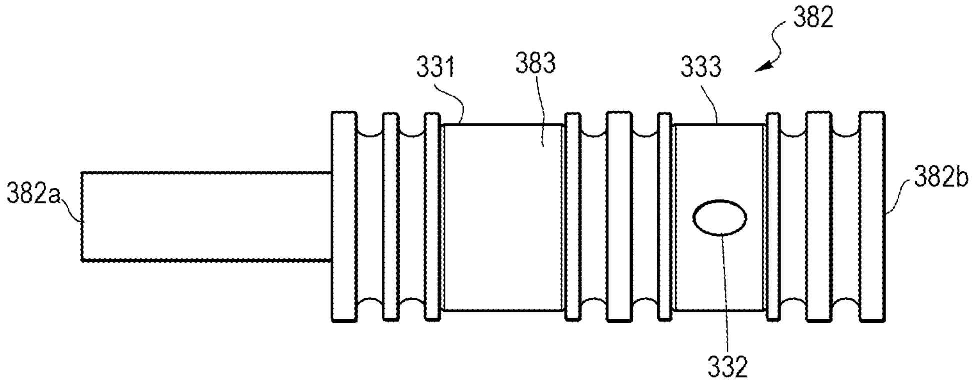
FIG. 30 is another perspective view of the piston of FIG. 28.

As shown in FIG. 12, the piston 82 of the first valve 80 may include a generally tubular body 83 having spaced apart first groove 130 and second groove 132 connected by a bridge 134 extending along a length of the piston 82. The bridge 134 may extend through at least a portion of the piston 82. In some embodiments, as shown in FIG. 27, the bridge 134 may extend to the distal end portion 82*b* of the piston 82, which may make the piston 82 easier to manufacture. The first groove 130 extends through the piston 82 radially along a diameter of a first cross section 136 of the piston 82, and the second groove 132 extends through the piston 82 radially along a diameter of a second cross section 138 of the piston 82. With this configuration, fluid communication routes can align to permit flow between the first and second grooves 130 and 132 via the bridge 134 inside the piston 82.

Referring to FIGS. 9 and 12, the piston 82 of the first valve 80 may further include spaced apart first valley 140 and second valley 142 disposed on an outer surface of the piston 82. The first and second valleys 140 and 142 are configured for respectively receiving first and second sealing members 144 and 146 configured for selectively closing the inlet port 92, the first outlet port 93, or the second outlet port 94, as discussed in greater detail below.

Figure 12D:
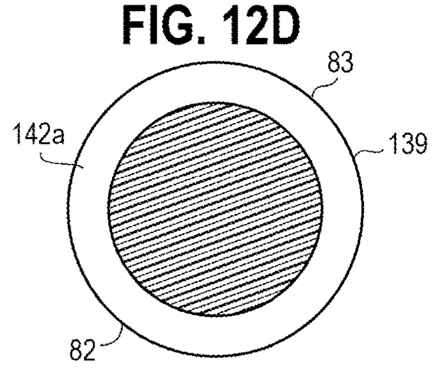
Figure 13A:
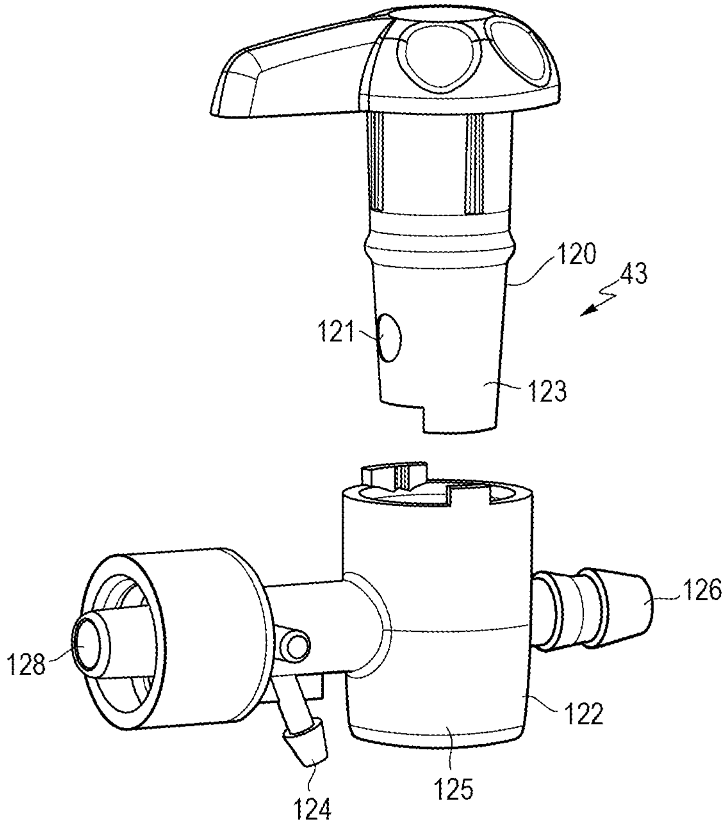
FIG. 13A is an enlarged perspective view of the front valve of FIG. 1, showing an upper portion of the front valve and a lower portion of the front valve.
Figure 13B:
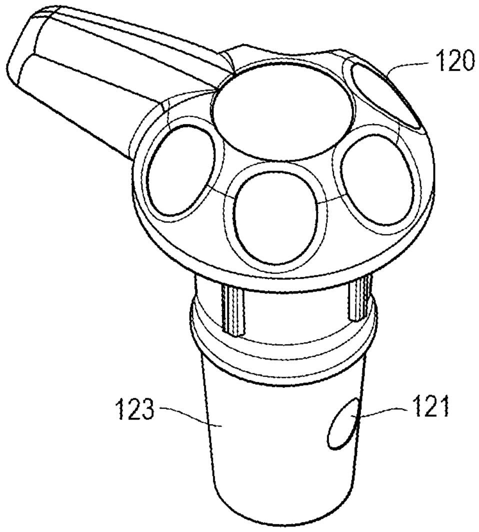
FIG. 13B is an enlarged perspective view of the upper portion of the front valve of FIG. 13A.
Figure 14A:
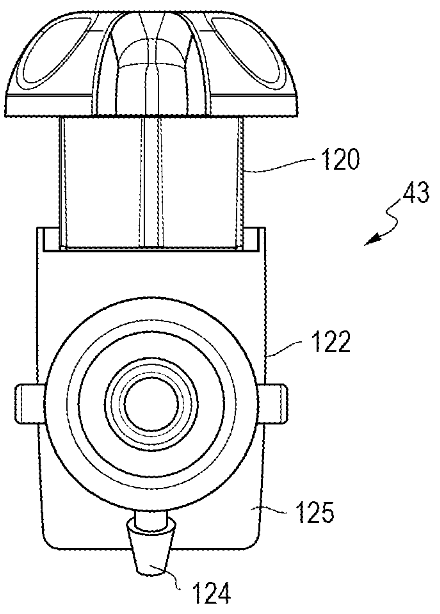
FIGS. 14A and 14B are perspective views of the front valve of FIG. 13A, showing the upper portion and the lower portion of the front valve coupled together.
Figure 14B:
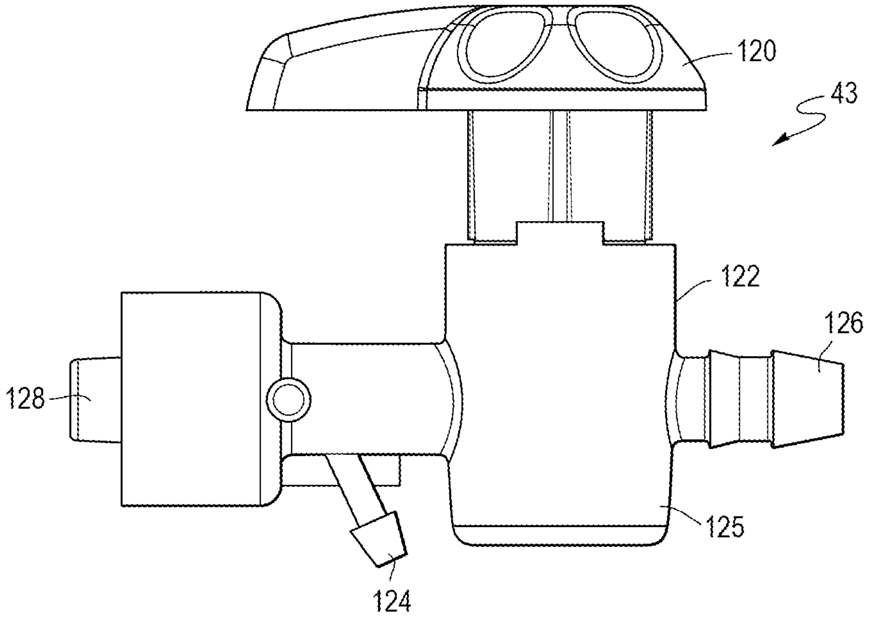

Referring to FIGS. 12-12D, the first valley 140 may extend around a circumference of a third cross section 137 of the piston 82 with a constant depth, and the second valley 142 may extend around a circumference of a fourth cross section 139 of the piston 82 with a constant depth. The first, second, third, and fourth cross sections 136, 138, 137, and 139 of the piston 82 may be spaced apart and parallel to each other. As shown in FIG. 12, the first valley 140 is disposed proximal to the second valley 142, the first groove 130 is disposed proximal to the first valley 140, and the second groove 132 is disposed between the first and second valleys 140 and 142.

The first valley 140 may include a first sub-valley 140*a* and a second sub-valley 140*b* spaced apart by a portion of the outer surface of the piston 82. The second valley 142 may include a third sub-valley 142*a* and a fourth sub-valley 142*b* spaced apart by a portion of the outer surface of the piston 82. The first and second sealing members 144 and 146 each may include at least one O-Ring configured to be received in the respective first and second valleys 140 and 142. As shown in FIG. 9, the first sealing member 144 includes a first O-Ring 144*a* configured to be disposed in the first sub-valley 140*a* and a second O-Ring 144*b* configured to be disposed in the second sub-valley 140*b*. The second sealing member 146 includes a third O-Ring 146*a* configured to be disposed in the third sub-valley 142*a* and a fourth O-Ring 146*b* configured to be disposed in the fourth sub-valley 142*b*.

In use, the piston 82 is disposed at least partially within the main body 81 and is slidably movable along a length of the inner lumen 81*c* of the main body 81. The inlet port 92, the first outlet port 93, and the second outlet port 94 of the main body 81 of the first valve 80, the first and second valleys 140 and 142 of the piston 82, and the first and second sealing members 144 and 146 are configured and spaced such that when the second sealing member 146 is axially aligned with the second outlet port 94, the first sealing member 144 is axially offset from the inlet port 92 and the first outlet port 93, such that fluid communication (e.g., a first fluid communication) is established between the inlet port 92 and the first outlet port 93 via the first and second grooves 130 and 132 and the bridge 134 (e.g., as shown in FIG. 16). In the meantime, when the first sealing member

144 is axially aligned with the first outlet port 93, the first sealing member 144 is axially offset from the inlet port 92 and the second sealing member 146 is axially offset from the second outlet port 94, such that fluid communication (e.g., a second fluid communication) is established between the inlet port 92 and the second outlet port 94 via the first and second grooves 130 and 132 and the bridge 134 (e.g., as shown in FIG. 18).

As discussed above, the system 20 is also provided with a switch 100, which is configured to selectively permit actuation of the first valve 80 to deliver the pressurized fluid without the therapeutic agent 38 or to deliver the therapeutic agent 38. In some embodiments, as shown in FIGS. 2A, 2B, and 4-5A, the switch 100 may be a slider 100, where the housing 22 is configured to slidably support the slider 100, such that when the slider 100 is in the first position 102 (e.g., as shown in FIGS. 2A and 4A), the slider 100 allows the button 88 to be depressed to a first state 87 (e.g., as shown in FIG. 4A), allowing the pressurized fluid in the pressure source 68 to flow through the first valve 80 and into the catheter 90 absent delivery of the therapeutic agent, and when the slider 100 is in the second position 104 (e.g., as shown in FIGS. 2B and 5A), the slider 100 allows the button 88 to be depressed to a second state 91 (e.g., as shown in FIG. 5A), allowing the pressurized fluid in the pressure source 68 to flow through the first valve 80, into the container 30, and urge the therapeutic agent 38 in the container 30 through the catheter 90, as discussed in greater detail below.

Figure 4A:
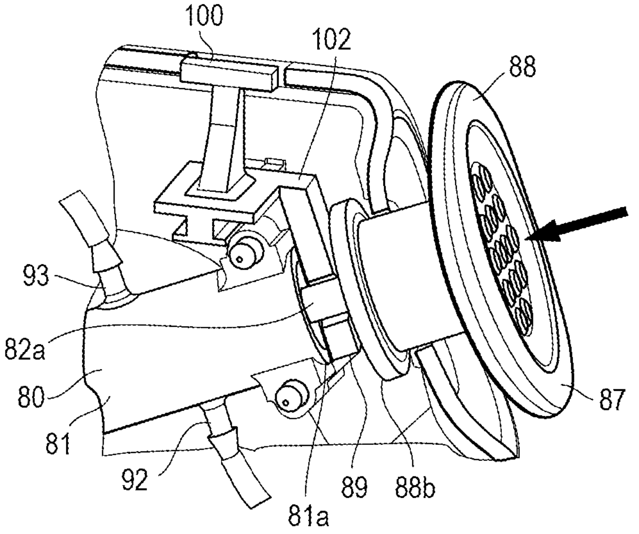
FIG. 4A is a partially enlarged perspective view of a portion of the system of FIG. 4, showing the switch in the first position and the button depressed.
Figure 5A:
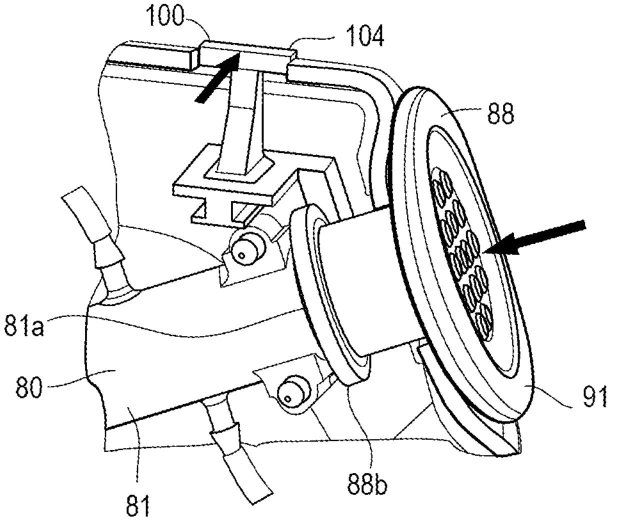
FIG. 5A is a partially enlarged perspective view of a portion of the system of FIG. 5, showing the switch in the second position and the button depressed.
Figure 5B:
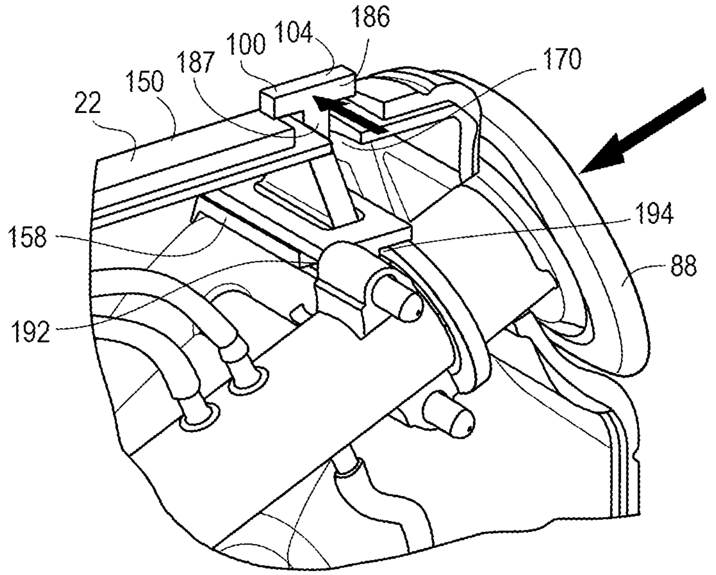
FIG. 5B is an enlarged detailed view of a portion of the system of FIG. 5.

Referring to FIGS. 4-5B, when the slider 100 is in the first position 102 (e.g., as shown in FIGS. 4 and 4A), the slider 100 blocks the button 88 such that the button 88 can be moved from a default state (e.g., when no force is applied on the button 88; as shown in FIG. 15) distally a maximum of a first distance (e.g., until the distal end 88*b* of the button 88 contacts the slider 100; as shown in FIG. 4A, where the button 88 is in the first state 87). When the slider 100 is in the second position 104 (e.g., as shown in FIGS. 5 and 5A), the slider 100 allows the button 88 to be moved distally a maximum of a second distance (e.g., until the distal end 88*b* of the button 88 contacts the proximal end 81*a* of the main body 81 of the first valve 80; as shown in FIG. 5A, where the button is in the second state 91). The first distance is smaller than the second distance. As shown in FIG. 4A, when the slider 100 is in the first position 102, the slider 100 occupies a space 89, where the space 89, when not occupied, allows movement of the button 88 from the first state 87 to the second state 91. As shown in FIG. 5A, when the slider 100 is in the second position 104, the slider 100 is moved away from the space 89, allowing the button 88 to be depressed to the second state 91.

Referring to FIGS. 15-18, when the button 88 is in the default state (e.g., as shown in FIG. 15, where it is not engaged by a user), the force provided by the compression spring 95 biases the piston 82 to its default state, in which the first sealing member 144 disposed in the first valley 140 of the piston 82 is axially aligned with the inlet port 92 of the main body 81, such that the pressurized fluid from the pressure source 68 (as regulated by the regulator valve 70) does not flow into the first valve 80.

Figure 16C:
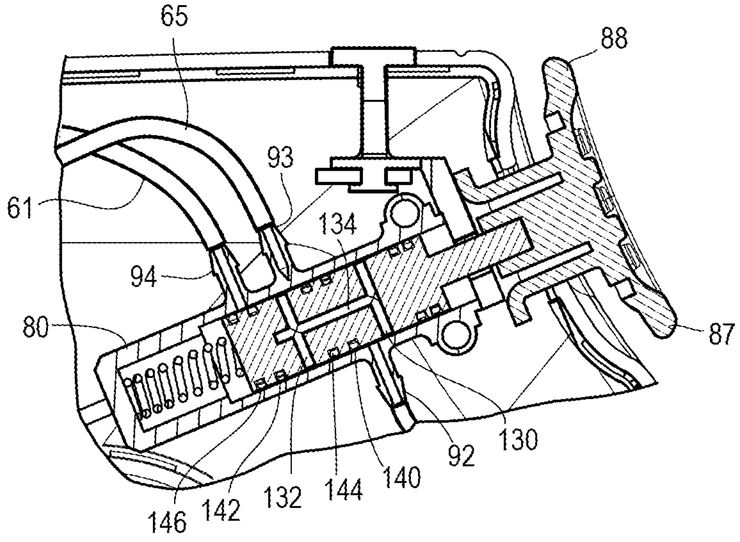
FIG. 16C is an enlarged detailed view of a portion of the system of FIG. 16.

As shown in FIGS. 16-16C, when the slider 100 is in the first position 102 and the button 88 is depressed by the user in a manner to overcome the force provided by the compression spring 95, the button 88 is advanced distally to the first state 87 (e.g., where the button 88 is fully depressed and blocked by the slider 100), in which the first sealing member 144 is axially offset from the inlet port 92 and the first outlet port 93, and the second sealing member 146 is axially aligned with the second outlet port 94, such that the pressurized fluid from the pressure source 68 flows into the first valve 80 via the inlet port 92, into the first groove 130, through the bridge 134, into the second groove 132, and exits the first valve 80 via the first outlet port 93. In this manner, pressurized fluid from the pressure source 68 (as regulated by the regulator valve 70) is directed into the first outlet port 93 and into tubing 65, where it is then directed into the catheter 90 via the first inlet port 124 of the second valve 43.

Figure 17B:
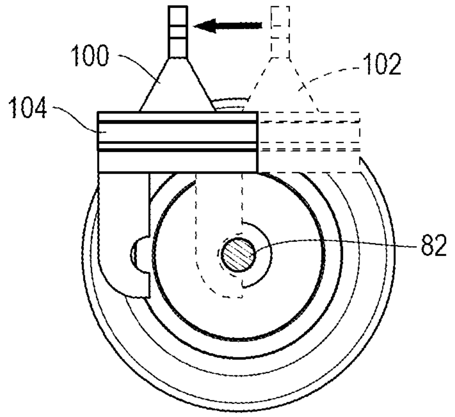
FIG. 17B is a cross-sectional view of a portion of the system of FIG. 17, illustrating the switch moved from the first position to the second position.
Figure 17C:
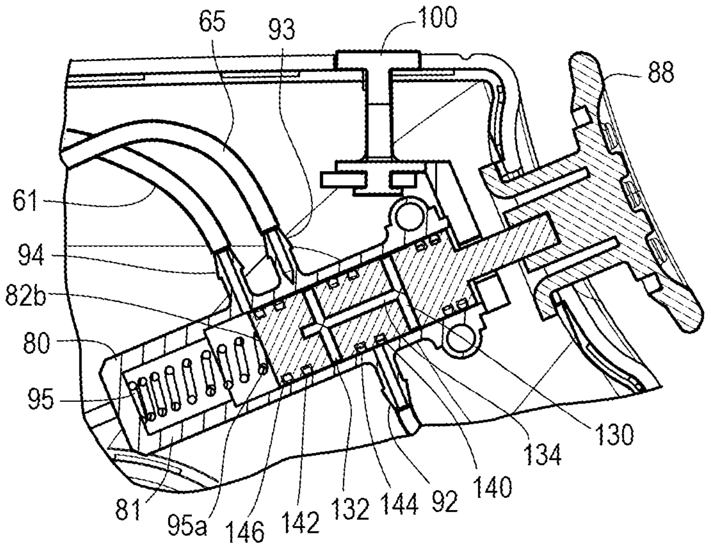
FIG. 17C is an enlarged detailed view of a portion of the system of FIG. 17.
Figure 18B:
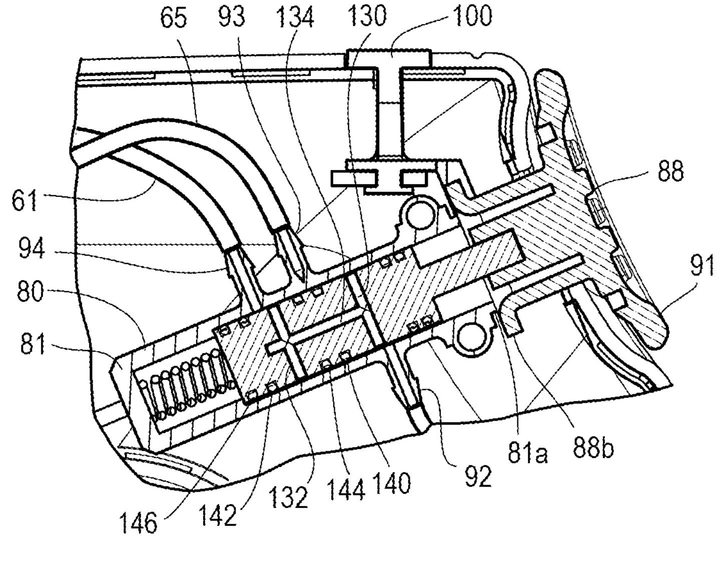
FIG. 18B is an enlarged detailed view of a portion of the system of FIG. 18.

Referring to FIGS. 17-18B, when the slider 100 is moved from the first position 102 to the second position 104 (e.g., as shown in FIG. 17B), the slider 100 is moved out of the way of the button 88, which allows the button 88 to be moved distally until the distal end 88*b* of the button 88 contacts the proximal end 81*a* of the main body 81 of the first valve 80 (e.g., as shown in FIG. 18B, where the button 88 is in the second state 91). When the button 88 is depressed to the second state 91, the first sealing member 144 is axially offset from the inlet port 92 of the main body 81 but is axially aligned with the first outlet port 93, and the second sealing member 146 is axially offset from the second outlet port 94 of the main body 81, such that the pressurized fluid from the pressure source 68 flows into the first valve 80 via the inlet port 92, into the first groove 130, through the bridge 134, into the second groove 132, and exits the first valve 80 via the second outlet port 94.

In this manner, pressurized fluid from the pressure source 68 (as regulated by the regulator valve 70) is directed into the second outlet port 94 and into the tubing 61, where it is then directed into the inlet port 62 of the cap 60 and into the container 30 holding the therapeutic agent 38, and where it is then directed into the outlet tube 50, into the outlet port 63 of the cap 60, and into the tubing 64, at which point, delivery of the therapeutic agent 38 can be controlled by the second valve 43, as discussed above. When the second valve 43 is in the second state 47 (e.g., as shown in FIG. 18), a passageway is established between the second inlet port 126 and the outlet port 128, such that the therapeutic agent 38 flowing from the tubing 64 can be delivered through the catheter 90 coupled to the outlet port 128.

As discussed above, the configuration of the slider 100, the first valve 80, and the button 88 allows the system 20 to deliver positive pressure prior to delivery of the therapeutic agent 38 (e.g., powder), which is advantageous for preventing fluid ingress in various situations, including but not limited to, when the catheter 90 is fed through a scope channel, between powder sprays, when the scope is moved to a new target, as well as when the scope is irrigated or accidentally dipped into the pool of blood/fluid, thereby improving system performance in fluid and moisture saturated medium. In addition, with the ability of the system 20 to deliver the therapeutic agent 38 (e.g., spray powder) in moisture saturated medium and remove the risk of system clogging, advantageously, it will improve the overall procedure time and customer experience, and also lead to reduced number of catheters packaged per system, thereby reducing environmental burden.

It will be appreciated that the number, configuration, and position of the grooves, bridge(s), valleys, sub-valleys, and sealing members included in the piston 82 and the inlet and outlet ports associated with the first valve 80 may be varied, as desired and/or needed, without departing from the scope of the present invention, as long as fluid communication routes can be selectively aligned to permit flow between the inlet port and the outlet port connected to the tubing 65 coupled to the inlet port 124 of the second valve 43 in one state of the first valve 80, and to permit flow between the inlet port and the outlet port connected to the tubing 61 coupled to the inlet port 62 of the cap 60 in another state of the first valve 80, such that the pressurized fluid (without the therapeutic agent 38) or the therapeutic agent 38 can be selectively delivered using the first valve 80 and the button coupled to the first valve 80.

Figure 6:
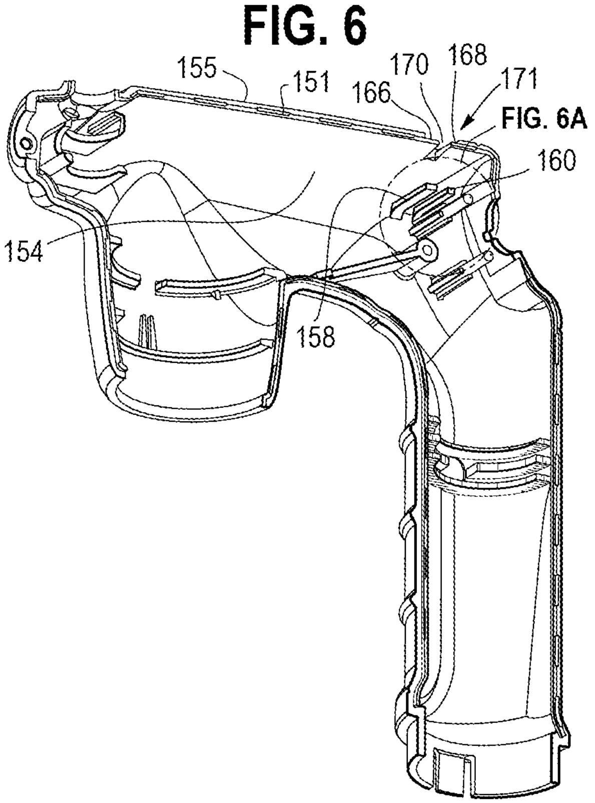
FIG. 6 is a perspective view of a first part of the housing of the system of FIG. 1.
Figure 6A:
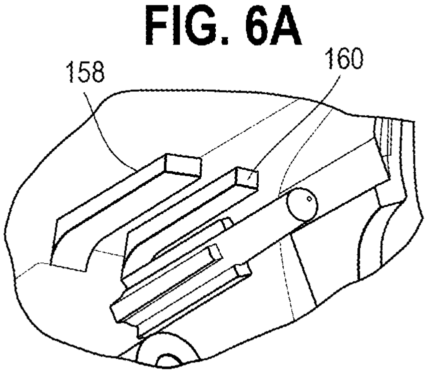
FIG. 6A is an enlarged detailed view of a portion of the first part of the housing of FIG. 6.
Figure 7:
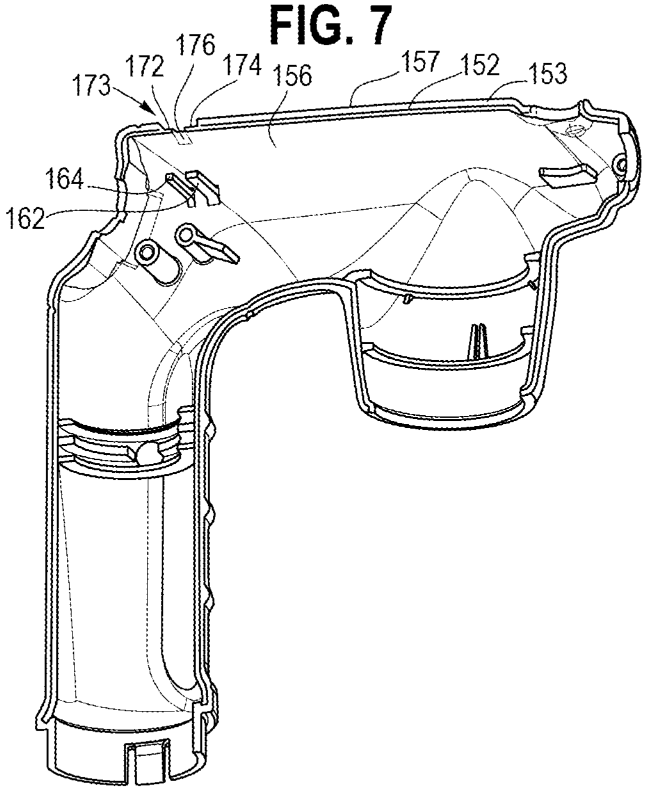
FIG. 7 is a perspective view of a second part of the housing of the system of FIG. 1.

Referring to FIGS. 6-8D, a first embodiment of the housing 22 and a first embodiment of the switch 100 are shown, where the switch 100 is a slider 100 slidably supported by the housing 22. The housing 22 includes a first portion 150 and a second portion 152, which are configured such that when coupled together, forming a cavity therebetween configured for at least partially retaining, holding, engaging, and/or covering other components of the system 20 (e.g., the container 30) and slidably support the slider 100. As shown in FIGS. 6-7, the first portion 150 of the housing 22 includes a first upper portion 151 and a first inner surface 154, and the second portion 152 of the housing 22 includes a second upper portion 153 and a second inner surface 156.

The first upper portion 151 includes a first concave portion 171 extending downward from the first upper surface 155 of the first upper portion 151, where the first concave portion 171 includes a first portion 166 and a second portion 168 disposed lower than the first upper surface 155 and includes a first cutout 170 disposed therebetween. The second upper portion 153 includes a second concave portion 173 extending downward from the second upper surface 157 of the second upper portion 153, where the second concave portion 173 includes a third portion 172 and a fourth portion 174 disposed lower than the second upper surface 157 and includes a second cutout 176 disposed therebetween. The first and second concave portions 171 and 173 are configured to slidably support at least a portion of the slider 100, as discussed in greater detail below.

The first portion 150 includes a first guide member 158 and a second guide member 160 extending outwardly from the first inner surface 154. The first and second guide members 158 and 160 are spaced apart and disposed at least partially underneath the first concave portion 171. The second portion 152 includes a third guide member 162 and a fourth guide member 164 extending outwardly from the second inner surface 156. The third and fourth guide members 162 and 164 are spaced apart and disposed at least partially underneath the second concave portion 173. The first, second, third, and fourth guide members are configured to slidably support at least a portion of the slider 100, as discussed in greater detail below.

Referring to FIGS. 8A-8D, the slider 100 includes an upper portion 180 and a lower portion 181. The upper portion 180 includes a top part 186 and a neck portion 187 extending downwardly from the top part 186. The lower portion 181 includes a main portion 188, which includes an upper section 189, a lower section 190, and a middle section 191 extending between and connecting the upper and lower sections 189 and 190, where a first groove 192 and a second groove 194 are formed between the upper and lower sections 189 and 190 and disposed on opposite sides of the middle section 191. The neck portion 187 extends upwardly from the upper section 189 of the lower portion 181. The lower portion 181 also includes an arm portion 182 extending outwardly and downwardly from a side surface 183 of the upper section 189. The arm portion 182 also includes a cutout 184 configured for receiving at least a portion of the proximal end portion 82*a* of the piston 82, as discussed in greater detail below.

Referring to FIGS. 3-5B, the first portion 150 of the housing 22 and the slider 100 are configured such that the first and second guide members 158 and 160 are slidably received in the first and second grooves 192 and 194, respectively, while the top part 186 is slidably received in the first concave portion 171 and slidably supported by the first and second portions 166 and 168 with the neck portion 187 slidably movable within the first cutout 170 (e.g., as shown in FIG. 5B). The second portion 152 of the housing 22 and the slider 100 are configured such that the third and fourth guide members 162 and 164 are slidably received in the first and second grooves 192 and 194, respectively, while the top part 186 is slidably received in the second concave portion 173 and slidably supported by the third and fourth portions 172 and 174 with the neck portion 187 slidably movable within the second cutout 176.

Figure 4B:
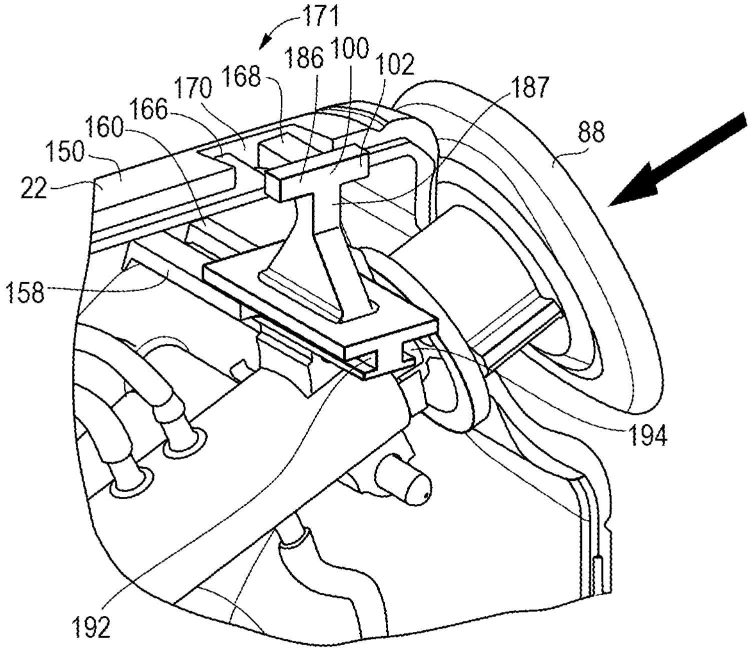
FIG. 4B is an enlarged detailed view of a portion of the system of FIG. 4.

Referring to FIGS. 1-5B, when the slider 100 is in the first position (e.g., as shown in FIGS. 2A and 4B), the top part 186 of the slider 100 is slidably received in the second concave portion 173 of the second portion 152 of the housing 22 and slidably supported by the third and fourth portions 172 and 174 with the neck portion 187 slidably movable within the second cutout 176 and the third and fourth guide members 162 and 164 slidably received in the first and second grooves 192 and 194 of the slider, respectively. When the slider 100 is in the second position 104 (e.g., as shown in FIGS. 2B and 5B), the top part 186 is slidably received in the first concave portion 171 of the first portion 150 of the housing 22 and slidably supported by the first and second portions 166 and 168 with the neck portion 187 slidably movable within the first cutout 170 and the first and second guide members 158 and 160 slidably received in the first and second grooves 192 and 194 of the slider 100, respectively.

The first and second portions 150 and 152 of the housing 22 are configured such that when they are coupled together, the first concave portion 171 and the second concave portion 173 form a continuous concave portion that slidably supports the top part 186 when the top part 186 moves between the first and second concave portions 171 and 173, the first cutout 170 and the second cutout 176 form a continuous cutout, which allows the neck portion 187 to be moved between the first and second cutouts 170 and 176, the first and third guide members 158 and 162 form a continuous guide member and the second and fourth guide members 160 and 164 form a continuous guide member, such that the slider 100 can be moved between the first position 102 and the second position 104 along the continuous guide members. The arm portion 182 of the slider 100 is configured such that when the slider 100 is in the first position 102, at least a portion of the proximal end portion 82*a* of the piston 82 is received in the cutout 184 (e.g., as shown in FIG. 4A) such that a distal movement of the button 88 is blocked by the arm portion 182, and when the slider 100 is in the second position 104, the arm portion 182 is out of the way of the distal movement of the button 88 (e.g., as shown in FIG. 5A).

The configuration and position of the first concave portion 171, the second concave portion 173, the switch 100 (e.g., the slider 100), the first through fourth guide members 158-164, the piston 82 of the first valve 80, and the button 88 may be varied, as desired and/or needed, without departing from the scope of the present invention, as long as the intended function/purpose/use discussed above may be achieved.

Figure 8A:
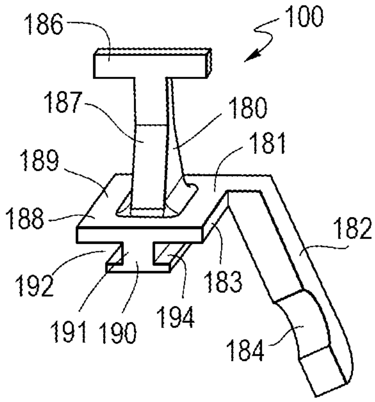
FIGS. 8A and 8B are perspective views of the switch of the system of FIG. 1.
Figure 8B:
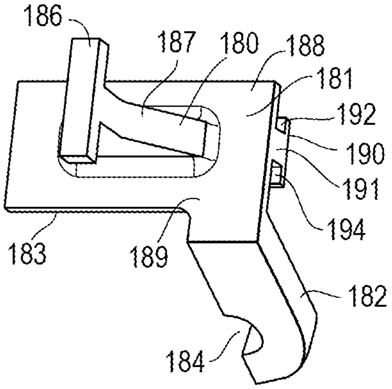
Figure 8C:
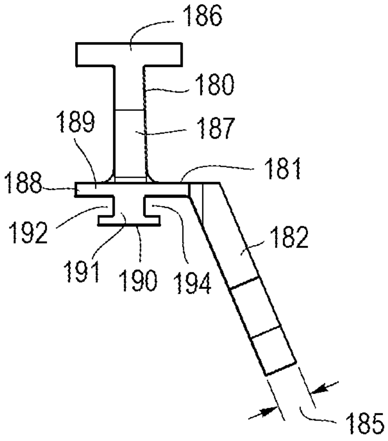
FIGS. 8C and 8D are side views of the switch of the system of FIG. 1.
Figure 8D:
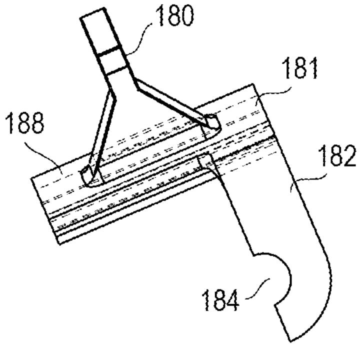

For example, the shape of the cutout 184 may be varied depending on the shape of the proximal end portion 82*a* of the first valve 80. As shown in FIGS. 4A and 8D, the proximal end portion 82*a* of the first valve 80 has a generally tubular shape, and the cutout 184 has a corresponding generally half-circle shape configured for receiving at least a portion of the proximal end portion 82*a* of the first valve 80. As another example, the width 185 (e.g., as shown in FIG. 8C) of the arm portion 182 is configured such that when the button 88 is in the first state 87 (e.g., as shown in FIG. 4A, the button is blocked by the width 185 of the arm portion 182), the first valve 80 is in such a state that pressurized fluid is delivered without the therapeutic agent 38, as discussed in greater detail above, and such that when the arm portion 182 is removed and the distal end 88*b* of the button 88 contacts the proximal end 81*a* of the main body 81 of the first valve 80 (e.g., as shown in FIG. 5A), the first valve 80 is in such a state that the therapeutic agent 38 is delivered.

Figure 36:
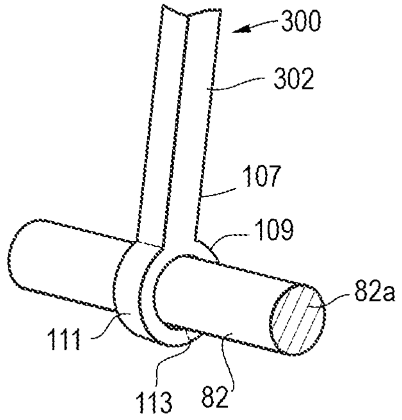
FIGS. 36 and 37 show enlarged partial illustrations of a switch of a system for delivering therapeutic agents in accordance with another embodiment.
Figure 37:
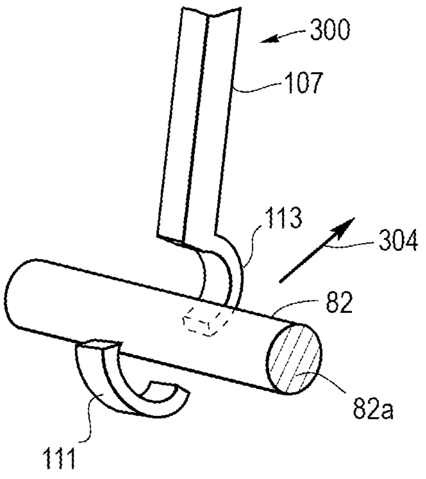

In some embodiments, as shown in FIGS. 36 and 37, the slider 300 may include a shaft 107 and a ring 109, where the ring 109 includes a snappable portion 111 and a remaining portion 113. The features discussed below with respect to this embodiment of slider 300 can be incorporated into other embodiments of the switch, the features and/or functions discussed herein with respect to other embodiments of the switch can be applied to this embodiment of the switch 300, and thus for the sake of brevity, similar features/functions will not be discussed in detail in this embodiment of the switch 300. The slider 300 is movable between a first position 302 and a second position 304 after the snappable portion 111 is snapped off. In some embodiments, for example, before the snapping, the slider 300 may look like the slider 100 in FIG. 4A (or the slider 100' in FIG. 26) but with a full 360-degree ring, and after the snapping, the slider 300 may look just like the slider 100 in FIG. 4A (or the slider 100' in FIG. 26).

Figure 26:
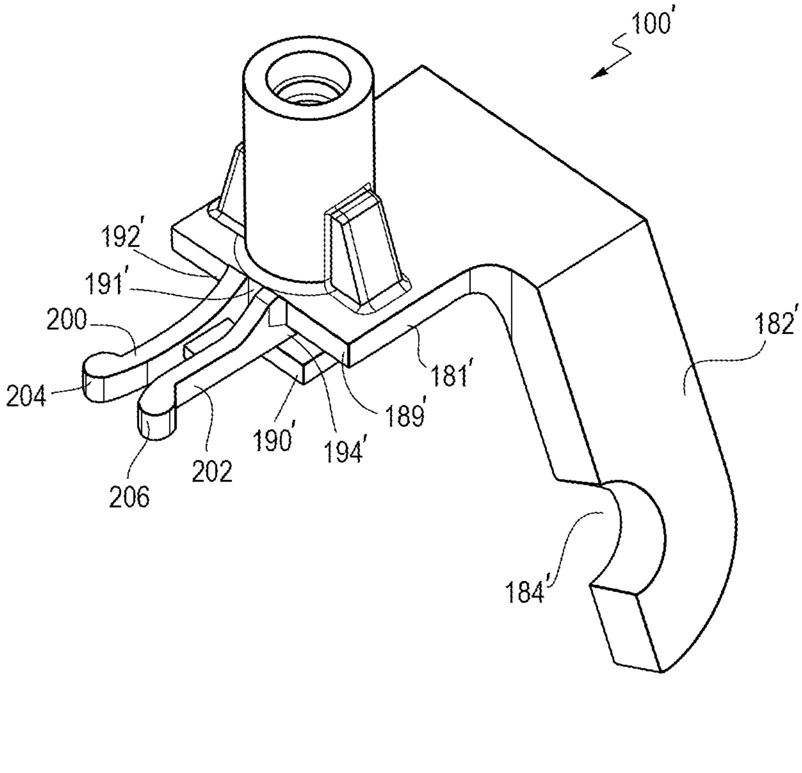
FIG. 26 is a perspective view of another embodiment of a portion of the switch of the system of FIG. 19.

In FIGS. 36 and 37, some parts of the slider 300 are omitted for illustrative purposes but may otherwise appear like the slider 100 in FIG. 4A (or the slider 100' in FIG. 26). Like in other embodiments of the switch discussed herein, when the slider 300 is in the first position 302 (like shown in FIG. 2A), the slider 300 allows the button to be depressed to a first state, allowing the pressurized fluid in the pressure source to flow through the first valve and into the catheter absent delivery of the therapeutic agent, and when the slider 300 is in the second position 304 (like shown in FIG. 2B), the slider 300 allows the button to be depressed to a second state, allowing the pressurized fluid in the pressure source to flow through the first valve, into the container, and urge the therapeutic agent in the container through the catheter.

In some embodiments, as shown in FIGS. 36 and 37, when the slider 300 is in the first position 302, the proximal end portion 82*a* of the piston 82 of the first valve extends through the ring 109 of the slider 300, where, like discussed in other embodiments of the switch, the ring 109 occupies a space, and where the space, when not occupied, allows movement of the button from the first state to the second state. Like discussed in other embodiments of the switch, when the slider 300 is in the first position 302, the ring 109 blocks the button such that the button can be moved distally a maximum of a first distance.

Moving the slider 300 from the first position 302 towards the second position 304 causes the snappable portion 111 to be snapped off (e.g., by the force applied on the shaft 107 and due to the proximal end portion 82*a* of the piston 82 extending through the ring 109), and after the snappable portion 111 is snapped off, the slider 300 can be moved to the second position 304. When the slider 300 is in the second position 304, the snappable portion 111 is already snapped off from the remaining portion 113 of the ring 109, and the remaining portion 113 of the ring 109 is moved away from the space (e.g., the remaining portion 113 no longer blocks the button), allowing the button to be depressed to the second state (e.g., like discussed in other embodiments of the switch, allowing the button to be moved distally a maximum of a second distance, where the first distance is smaller than the second distance).

This embodiment of the switch 300 is advantageous in that it ensures the slider is locked into position during transportation and device set-up, which reduces the risk of accidental deployment of the therapeutic agent. When pushing the slider for the first time and activating spraying of the therapeutic agent, the user must use added force to snap off the snappable portion 111. As one non-limiting example, the force required to snap the slider may be about 4-6 N to ensure that it withstands distributional forces but is not too large to prevent the user from being able to actuate the slider. The configuration of the shaft 107, the ring 109, the snappable portion 111, and the remaining portion 113 may be varied, as desired and/or needed, without departing from the scope of the present invention, as long as a portion of the switch needs to be snapped off to allow for the first time of deployment of the therapeutic agent.

Figure 35:
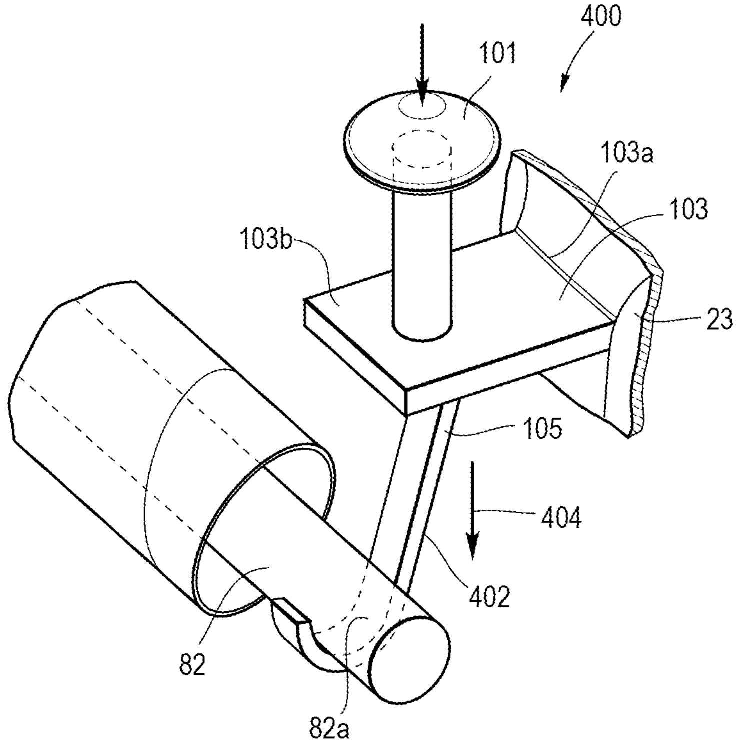
FIG. 35 is an enlarged illustration of a switch of a system for delivering therapeutic agents in accordance with another embodiment.

Moreover, in some embodiments, the switch may not be a slider, without departing from the scope of the present invention, as long as it is configured to selectively block the button to selectively deliver the pressurized fluid (without the therapeutic agent 38) or the therapeutic agent 38, as discussed above, including but not limited to, by rotating, pivoting, twisting, and/or pushing down the switch 100. As one non-limiting example, in some embodiments, as shown in FIG. 35, the switch 400 is movable between an upper/retracted position 402 and a lower/extended position 404 (discussed in greater detail below, but not specifically shown). The features discussed below with respect to this embodiment of switch 400 can be incorporated into other embodiments of the switch, the features and/or functions discussed herein with respect to other embodiments of the switch can be applied to this embodiment of the switch 400, and thus for the sake of brevity, similar features/functions will not be discussed in detail in this embodiment of the switch 400.

When the switch 400 is in the upper/retracted position 402, delivery of the therapeutic agent is prevented while delivery of the pressurized fluid is permitted, and when the switch 400 is in the lower/extended position 404, delivery of the therapeutic agent is permitted. Like discussed in other embodiments of the switch, when the switch 400 is in the upper/retracted position 402, the switch 400 allows the button to be depressed to a first state, allowing the pressurized fluid in the pressure source to flow through the first valve and into the catheter absent delivery of the therapeutic agent, and when the switch 400 is in the lower/extended position 404, the switch allows the button to be depressed to a second state, allowing the pressurized fluid in the pressure source to flow through the first valve, into the container, and urge the therapeutic agent in the container through the catheter.

As shown in FIG. 35, the switch 400 includes: a middle portion 103 pivotably connected to an inner surface 23 of the housing, a hook 105 extending downwardly from the middle portion 103, and a protrusion 101 extending upwardly from the middle portion 103, where the protrusion 101 extends above the housing. The switch 400 is configured such that pressing the protrusion 101 downwardly causes the hook 105 to move downwardly such that the switch 400 moves from the upper/retracted position 402 towards the lower/extended position 404. In some embodiments, the middle portion 103 may be a springboard extending between a first end portion 103*a* and a second end portion 103*b*, where the first end portion 103*a* is connected to the inner surface 23 of the housing and the second end portion 103*b* is cantilevered. The protrusion 101 and the hook 105 may both extend from the second end portion 103*b* of the middle portion 103.

When the protrusion 101 is not depressed, like discussed in other embodiments of the switch, the hook 105 occupies a space, where the space, when not occupied, allows movement of the button from the first state to the second state, and the hook 105 blocks the button such that the button can be moved distally a maximum of a first distance. When the protrusion 101 is depressed, the hook 105 moves downwardly (e.g., the hook 105 is moved away from the space), which, like discussed in other embodiments of the switch, allows the button to be moved distally a maximum of a second distance (e.g., allows the button to be depressed to the second state), where the first distance is smaller than the second distance.

As shown in FIG. 35, the hook 105 may be a J-hook, where when the protrusion 101 is not depressed, the hook 105 engages the proximal end portion 82*a* of the piston of the first valve, and where when the protrusion 101 is depressed, the hook 105 moves downwardly and does not engage the piston of the first valve. Holding the protrusion 101 down allows the switch 400 to stay in the lower/extended position 404, and releasing the protrusion 101 allows the hook 105 to move upwardly such that the switch 400 moves from the lower/extended position 404 to the upper/retracted position 402. This embodiment of the switch 400 is advantageous in that it will reduce the risk of accidental deployment of the therapeutic agent, as the user must hold down the protrusion when deploying the therapeutic agent. The configuration of the middle portion 103, the protrusion 101, and the hook 105 may be varied, as desired and/or needed, without departing from the scope of the present invention, as long as the switch needs to be held down to allow deployment of the therapeutic agent.

Figure 38:
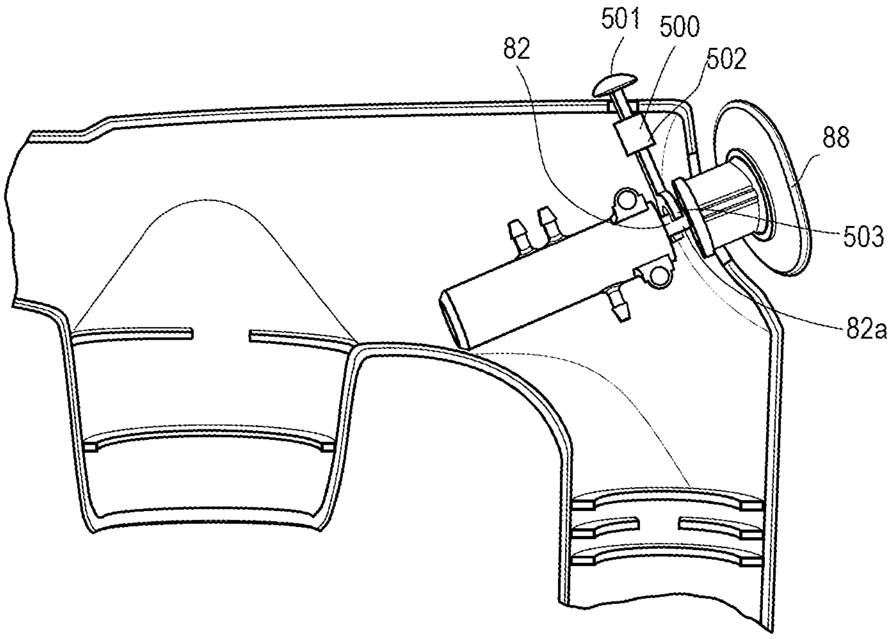
FIG. 38 is an illustration of a system for delivering therapeutic agents, showing another embodiment of a switch in an extended position.
Figure 39:
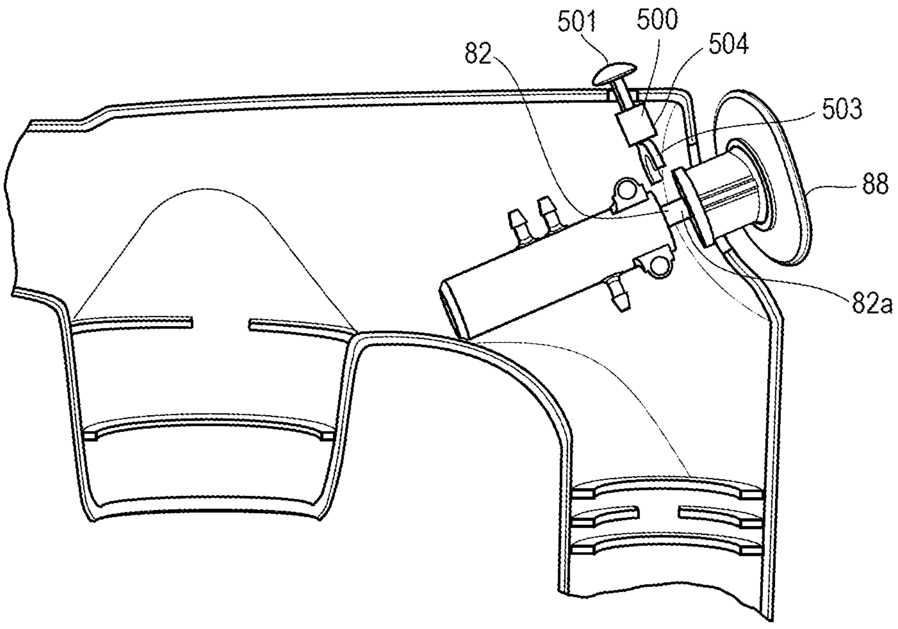
FIG. 39 is an illustration of the system of FIG. 38, showing the switch of FIG. 38 in a retracted position.
Figure 40:
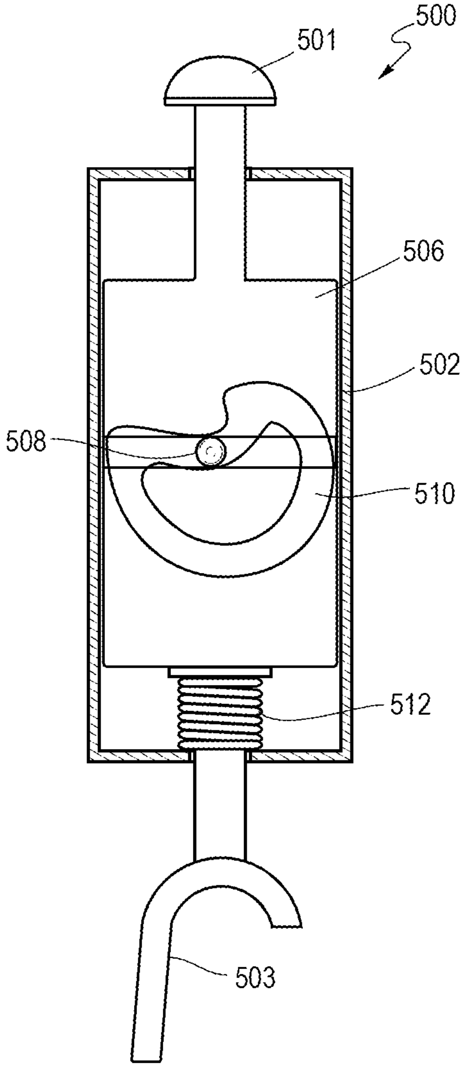
FIG. 40 is an illustration of the switch of FIG. 38, showing the switch in an extended position.
Figure 41:
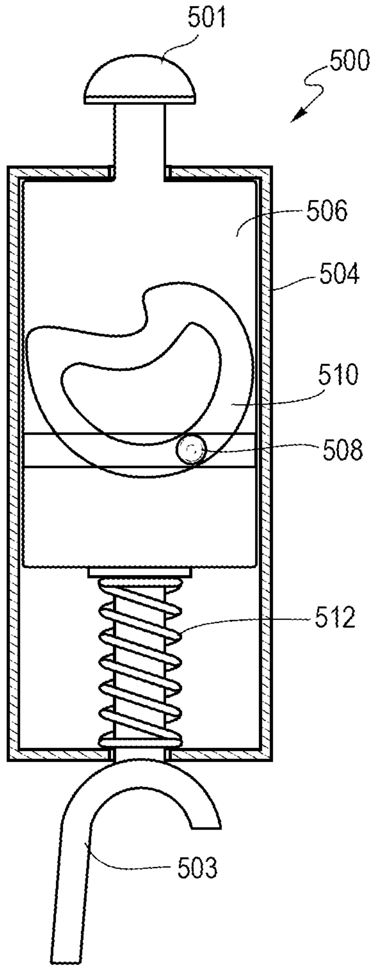
FIG. 41 is an illustration of the switch of FIG. 38, showing the switch in a retracted position.

As another non-limiting example, in some embodiments, as shown in FIGS. 38-41, the switch 500 is movable between an extended position 502 (e.g., as shown in FIGS. 38 and 40) and a retracted position 504 (e.g., as shown in FIGS. 39 and 41). When the switch 500 is in the extended position 502, delivery of the therapeutic agent is prevented while delivery of the pressurized fluid is permitted, and when the switch 500 is in the retracted position 504, delivery of the therapeutic agent is permitted. This embodiment of the switch 500 is advantageous for reducing the force required to actuate the switch 500. The features discussed below with respect to this embodiment of switch 500 can be incorporated into other embodiments of the switch, the features and/or functions discussed herein with respect to other embodiments of the switch can be applied to this embodiment of the switch 500, and thus for the sake of brevity, similar features/functions will not be discussed in detail in this embodiment of the switch 500.

The switch 500 includes a clickable button 501 and a hook 503 extending downwardly from the clickable button 501, where the switch 500 is configured to move between the extended position 502 and the retracted position 504 by pressing and then releasing the clickable button 501. As shown in FIGS. 40 and 41, the clickable button 501 includes a cam body 506 with a notch 510, a ball 508, and a spring 512. The functionality and the operating mechanism of the clickable button 501 are known in the writing art, and other embodiments of the clickable button in the writing art may be incorporated into the switch 500 without departing from the scope of the present invention, including, such as, the clickable button of a parker jotter pen.

When the switch 500 is in the extended position 502, the switch 500 allows the button 88 to be depressed to a first state, allowing the pressurized fluid in the pressure source to flow through the first valve and into the catheter absent delivery of the therapeutic agent, and when the switch 500 is in the retracted position 504, the switch 500 allows the button 88 to be depressed to a second state, allowing the pressurized fluid in the pressure source to flow through the first valve, into the container, and urge the therapeutic agent in the container through the catheter.

As shown in FIG. 38, when the switch 500 is in the extended position 502, the hook 503 engages a proximal end portion 82*a* of the piston 82 of the first valve and blocks the button 88 such that the button 88 can be moved distally a maximum of a first distance. As shown in FIG. 39, when the switch 500 is in the retracted position 504, the hook 503 moves upwardly and does not engage the piston 82 of the first valve, which allows the button 88 to be moved distally a maximum of a second distance, where the first distance is smaller than the second distance.

Referring to FIGS. 38 and 39, when the switch 500 is in the extended position 502 the hook 503 occupies a space, where the space, when not occupied, allows movement of the button 88 from the first state to the second state. When the switch is in the retracted position 504, the hook 503 is moved away from the space, allowing the button 88 to be depressed to the second state.

In use, with the catheter 90 connected to the outlet port 128 of the second valve 43, a user can make sure that the switch 100 is in the first position 102 and the second valve is in the first state 45 (e.g., as shown in FIG. 2A), and then actuate the pressure source 68 (e.g., by manipulating the actuator 26). To deliver the pressurized fluid without the therapeutic agent 38, the user may actuate the first valve 80 by fully depressing the button 88 until it is blocked by the switch 100 (e.g., as shown in FIGS. 4A and 16). This allows the pressurized fluid to flow through the first valve 80 and into the catheter 90 absent delivery of the therapeutic agent 38. While keeping the button 88 fully depressed, the user may insert the catheter 90 into the cavity of a patient (e.g., into a scope extending into the cavity of the patient) until it reaches the target site (e.g., when the distal end of the catheter 90 exits the scope).

Then to deliver the therapeutic agent 38, the user may release the button 88, move the switch 100 from the first position 102 to the second position 104 (e.g., as shown in FIG. 17B; such that the button 88 can be further depressed to actuate the first valve 80), transition the second valve 43 from the first state 45 to the second state 47 (e.g., as shown in FIG. 2B; which allows the pressurized fluid to urge the therapeutic agent 38 in the container 30 through the catheter 90), and fully depress the button 88 until it is blocked by the proximal end 81*a* of the main body 81 of the first valve 80. This allows the pressurized fluid to flow through the first valve 80 and into the container 30. By pressing and holding the button 88 for a desired number of times (e.g., three times), a desired number of shots (e.g. three shots) of therapeutic agent 38 may be delivered. After a desired amount of the therapeutic agent 38 has been delivered, the user may release the button 88, transition the second valve 43 back to the first state 45, and move the switch 100 back to the first position 102.

Figure 19:
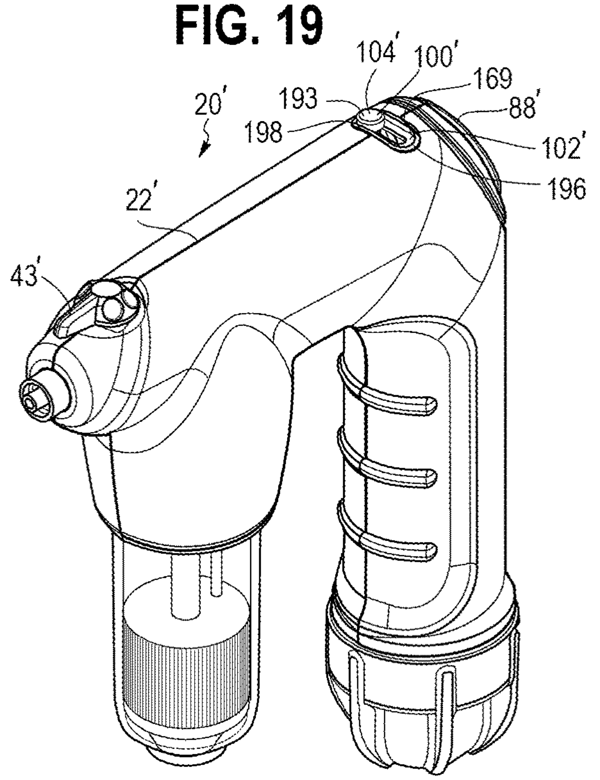
FIG. 19 is a perspective view of a system for delivering therapeutic agents in accordance with another embodiment, showing a housing, a front valve (second valve), a switch, and a button.
Figure 20:
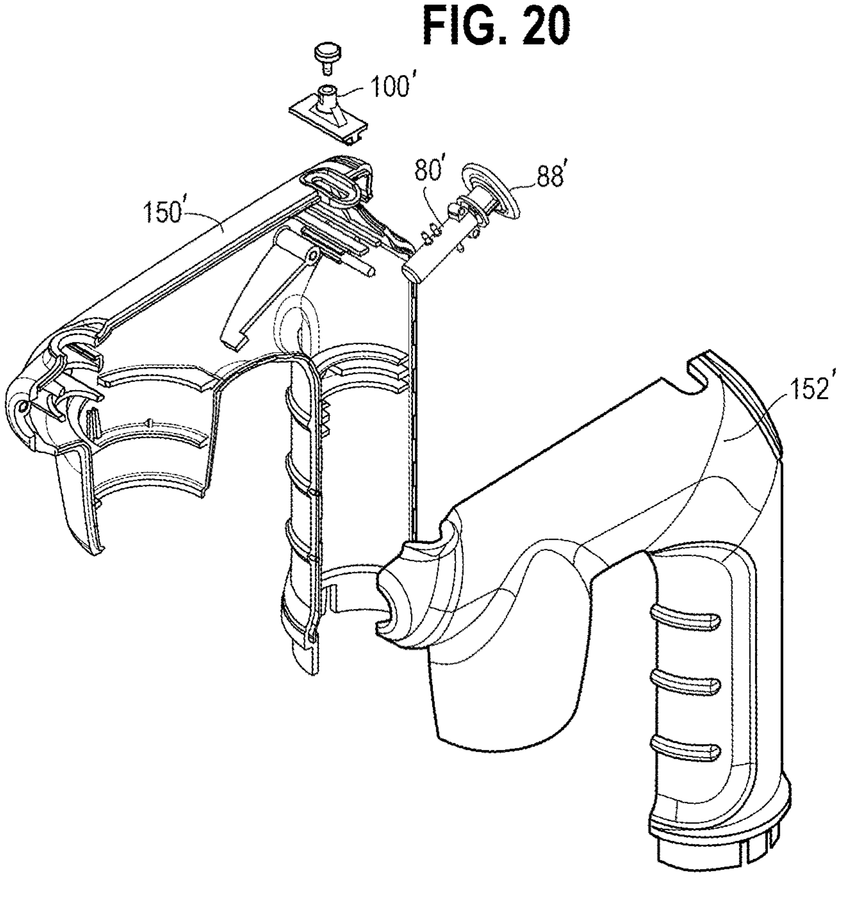
FIG. 20 is a partially exploded view of the system of FIG. 19, showing a first portion of the housing and a second portion of the housing.

Referring to FIGS. 19-24B, another embodiment of the system 20' for delivering therapeutic agents is disclosed. As shown in FIGS. 19 and 20, the system 20' includes a housing 22', a first valve 80', a second valve 43', a switch 100', and a button 88'. The features described above with respect to the embodiment of the system 20, as shown in FIGS. 1-18 may be included alone or in combination in the embodiment of the system 20', as shown in FIGS. 19-24B, which includes but not limited to the basic components forming the system 20', the configuration, positioning, and function of the basic components, and the method of manipulating the button 88' to selectively deliver the pressurized fluid without the therapeutic agent 38 or to deliver the therapeutic agent 38. For the sake of brevity, features discussed above will not be repeated with respect to this embodiment of the system 20', as shown in FIGS. 19-24B.

Figure 21:
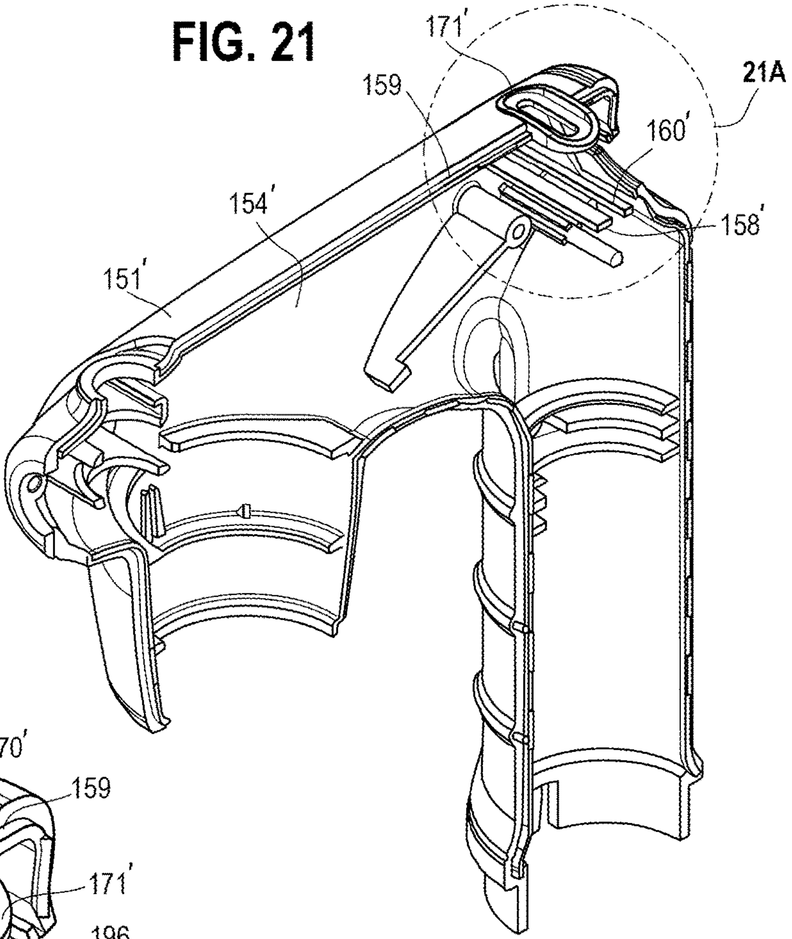
FIG. 21 is a perspective view of the first portion of the housing of the system of FIG. 19.
Figure 21A:
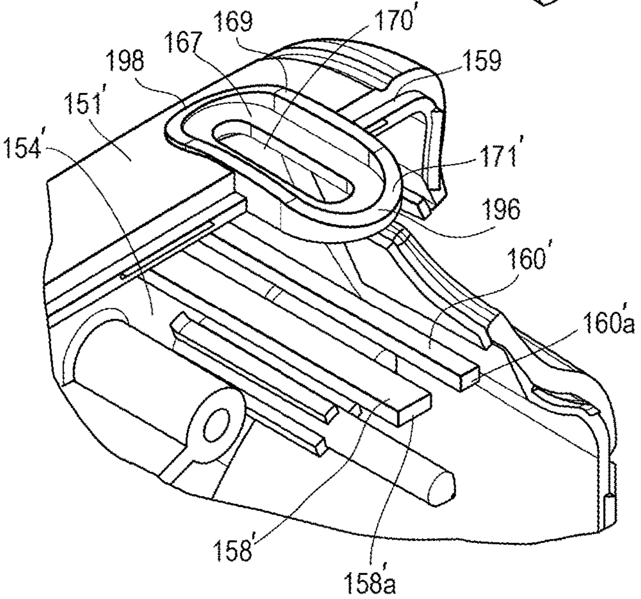
FIG. 21A is an enlarged detailed view of a portion of the first portion of the housing of FIG. 21.
Figure 21B:
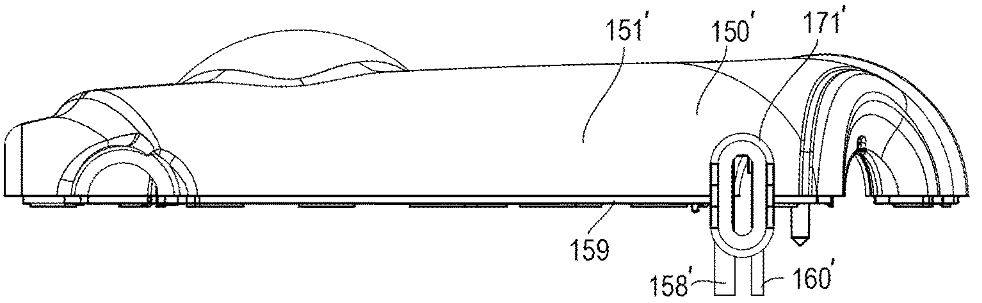
FIG. 21B is another perspective view of the first portion of the housing of FIG. 21.
Figure 22:
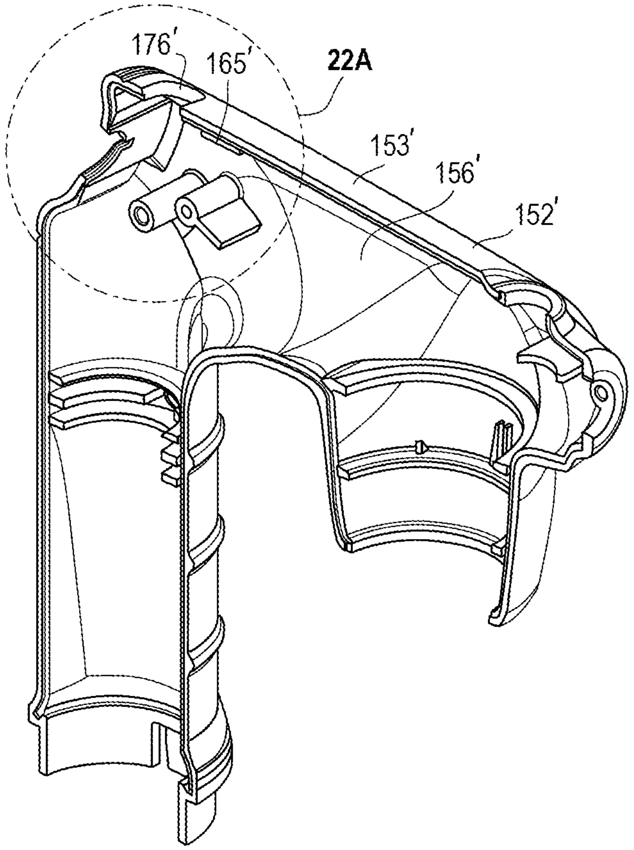
FIG. 22 is a perspective view of the second portion of the housing of the system of FIG. 19.
Figure 22A:
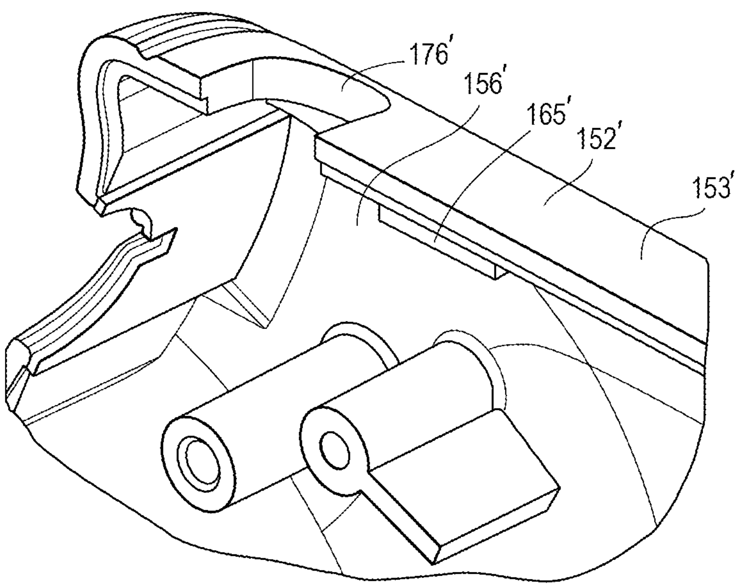
FIG. 22A is an enlarged detailed view of a portion of the second portion of the housing of FIG. 22.
Figure 23A:
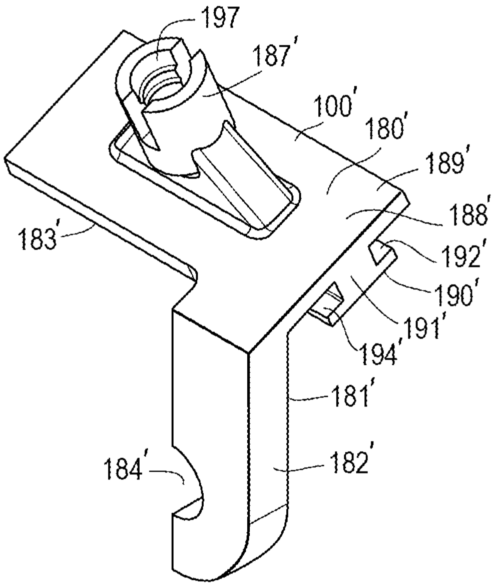
FIG. 23A is a perspective view of a portion of the switch of the system of FIG. 19.
Figure 23B:
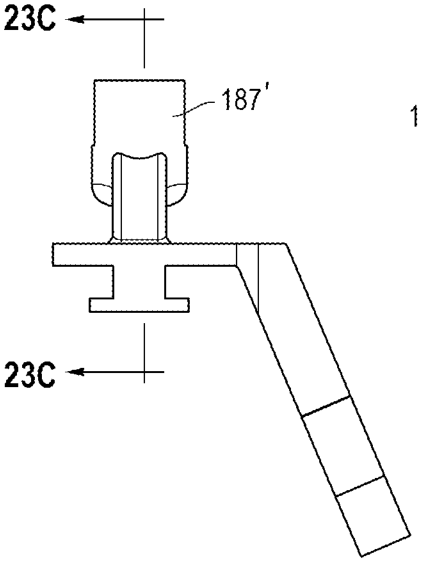
FIG. 23B is a side view of the portion of the switch of FIG. 23A.
Figure 23C:
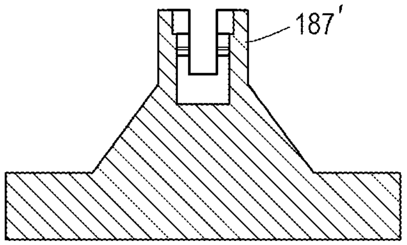
FIG. 23C is a cross-sectional view of the portion of the switch of FIG. 23A.
Figure 24A:
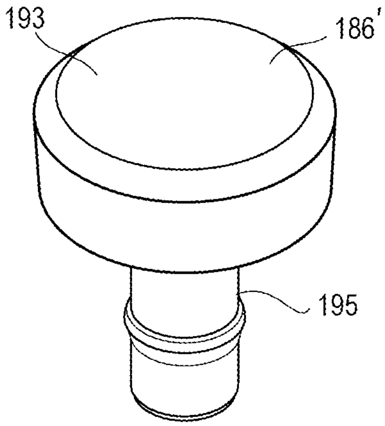
FIG. 24A is a perspective view of a top part of the switch of the system of FIG. 19.
Figure 24B:
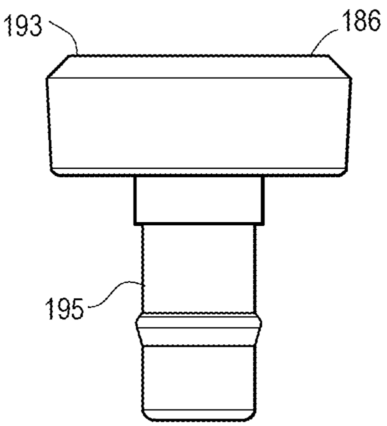
FIG. 24B is a side view of the top part of the switch of FIG. 24A.

Referring to FIGS. 20-22A, the housing 22' includes a first portion 150' and a second portion 152', which are configured such that when coupled together, forming a cavity configured for at least partially retaining, holding, engaging, and/or covering other components of the system 20' (e.g., the first valve 80') and slidably support the slider 100'. As shown in FIGS. 21-21B, the first portion 150' of the housing 22' includes a first upper portion 151' and a first inner surface 154'. As shown in FIGS. 22 and 22A, the second portion 152' of the housing 22' includes a second upper portion 153' and a second inner surface 156'.

The first upper portion 151' includes a cantilevered portion 171' at least partially extending outwardly from a side surface 159 of the first upper portion 151'. The cantilevered portion 171' includes a platform 167 surrounded by a flange 169 extending upwardly from the platform 167, where a first cutout 170' extends along at least a portion of the platform 167. The second upper portion 153' of the second portion 152' includes a second cutout 176' configured to receive at least the part of the cantilevered portion 171' that extends outwardly from the side surface 159 of the first upper portion 151', such that the first and second portions 150' and 152' may be coupled together forming the housing 22' with the cantilevered portion 171' at least partially received within the second cutout 176'. The cantilevered portion 171' is configured to slidably support at least a portion of the slider 100', as discussed in greater detail below.

The first portion 150' includes a first guide member 158' and a second guide member 160' extending outwardly from the first inner surface 154'. The first and second guide members 158' and 160' are spaced apart. The second portion 152' includes a guide support 165' extending outwardly from the second inner surface 156'. The first and second guide members 158' and 160' and the guide support 165' are configured such that when the first portion 150' and the second portion 152' of the housing 22' are coupled together forming the housing 22', the proximal ends **158'*a* and 160'*a* of the first and second guide members 158' and 160' engage the guide support 165' such that the first and second guide members 158' and 160' are supported and fixed by the guide support 165'. The first and second guide members 158' and 160' are configured to slidably support at least a portion of the slider 100'**, as discussed in greater detail below.

Referring to FIGS. 19, 20, and 23A-24B, the switch 100' (e.g., the slider 100') includes an upper portion 180' and a lower portion 181'. The upper portion 180' includes a top part 186' and a neck part 187'. The lower portion 181' includes a main portion 188', which includes an upper section 189', a lower section 190', and a middle section 191' extending between and connecting the upper and lower sections 189' and 190', where a first groove 192' and a second groove 194' are formed between the upper and lower sections 189' and 190' and disposed on opposite sides of the middle section 191'. The lower portion 181' also includes an arm portion 182' extending outwardly and downwardly from a side surface 183' of the upper section 189'. The arm portion 182' also includes a cutout 184' configured for receiving at least a portion of the proximal end portion of the piston of the first valve 80', as discussed in greater detail above with respect to the embodiment of the system 20.

The top part 186' includes an upper part 193 and a lower part 195. The neck part 187' includes a groove 197 configured to receive at least a part of the lower part 195 of the top part 186' such that the top part 186' and the neck part 187 are coupled together, such that movement of the slider 100' may be achieved by manipulating the upper part 193 of the top part 186'. This configuration is advantageous in that it provides ease of assembly as the top part 186' may be assembled easily by inserting the lower part 195 into the groove 197 of the neck part 187' after all other components of the system 20' have been assembled. As discussed in greater detail above with respect to the embodiment of the system 20, the first portion 150' of the housing 22' and the slider 100' are configured such that the first and second guide members 158' and 160' are slidably received in the first and second grooves 192' and 194', respectively, while the upper part 193 of the top part 186' of the slider 100' is slidably received in the cantilevered portion 171' and slidably supported by the platform 167' with the neck portion 187' slidably movable within the first cutout 170'.

When the upper part 193 of the slider 100' is disposed at the first end 196 of the flange 169, the slider 100' is in the first position 102', where at least a portion of the proximal end portion of the piston of the first valve 80' is received in the cutout 184' of the arm portion 182', such that a distal movement of the button 88' is blocked by the arm portion 182'. When the upper part 193 of the slider 100' is disposed at the second end 198 of the flange 169, the slider 100' is in the second position 104', where the arm portion 182' is out of the way of the distal movement of the button 88'. The ability to move the upper part 193 of the slider 100' along the platform 167' and along the first and second guide members 158' and 160' between the first position 102' and the second position 104' is advantageous for providing a smooth movement/operation of the slider 100'.

Figure 25:
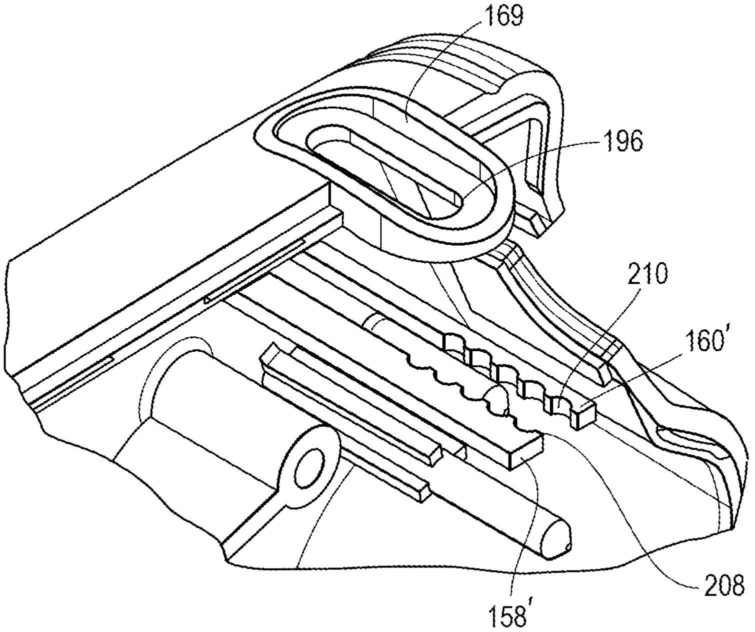
FIG. 25 is an enlarged perspective view of another embodiment of the guide members of the first portion of the housing of the system of FIG. 19.

In some embodiments, the guide members 158' and 160' and the switch 100' (e.g., the slider 100') may be configured to prevent unintentional relative movement between the slider 100' and guide members 158' and 160'. For example, as shown in FIG. 25, the guide members 158' and 160' each may include a plurality of cutouts 208 and 210. In some embodiments, the plurality of cutouts 208 and 210 may each be continuous along a length of respective guide members 158' and 160'. For example, as shown in FIG. 25, the plurality of cutouts 208 and 210 each include five cutouts that are continuously disposed, where each cutout has the same/similar configuration (e.g., shape, size). As shown in FIG. 25, each cutout has a curved configuration.

In some embodiments, as shown in FIG. 26, a pair of arms 200 and 202 may extend outwardly from opposite sides of the middle section 191' of the slider 100' and along the respective directions of the first and second grooves 192' and 194', where the distal ends of the pair of arms 200 and 202 each include a protrusion 204 and 206 extending outwardly from the respective arms 200 and 202. The protrusions 204 and 206 each may be configured to be received in a respective cutout 210 and 208. Referring to FIGS. 19, 20, 25, and 26, the arms 200 and 202 and the protrusions 204 and 206 are configured such that when the upper part 193 of the slider 100' is disposed at the first end 196 of the flange 169, the slider 100' is in the first position 102', where the protrusions 204 and 206 each engage/are at least partially received in corresponding cutouts 210 and 208 in respective guide members 160' and 158', such that unintentional movement (e.g., during transportation) of the slider 100' relative to the guide members 158' and 160' will be prevented, which is advantageous for preventing accidental movement of the slider 100' between the first and second positions 102' and 104'.

A user may manually move the slider 100' between the first and second positions 102' and 104' by pushing on the slider 100' in the corresponding directions. During the movement of the slider 100', the plurality of cutouts 208 and 210 provide tactile feedback to the user, as the protrusions 204 and 206 each move in/out the corresponding cutouts 210 and 208 in the guide members 160' and 158'. The configuration (e.g., shape, size), number, and position of the cutouts 208 and 210 in each guide member 158' and 160' and the configuration (e.g., shape, size, length) of the arms 202 and 200 and the protrusions 206 and 204 may be varied, as desired and/or needed, without departing from the scope of the present invention, as long as the tactile feedback mentioned above can be provided and/or the function of preventing accidental movement between the slider 100' and the guide members 158' and 160' can be achieved as the slider 100' moves between the first and second positions 102' and 104'.

Figure 31:
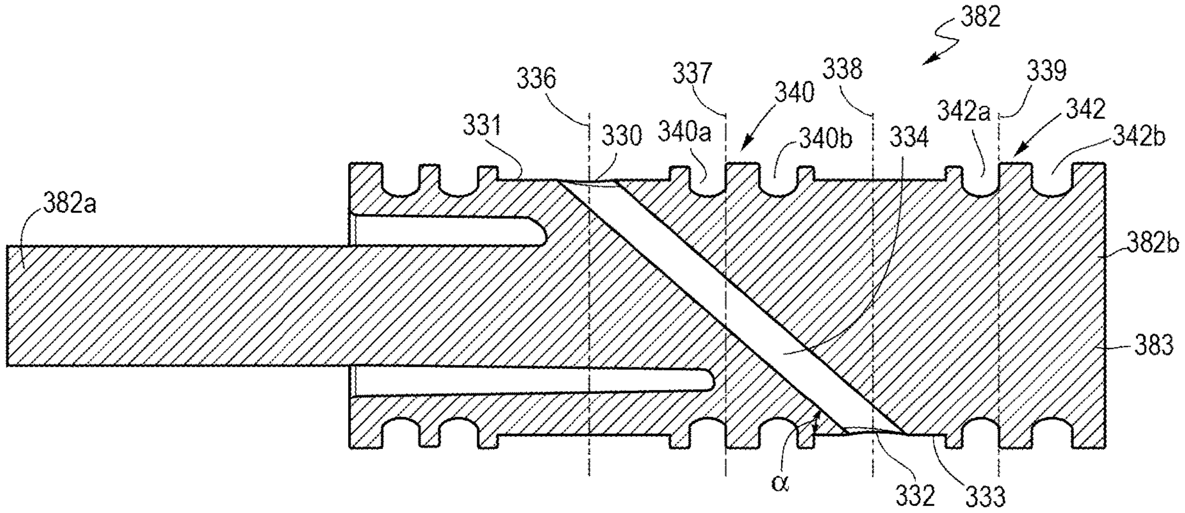
FIG. 31 is a cross-sectional view of the piston of FIG. 28.
Figure 32:
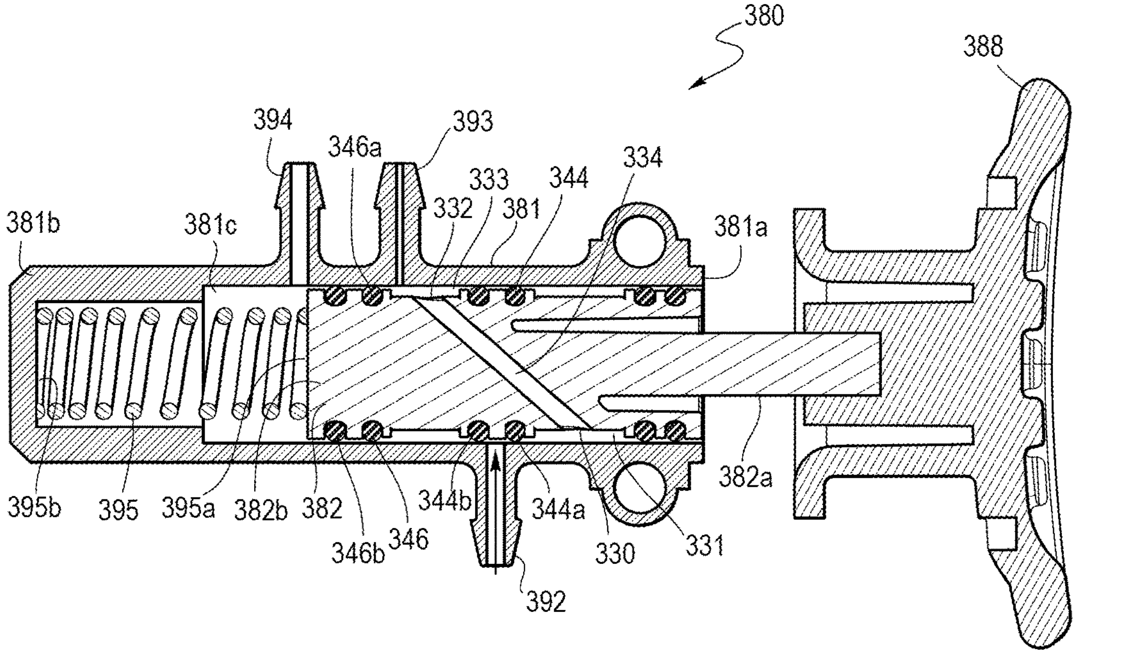
FIG. 32 is a cross-sectional view of a back valve including the piston of FIG. 28 in a default state.
Figure 33:
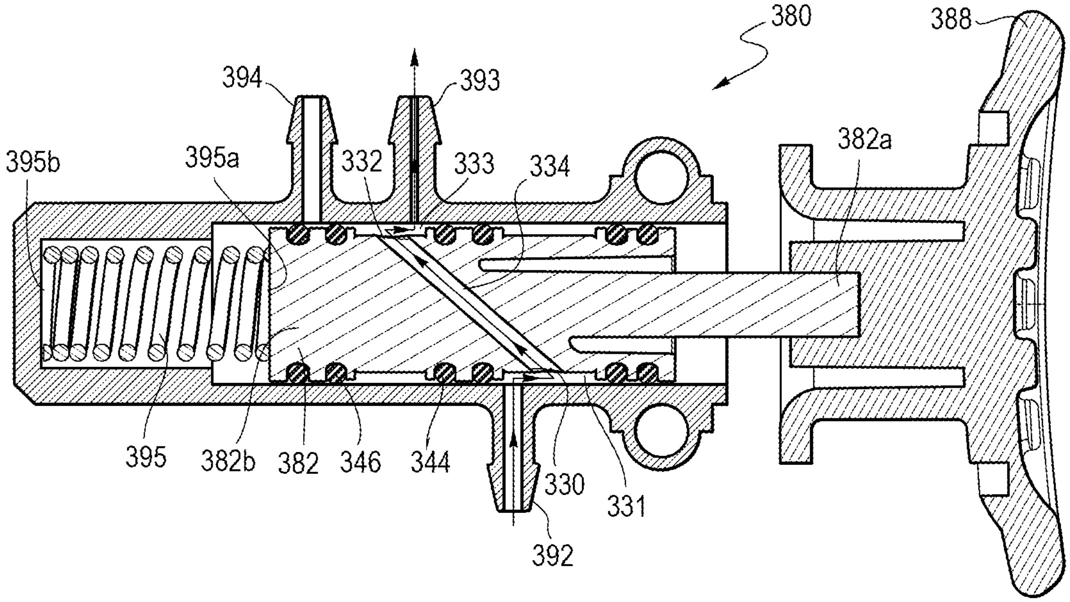
FIG. 33 is a cross-sectional view of the back valve of FIG. 32 in a positive pressure position.
Figure 34:
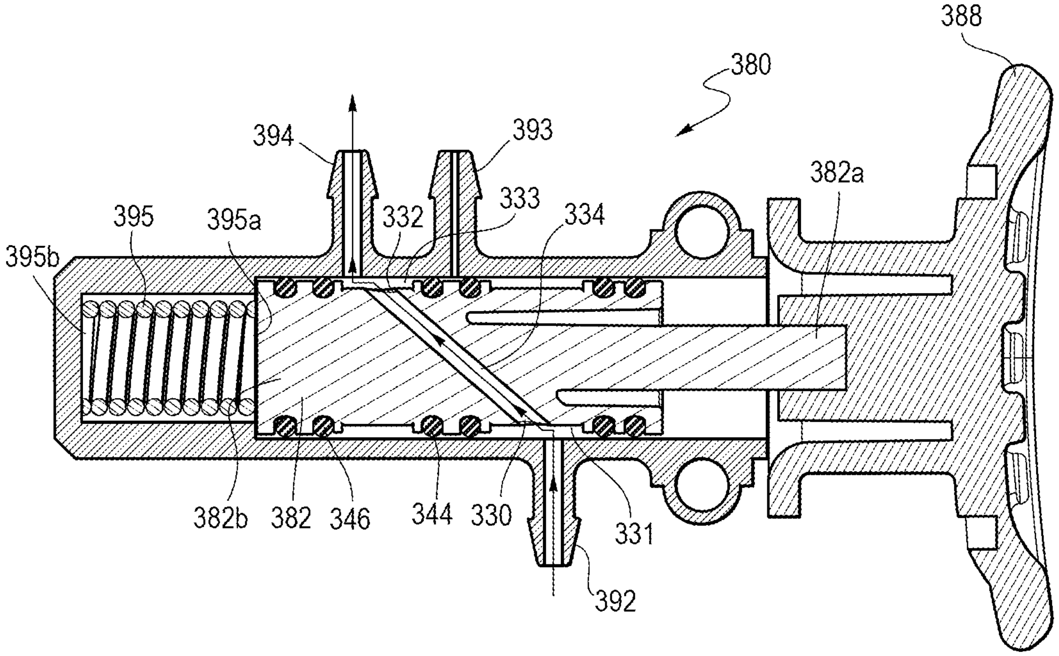
FIG. 34 is a cross-sectional view of the back valve of FIG. 32 in a therapeutic agent delivery position.

Referring to FIGS. 28-34, another embodiment of the piston 382 of the first valve 380 is shown, which may be incorporated into any embodiment of the system 20, described above, with any embodiment of other components described above (e.g., housing, slider), as desired and/or needed, without departing from the scope of the present invention. The first valve 380 comprises a main body 381 having a proximal end 381*a*, a distal end 381*b*, and an inner lumen 381*c* extending between the proximal end 381*a* and the distal end 381*b*. A piston 382, which has proximal and distal end portions 382*a* and 382*b*, is disposed at least partially within the main body 381 and is slidably movable along a length of the inner lumen 381*c* of the main box 381. A button 388 is configured to be connected to the proximal end portion 382*a* of the piston 382 such that depression of the button 388 causes the piston 382 to move distally along a length of the inner lumen 381*c* of the main body 381. This proximal end portion 382*a* of the piston 382 may extend a distance outside of the main body 381 (e.g., as shown in FIG. 32), to facilitate coupling to the button 388. The distal end portion 382*b* of the piston 382 may be positioned adjacent to a proximal end 395*a* of a compression spring 395 (e.g., as shown in FIGS. 32-34). In this manner, the piston 382 can be provided with a default state (e.g., as shown in FIG. 32, when no force is applied to the button 388) in which the piston 382 is inclined to be disposed further proximally, but if the user applies a sufficient force to the button 388 then the piston 382 can be moved distally against the force of the compression spring 395, for purposes described below. Once the button 388 is released (e.g., not depressed), the piston 382 returns to the default state.

Various inlet and outlet ports may be associated with the first valve 380. In the embodiment shown in FIGS. 32-34, the main body 381 includes an inlet port 392, a first outlet port 393, and a second outlet port 394. The inlet port 392 of the first valve 380 may be coupled to the tubing 75 extending from the pressure outlet 72 of the regulator valve 70 (e.g., as shown in FIG. 4, described above with respect to another embodiment of the first valve 80), thus providing pressurized fluid at a predetermined pressure into the first valve 380. The first outlet port 393 may be coupled to the tubing 65 extending from the first inlet port 124 of the second valve 43 (e.g., as shown in FIG. 4, described above with respect to another embodiment of the first valve 80). The second outlet port 394 may be coupled to the tubing 61 extending from the inlet port 62 of the cap 60 (e.g., as shown in FIG. 4, described above with respect to another embodiment of the first valve 80).

Referring to FIGS. 28-31, the piston 382 of the first valve 380 may include a generally tubular body 383 having spaced apart first and second openings 330 and 332 disposed on an outer surface of the piston 382. The first and second openings 330 and 332 are connected by a bridge 334 extending through the piston 382 at an angle $\alpha$ with respect to a length of the piston 382. The bridge 334 may extend through at least a portion of the piston 382. In some embodiments, as shown in FIG. 31, the angle $\alpha$ is smaller than 90 degrees. With this configuration, fluid communication routes can align to permit flow between the first and second openings 330 and 332 via the bridge 334 inside the piston 382.

The piston 382 further comprises spaced apart first and second recessed portions 331 and 333 disposed on an outer surface of the piston 382. The first opening 330 is disposed in the first recessed portion 331 and the second opening 332 is disposed in the second recessed portion 333. The presence of the first and second recessed portions 331 and 333 is advantageous for assisting with air flow delivery to the respective first and second outlet ports 393 and 394. As shown in FIG. 31, the first recessed portion 331 may extend around a circumference of a first cross section 336 of the piston 382 with a constant depth, and the second recessed portion 333 may extend around a circumference of a second cross section 338 of the piston 382 with a constant depth.

Referring to FIG. 31, the piston 382 of the first valve 380 may further include spaced apart first valley 340 and second valley 342 disposed on an outer surface of the piston 382. The first and second valleys 340 and 342 are configured for respectively receiving first and second sealing members 344 and 346 configured for selectively closing the inlet port 392, the first outlet port 393, or the second outlet port 394, as discussed in greater detail below. The first valley 340 may extend around a circumference of a third cross section 337 of the piston 382 with a constant depth, and the second valley 342 may extend around a circumference of a fourth cross section 339 of the piston 382 with a constant depth. The first, second, third, and fourth cross sections 336, 338, 337, and 339 of the piston 382 may be spaced apart and parallel to each other. As shown in FIG. 31, the first valley 340 may be disposed proximal to the second valley 342, the first opening 330 may be disposed proximal to the first valley 340, and the second opening 332 may be disposed between the first and second valleys 340 and 342.

As shown in FIG. 31, the first valley 340 may include a first sub-valley 340*a* and a second sub-valley 340*b* spaced apart by a portion of the outer surface of the piston 382. The second valley 342 may include a third sub-valley 342*a* and a fourth sub-valley 342*b* spaced apart by a portion of the outer surface of the piston 382. The first and second sealing members 344 and 346 each may include at least one O-Ring configured to be received in the respective first and second valleys 340 and 342. Referring to FIGS. 31 and 32, the first sealing member 344 includes a first O-Ring 344*a* configured to be disposed in the first sub-valley 340*a* and a second O-Ring 344*b* configured to be disposed in the second sub-valley 340*b*. The second sealing member 346 includes a third O-Ring 346*a* configured to be disposed in the third sub-valley 342*a* and a fourth O-Ring 346*b* configured to be disposed in the fourth sub-valley 342*b*.

As shown in FIG. 32, the first valve 380 is configured such that when the button 388 is not depressed (e.g., no force is applied to the button 388), the first sealing member 344 is axially aligned with the inlet port 392, such that the inlet port 392 is blocked and there is no fluid communication between the inlet port 392 and any one of the first and second outlet ports 393 and 394.

In use (e.g., when the first valve 380 with the piston 382 is incorporated into the system 20), the piston 382 is disposed at least partially within the main body 381 and is slidably movable along a length of the inner lumen 381*c* of the main body 381. The inlet port 392, the first outlet port 393, and the second outlet port 394 of the main body 381 of the first valve 380, the first and second valleys 340 and 342 of the piston 382, and the first and second sealing members 344 and 346 are configured and spaced such that when the second sealing member 346 is axially aligned with the second outlet port 394, the first sealing member 344 is axially offset from the inlet port 392 and the first outlet port 393, such that fluid communication (e.g., a first fluid communication) is established between the inlet port 392 and the first outlet port 393 via the first and second openings 330 and 332 and the bridge 334 (e.g., as shown in FIG. 33, where, as described above with respect to FIGS. 4A and 16C, the slider 100 is in the first position 102 (e.g., as shown in FIGS. 2A and 4A) and allows the button 388 to be partially depressed to the extent shown in FIG. 33, allowing the pressurized fluid in the pressure source 68 to flow through the first valve 380 and into the catheter 90 absent delivery of the therapeutic agent).

In addition, when the first sealing member 344 is axially aligned with the first outlet port 393, the first sealing member 344 is axially offset from the inlet port 392 and the second sealing member 346 is axially offset from the second outlet port 394, such that fluid communication (e.g., a second fluid communication) is established between the inlet port 392 and the second outlet port 394 via the first and second openings 330 and 332 and the bridge 334 (e.g., as shown in FIG. 34, where, as described above with respect to FIGS. 5A and 18B, the slider 100 is in the second position 104 (e.g., as shown in FIGS. 2B and 5A), and allows the button 388 to be depressed to the extent as shown in FIG. 34), allowing the pressurized fluid in the pressure source 68 to flow through the first valve 380, into the container 30, and urge the therapeutic agent 38 in the container 30 through the catheter 90, as discussed in greater detail above).

It will be appreciated that the number, configuration (e.g., shape/size), and position of the openings, bridge(s), valleys, sub-valleys, and sealing members included in the piston 382 and the inlet and outlet ports associated with the first valve 380 may be varied, as desired and/or needed, without departing from the scope of the present invention, as long as fluid communication routes can be selectively aligned to permit flow between the inlet port and the outlet port connected to the tubing 65 coupled to the inlet port 124 of the second valve 43 in one state of the first valve 380, and to permit flow between the inlet port and the outlet port connected to the tubing 61 coupled to the inlet port 62 of the cap 60 in another state of the first valve 380, such that the pressurized fluid (without the therapeutic agent 38) or the therapeutic agent 38 can be selectively delivered using the first valve 380 and the button 388 coupled to the first valve 380.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system suitable for delivering a therapeutic agent to a target site, the system comprising:

a container for holding a therapeutic agent;

a pressure source having pressurized fluid, the pressure source in selective fluid communication with at least a portion of the container;

a catheter in selective fluid communication with the container and configured for delivery of the therapeutic agent or the pressurized fluid to a target site; and a housing configured to securely retain the container and movably support a switch, and an actuator, wherein the switch is movable between a first position and a second position, wherein when the switch is in the first position, the actuator is configured to be in a first state and delivery of the therapeutic agent is prevented while delivery of the pressurized fluid is permitted, and wherein when the switch is in the second position, the actuator is configured to be in a second state and delivery of the therapeutic agent is permitted.

2. The system of claim 1, further comprising:

a first valve connected between the pressure source and the container; and wherein the actuator comprises a button, the button configured to selectively actuate the first valve to deliver the pressurized fluid without the therapeutic agent or to deliver the therapeutic agent, wherein when the switch is in the first position, the switch allows the button to be depressed to a first state, allowing the pressurized fluid in the pressure source to flow through the first valve and into the catheter absent delivery of the therapeutic agent, and wherein when the switch is in the second position, the switch allows the button to be depressed to a second state, allowing the pressurized fluid in the pressure source to flow through the first valve, into the container, and urge the therapeutic agent in the container through the catheter.

3. The system of claim 2, further comprising a second valve connected between the container and the catheter, wherein when the second valve is in a first state, the catheter is not in fluid communication with the container, and wherein when the second valve is in a second state, the catheter is in fluid communication with the container.

4. The system of claim 1, wherein the actuator comprises a button, and when the switch is in the first position, the switch blocks the button such that the button can be moved distally a maximum of a first distance, wherein when the switch is in the second position, the switch allows the button to be moved distally a maximum of a second distance, and wherein the first distance is smaller than the second distance.

5. The system of claim 1, wherein when the switch is in the first position, the switch occupies a space, and wherein the space, when not occupied, allows movement of the actuator from the first state to the second state.

6. The system of claim 5, wherein when the switch is in the second position, the switch is moved away from the space, allowing the actuator to be depressed to the second state.

7. The system of claim 1, wherein the switch comprises a slider, and the housing is configured to slidably support the slider.

8. The system of claim 1, wherein the first position of the switch is a retracted position and the second position of the switch is an extended position, wherein when the switch is in the retracted position, delivery of the therapeutic agent is prevented while delivery of the pressurized fluid is permitted, and wherein when the switch is in the extended position, delivery of the therapeutic agent is permitted.

9. The system of claim 1, wherein the first position of the switch is an extended position and the second position of the switch is a retracted position, wherein when the switch is in the extended position, delivery of the therapeutic agent is prevented while delivery of the pressurized fluid is permitted, and wherein when the switch is in the retracted position, delivery of the therapeutic agent is permitted.

10. A system suitable for delivering a therapeutic agent to a target site, the system comprising:

a container for holding a therapeutic agent;

a pressure source having pressurized fluid, the pressure source in selective fluid communication with at least a portion of the container;

a catheter in selective fluid communication with the container and configured for delivery of the therapeutic agent or the pressurized fluid to a target site;

a housing configured to securely retain the container and movably support a switch, wherein the switch is movable between a first position and a second position, wherein when the switch is in the first position, delivery of the therapeutic agent is prevented while delivery of the pressurized fluid is permitted, and wherein when the switch is in the second position, delivery of the therapeutic agent is permitted; and further comprising a first valve connected between the pressure source and the container; and a button configured to selectively actuate the first valve to deliver the pressurized fluid without the therapeutic agent or to deliver the therapeutic agent, wherein when the switch is in the first position, the switch allows the button to be depressed to a first state, allowing the pressurized fluid in the pressure source to flow through the first valve and into the catheter absent delivery of the therapeutic agent, and wherein when the switch is in the second position, the switch allows the button to be depressed to a second state, allowing the pressurized fluid in the pressure source to flow through the first valve, into the container, and urge the therapeutic agent in the container through the catheter.

11. The system of claim 10, wherein the switch comprises a slider, and the housing is configured to slidably support the slider.

12. The system of claim 10, wherein the first position of the switch is a retracted position and the second position of the switch is an extended position, wherein when the switch is in the retracted position, delivery of the therapeutic agent is prevented while delivery of the pressurized fluid is permitted, and wherein when the switch is in the extended position, delivery of the therapeutic agent is permitted.

13. A system suitable for delivering a therapeutic agent to a target site, the system comprising:

a container for holding a therapeutic agent;

a pressure source having pressurized fluid, the pressure source in selective fluid communication with at least a portion of the container;

a catheter in selective fluid communication with the container and configured for delivery of the therapeutic agent or the pressurized fluid to a target site; and a housing configured to securely retain the container and movably support a switch, wherein the switch is movable between a first position and a second position, wherein when the switch is in the first position, delivery of the therapeutic agent is prevented while delivery of the pressurized fluid is permitted, and wherein when the switch is in the second position, delivery of the therapeutic agent is permitted, wherein when the switch is in the first position, the switch blocks a button such that the button can be moved distally a maximum of a first distance, wherein when the switch is in the second position, the switch allows the button to be moved distally a maximum of a second distance, and wherein the first distance is smaller than the second distance.

14. The system of claim 13, wherein when the switch is in the first position, the switch occupies a space, and wherein the space, when not occupied, allows movement of the button from the first distance to the second distance.

15. The system of claim 14, wherein when the switch is in the second position, the switch is moved away from the space, allowing the button to be depressed to the second distance.

16. The system of claim 13, wherein the switch comprises a slider, and the housing is configured to slidably support the slider.

17. The system of claim 13, wherein the first position of the switch is a retracted position and the second position of the switch is an extended position, wherein when the switch is in the retracted position, delivery of the therapeutic agent is prevented while delivery of the pressurized fluid is permitted, and wherein when the switch is in the extended position, delivery of the therapeutic agent is permitted.

18. A system suitable for delivering a therapeutic agent to a target site, the system comprising:

a container for holding a therapeutic agent;

a pressure source having pressurized fluid, the pressure source in selective fluid communication with at least a portion of the container;

a catheter in selective fluid communication with the container and configured for delivery of the therapeutic agent or the pressurized fluid to a target site; and a housing configured to securely retain the container and movably support a switch, wherein the switch is movable between a first position and a second position, wherein when the switch is in the first position, delivery of the therapeutic agent is prevented while delivery of the pressurized fluid is permitted, wherein when the switch is in the second position, delivery of the therapeutic agent is permitted, and wherein when the switch is in the first position, the switch occupies a space, and wherein the space, when not occupied, allows movement of a button from a first state to a second state.

19. The system of claim 18, wherein when the switch is in the second position, the switch is moved away from the space, allowing the button to be depressed to the second state.

20. The system of claim 18, wherein the switch comprises a slider, and the housing is configured to slidably support the slider.

* * * * *